(12) United States Patent
Kannicht et al.

(10) Patent No.: US 12,171,808 B2
(45) Date of Patent: *Dec. 24, 2024

(54) GLYCOSYLATED VWF FUSION PROTEINS WITH IMPROVED PHARMACOKINETICS

(71) Applicant: OCTAPHARMA AG, Lachen (CH)

(72) Inventors: Christoph Kannicht, Berlin (DE); Barbara Solecka-Witulska, Berlin (DE); Stefan Winge, Årsta (SE); Tilo Schwientek, Neuss (DE)

(73) Assignee: OCTAPHARMA AG, Lachen (CH)

( * ) Notice: Subject to any disclaimer, the term of this patent is extended or adjusted under 35 U.S.C. 154(b) by 693 days.

This patent is subject to a terminal disclaimer.

(21) Appl. No.: 16/302,942

(22) PCT Filed: Apr. 26, 2017

(86) PCT No.: PCT/EP2017/059976
§ 371 (c)(1),
(2) Date: Nov. 19, 2018

(87) PCT Pub. No.: WO2017/198435
PCT Pub. Date: Nov. 23, 2017

(65) Prior Publication Data
US 2019/0169268 A1    Jun. 6, 2019

(30) Foreign Application Priority Data

May 20, 2016 (EP) .................................. 16170690

(51) Int. Cl.
| | |
|---|---|
| *A61K 38/37* | (2006.01) |
| *A61K 38/00* | (2006.01) |
| *A61P 7/04* | (2006.01) |
| *C07K 14/745* | (2006.01) |
| *C07K 14/755* | (2006.01) |
| *C12N 15/62* | (2006.01) |

(52) U.S. Cl.
CPC ............... *A61K 38/37* (2013.01); *A61P 7/04* (2018.01); *C07K 14/745* (2013.01); *C07K 14/755* (2013.01); *C12N 15/62* (2013.01); *A61K 38/00* (2013.01); *C07K 2319/00* (2013.01); *C07K 2319/02* (2013.01); *C07K 2319/20* (2013.01); *C07K 2319/31* (2013.01); *C07K 2319/35* (2013.01)

(58) Field of Classification Search
CPC ...... A61K 38/37; A61K 38/00; C07K 14/745; C07K 14/755; C07K 2319/00; C07K 2319/31; C07K 2319/02; C07K 2319/20; C07K 2319/35; A61P 7/04; C12N 15/62
See application file for complete search history.

(56) References Cited

U.S. PATENT DOCUMENTS

| | | | |
|---|---|---|---|
| 2010/0183556 A1* | 7/2010 | Choi | C07K 14/755 |
| | | | 435/320.1 |
| 2015/0023959 A1* | 1/2015 | Chhabra | A61P 7/04 |
| | | | 514/14.1 |

FOREIGN PATENT DOCUMENTS

| | | | |
|---|---|---|---|
| WO | 93/15199 | 8/1993 | |
| WO | 93/15200 | 8/1993 | |
| WO | 2006/031291 | 3/2006 | |
| WO | WO-2014011819 A2 * | 1/2014 | ............. A61K 38/36 |

OTHER PUBLICATIONS

Gupta, Glucagon-like peptide-1 analogues: An overview, Indian Journal of Endocrinology and Metabolism, 2013, 17, pp. 413-421.*
Sutradhar et al, Distribution and elimination of protein therapeutics: A review, S. J. Pharm. Sci., 2011, 4, pp. 1-12.*
Badirou et al., In Vivo Analysis of the Role of O-Glycosylations of Von Willebrand Factor, PLoS One, May 2012, vol. 7, Issue 5, e37508, pp. 1-11.
International Search Report and Written Opinion of the International Searching Authority, issued Jul. 21, 2017 in corresponding International Patent Application No. PCT/EP2017/059976.
Calo et al., "Enhancing the longevity and in vivo potency of therapeutic proteins: The power of CTP", Precision Medicine, 2:e989, pp. 1-8 (2015).

* cited by examiner

*Primary Examiner* — Li N Komatsu
(74) *Attorney, Agent, or Firm* — Wenderoth, Lind & Ponack, L.L.P.

(57) ABSTRACT

The invention relates to a fusion protein comprising a main protein and one or more extension peptides, wherein the amino acid sequence of the main protein is identical or similar to the amino acid sequence of a mammalian protein or a fragment thereof, and said extension peptide comprises a cluster of O-glycosylated amino acids. The extension peptide is identical to a non-repeated sequence of the mammalian protein and/or identical or similar to SEQ ID NO: 1. The main protein is preferably VWF. The fusion protein has an increased half life as compared to the main protein and may be used to increase the half-life of a binding partner, e.g. FVIII. The invention further relates to the complex formed by the fusion protein, a polynucleotide encoding the fusion protein as well as a vector and host cell comprising the polynucleotide.

28 Claims, 4 Drawing Sheets
Specification includes a Sequence Listing.

SEQUENCE LISTING

```
<160> NUMBER OF SEQ ID NOS: 22

<210> SEQ ID NO 1
<211> LENGTH: 31
<212> TYPE: PRT
<213> ORGANISM: Homo sapiens

<400> SEQUENCE: 1

Gln Glu Pro Gly Gly Leu Val Val Pro Pro Thr Asp Ala Pro Val Ser
1               5                   10                  15

Pro Thr Thr Leu Tyr Val Glu Asp Ile Ser Glu Pro Pro Leu His
            20                  25                  30

<210> SEQ ID NO 2
<211> LENGTH: 2813
<212> TYPE: PRT
<213> ORGANISM: Homo sapiens

<400> SEQUENCE: 2

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255
```

```
Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670
```

-continued

```
Ser Tyr Pro Asp Glu Glu Cys Asn Glu Ala Cys Leu Glu Gly Cys Phe
            675                 680                 685

Cys Pro Pro Gly Leu Tyr Met Asp Glu Arg Gly Asp Cys Val Pro Lys
690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
            755                 760                 765

Pro Pro Met Val Lys Leu Val Cys Pro Ala Asp Asn Leu Arg Ala Glu
770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
            835                 840                 845

Cys Val Cys Arg Asp Arg Lys Trp Asn Cys Thr Asp His Val Cys Asp
            850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
            915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
            995                 1000                1005

Ser Ser  Asn Leu Gln Val Glu  Glu Asp Pro Val Asp  Phe Gly Asn
1010                1015                1020

Ser Trp  Lys Val Ser Ser Gln  Cys Ala Asp Thr Arg  Lys Val Pro
1025                1030                1035

Leu Asp  Ser Ser Pro Ala Thr  Cys His Asn Asn Ile  Met Lys Gln
1040                1045                1050

Thr Met  Val Asp Ser Ser Cys  Arg Ile Leu Thr Ser  Asp Val Phe
1055                1060                1065

Gln Asp  Cys Asn Lys Leu Val  Asp Pro Glu Pro Tyr  Leu Asp Val
1070                1075                1080

Cys Ile  Tyr Asp Thr Cys Ser  Cys Glu Ser Ile Gly  Asp Cys Ala
```

-continued

```
            1085                1090                1095
Cys Phe Cys Asp Thr Ile Ala Ala Tyr Ala His Val Cys Ala Gln
            1100                1105                1110
His Gly Lys Val Val Thr Trp Arg Thr Ala Thr Leu Cys Pro Gln
            1115                1120                1125
Ser Cys Glu Glu Arg Asn Leu Arg Glu Asn Gly Tyr Glu Cys Glu
            1130                1135                1140
Trp Arg Tyr Asn Ser Cys Ala Pro Ala Cys Gln Val Thr Cys Gln
            1145                1150                1155
His Pro Glu Pro Leu Ala Cys Pro Val Gln Cys Val Glu Gly Cys
            1160                1165                1170
His Ala His Cys Pro Pro Gly Lys Ile Leu Asp Glu Leu Leu Gln
            1175                1180                1185
Thr Cys Val Asp Pro Glu Asp Cys Pro Val Cys Glu Val Ala Gly
            1190                1195                1200
Arg Arg Phe Ala Ser Gly Lys Lys Val Thr Leu Asn Pro Ser Asp
            1205                1210                1215
Pro Glu His Cys Gln Ile Cys His Cys Asp Val Val Asn Leu Thr
            1220                1225                1230
Cys Glu Ala Cys Gln Glu Pro Gly Gly Leu Val Val Pro Pro Thr
            1235                1240                1245
Asp Ala Pro Val Ser Pro Thr Thr Leu Tyr Val Glu Asp Ile Ser
            1250                1255                1260
Glu Pro Pro Leu His Asp Phe Tyr Cys Ser Arg Leu Leu Asp Leu
            1265                1270                1275
Val Phe Leu Leu Asp Gly Ser Ser Arg Leu Ser Glu Ala Glu Phe
            1280                1285                1290
Glu Val Leu Lys Ala Phe Val Val Asp Met Met Glu Arg Leu Arg
            1295                1300                1305
Ile Ser Gln Lys Trp Val Arg Val Ala Val Val Glu Tyr His Asp
            1310                1315                1320
Gly Ser His Ala Tyr Ile Gly Leu Lys Asp Arg Lys Arg Pro Ser
            1325                1330                1335
Glu Leu Arg Arg Ile Ala Ser Gln Val Lys Tyr Ala Gly Ser Gln
            1340                1345                1350
Val Ala Ser Thr Ser Glu Val Leu Lys Tyr Thr Leu Phe Gln Ile
            1355                1360                1365
Phe Ser Lys Ile Asp Arg Pro Glu Ala Ser Arg Ile Thr Leu Leu
            1370                1375                1380
Leu Met Ala Ser Gln Glu Pro Gln Arg Met Ser Arg Asn Phe Val
            1385                1390                1395
Arg Tyr Val Gln Gly Leu Lys Lys Lys Lys Val Ile Val Ile Pro
            1400                1405                1410
Val Gly Ile Gly Pro His Ala Asn Leu Lys Gln Ile Arg Leu Ile
            1415                1420                1425
Glu Lys Gln Ala Pro Glu Asn Lys Ala Phe Val Leu Ser Ser Val
            1430                1435                1440
Asp Glu Leu Glu Gln Gln Arg Asp Glu Ile Val Ser Tyr Leu Cys
            1445                1450                1455
Asp Leu Ala Pro Glu Ala Pro Pro Pro Thr Leu Pro Pro Asp Met
            1460                1465                1470
Ala Gln Val Thr Val Gly Pro Gly Leu Leu Gly Val Ser Thr Leu
            1475                1480                1485
```

```
Gly Pro Lys Arg Asn Ser Met Val Leu Asp Val Ala Phe Val Leu
    1490                1495                1500

Glu Gly Ser Asp Lys Ile Gly Glu Ala Asp Phe Asn Arg Ser Lys
    1505                1510                1515

Glu Phe Met Glu Glu Val Ile Gln Arg Met Asp Val Gly Gln Asp
    1520                1525                1530

Ser Ile His Val Thr Val Leu Gln Tyr Ser Tyr Met Val Thr Val
    1535                1540                1545

Glu Tyr Pro Phe Ser Glu Ala Gln Ser Lys Gly Asp Ile Leu Gln
    1550                1555                1560

Arg Val Arg Glu Ile Arg Tyr Gln Gly Gly Asn Arg Thr Asn Thr
    1565                1570                1575

Gly Leu Ala Leu Arg Tyr Leu Ser Asp His Ser Phe Leu Val Ser
    1580                1585                1590

Gln Gly Asp Arg Glu Gln Ala Pro Asn Leu Val Tyr Met Val Thr
    1595                1600                1605

Gly Asn Pro Ala Ser Asp Glu Ile Lys Arg Leu Pro Gly Asp Ile
    1610                1615                1620

Gln Val Val Pro Ile Gly Val Gly Pro Asn Ala Asn Val Gln Glu
    1625                1630                1635

Leu Glu Arg Ile Gly Trp Pro Asn Ala Pro Ile Leu Ile Gln Asp
    1640                1645                1650

Phe Glu Thr Leu Pro Arg Glu Ala Pro Asp Leu Val Leu Gln Arg
    1655                1660                1665

Cys Cys Ser Gly Glu Gly Leu Gln Ile Pro Thr Leu Ser Pro Ala
    1670                1675                1680

Pro Asp Cys Ser Gln Pro Leu Asp Val Ile Leu Leu Leu Asp Gly
    1685                1690                1695

Ser Ser Ser Phe Pro Ala Ser Tyr Phe Asp Glu Met Lys Ser Phe
    1700                1705                1710

Ala Lys Ala Phe Ile Ser Lys Ala Asn Ile Gly Pro Arg Leu Thr
    1715                1720                1725

Gln Val Ser Val Leu Gln Tyr Gly Ser Ile Thr Thr Ile Asp Val
    1730                1735                1740

Pro Trp Asn Val Val Pro Glu Lys Ala His Leu Leu Ser Leu Val
    1745                1750                1755

Asp Val Met Gln Arg Glu Gly Gly Pro Ser Gln Ile Gly Asp Ala
    1760                1765                1770

Leu Gly Phe Ala Val Arg Tyr Leu Thr Ser Glu Met His Gly Ala
    1775                1780                1785

Arg Pro Gly Ala Ser Lys Ala Val Val Ile Leu Val Thr Asp Val
    1790                1795                1800

Ser Val Asp Ser Val Asp Ala Ala Asp Ala Ala Arg Ser Asn
    1805                1810                1815

Arg Val Thr Val Phe Pro Ile Gly Ile Gly Asp Arg Tyr Asp Ala
    1820                1825                1830

Ala Gln Leu Arg Ile Leu Ala Gly Pro Ala Gly Asp Ser Asn Val
    1835                1840                1845

Val Lys Leu Gln Arg Ile Glu Asp Leu Pro Thr Met Val Thr Leu
    1850                1855                1860

Gly Asn Ser Phe Leu His Lys Leu Cys Ser Gly Phe Val Arg Ile
    1865                1870                1875
```

```
Cys Met Asp Glu Asp Gly Asn Glu Lys Arg Pro Gly Asp Val Trp
    1880                1885                1890

Thr Leu Pro Asp Gln Cys His Thr Val Thr Cys Gln Pro Asp Gly
    1895                1900                1905

Gln Thr Leu Leu Lys Ser His Arg Val Asn Cys Asp Arg Gly Leu
    1910                1915                1920

Arg Pro Ser Cys Pro Asn Ser Gln Ser Pro Val Lys Val Glu Glu
    1925                1930                1935

Thr Cys Gly Cys Arg Trp Thr Cys Pro Cys Val Cys Thr Gly Ser
    1940                1945                1950

Ser Thr Arg His Ile Val Thr Phe Asp Gly Gln Asn Phe Lys Leu
    1955                1960                1965

Thr Gly Ser Cys Ser Tyr Val Leu Phe Gln Asn Lys Glu Gln Asp
    1970                1975                1980

Leu Glu Val Ile Leu His Asn Gly Ala Cys Ser Pro Gly Ala Arg
    1985                1990                1995

Gln Gly Cys Met Lys Ser Ile Glu Val Lys His Ser Ala Leu Ser
    2000                2005                2010

Val Glu Leu His Ser Asp Met Glu Val Thr Val Asn Gly Arg Leu
    2015                2020                2025

Val Ser Val Pro Tyr Val Gly Gly Asn Met Glu Val Asn Val Tyr
    2030                2035                2040

Gly Ala Ile Met His Glu Val Arg Phe Asn His Leu Gly His Ile
    2045                2050                2055

Phe Thr Phe Thr Pro Gln Asn Asn Glu Phe Gln Leu Gln Leu Ser
    2060                2065                2070

Pro Lys Thr Phe Ala Ser Lys Thr Tyr Gly Leu Cys Gly Ile Cys
    2075                2080                2085

Asp Glu Asn Gly Ala Asn Asp Phe Met Leu Arg Asp Gly Thr Val
    2090                2095                2100

Thr Thr Asp Trp Lys Thr Leu Val Gln Glu Trp Thr Val Gln Arg
    2105                2110                2115

Pro Gly Gln Thr Cys Gln Pro Ile Leu Glu Glu Gln Cys Leu Val
    2120                2125                2130

Pro Asp Ser Ser His Cys Gln Val Leu Leu Leu Pro Leu Phe Ala
    2135                2140                2145

Glu Cys His Lys Val Leu Ala Pro Ala Thr Phe Tyr Ala Ile Cys
    2150                2155                2160

Gln Gln Asp Ser Cys His Gln Glu Gln Val Cys Glu Val Ile Ala
    2165                2170                2175

Ser Tyr Ala His Leu Cys Arg Thr Asn Gly Val Cys Val Asp Trp
    2180                2185                2190

Arg Thr Pro Asp Phe Cys Ala Met Ser Cys Pro Pro Ser Leu Val
    2195                2200                2205

Tyr Asn His Cys Glu His Gly Cys Pro Arg His Cys Asp Gly Asn
    2210                2215                2220

Val Ser Ser Cys Gly Asp His Pro Ser Glu Gly Cys Phe Cys Pro
    2225                2230                2235

Pro Asp Lys Val Met Leu Glu Gly Ser Cys Val Pro Glu Glu Ala
    2240                2245                2250

Cys Thr Gln Cys Ile Gly Glu Asp Gly Val Gln His Gln Phe Leu
    2255                2260                2265

Glu Ala Trp Val Pro Asp His Gln Pro Cys Gln Ile Cys Thr Cys
```

-continued

```
                2270                2275                2280
Leu Ser Gly Arg Lys Val Asn Cys Thr Thr Gln Pro Cys Pro Thr
        2285                2290                2295

Ala Lys Ala Pro Thr Cys Gly Leu Cys Glu Val Ala Arg Leu Arg
        2300                2305                2310

Gln Asn Ala Asp Gln Cys Cys Pro Glu Tyr Glu Cys Val Cys Asp
        2315                2320                2325

Pro Val Ser Cys Asp Leu Pro Pro Val Pro His Cys Glu Arg Gly
        2330                2335                2340

Leu Gln Pro Thr Leu Thr Asn Pro Gly Glu Cys Arg Pro Asn Phe
        2345                2350                2355

Thr Cys Ala Cys Arg Lys Glu Glu Cys Lys Arg Val Ser Pro Pro
        2360                2365                2370

Ser Cys Pro Pro His Arg Leu Pro Thr Leu Arg Lys Thr Gln Cys
        2375                2380                2385

Cys Asp Glu Tyr Glu Cys Ala Cys Asn Cys Val Asn Ser Thr Val
        2390                2395                2400

Ser Cys Pro Leu Gly Tyr Leu Ala Ser Thr Ala Thr Asn Asp Cys
        2405                2410                2415

Gly Cys Thr Thr Thr Thr Cys Leu Pro Asp Lys Val Cys Val His
        2420                2425                2430

Arg Ser Thr Ile Tyr Pro Val Gly Gln Phe Trp Glu Glu Gly Cys
        2435                2440                2445

Asp Val Cys Thr Cys Thr Asp Met Glu Asp Ala Val Met Gly Leu
        2450                2455                2460

Arg Val Ala Gln Cys Ser Gln Lys Pro Cys Glu Asp Ser Cys Arg
        2465                2470                2475

Ser Gly Phe Thr Tyr Val Leu His Glu Gly Glu Cys Cys Gly Arg
        2480                2485                2490

Cys Leu Pro Ser Ala Cys Glu Val Val Thr Gly Ser Pro Arg Gly
        2495                2500                2505

Asp Ser Gln Ser Ser Trp Lys Ser Val Gly Ser Gln Trp Ala Ser
        2510                2515                2520

Pro Glu Asn Pro Cys Leu Ile Asn Glu Cys Val Arg Val Lys Glu
        2525                2530                2535

Glu Val Phe Ile Gln Gln Arg Asn Val Ser Cys Pro Gln Leu Glu
        2540                2545                2550

Val Pro Val Cys Pro Ser Gly Phe Gln Leu Ser Cys Lys Thr Ser
        2555                2560                2565

Ala Cys Cys Pro Ser Cys Arg Cys Glu Arg Met Glu Ala Cys Met
        2570                2575                2580

Leu Asn Gly Thr Val Ile Gly Pro Gly Lys Thr Val Met Ile Asp
        2585                2590                2595

Val Cys Thr Thr Cys Arg Cys Met Val Gln Val Gly Val Ile Ser
        2600                2605                2610

Gly Phe Lys Leu Glu Cys Arg Lys Thr Thr Cys Asn Pro Cys Pro
        2615                2620                2625

Leu Gly Tyr Lys Glu Glu Asn Asn Thr Gly Glu Cys Cys Gly Arg
        2630                2635                2640

Cys Leu Pro Thr Ala Cys Thr Ile Gln Leu Arg Gly Gly Gln Ile
        2645                2650                2655

Met Thr Leu Lys Arg Asp Glu Thr Leu Gln Asp Gly Cys Asp Thr
        2660                2665                2670
```

-continued

```
His Phe Cys Lys Val Asn Glu Arg Gly Glu Tyr Phe Trp Glu Lys
    2675                2680                2685

Arg Val Thr Gly Cys Pro Pro Phe Asp Glu His Lys Cys Leu Ala
    2690                2695                2700

Glu Gly Gly Lys Ile Met Lys Ile Pro Gly Thr Cys Cys Asp Thr
    2705                2710                2715

Cys Glu Glu Pro Glu Cys Asn Asp Ile Thr Ala Arg Leu Gln Tyr
    2720                2725                2730

Val Lys Val Gly Ser Cys Lys Ser Glu Val Glu Val Asp Ile His
    2735                2740                2745

Tyr Cys Gln Gly Lys Cys Ala Ser Lys Ala Met Tyr Ser Ile Asp
    2750                2755                2760

Ile Asn Asp Val Gln Asp Gln Cys Ser Cys Cys Ser Pro Thr Arg
    2765                2770                2775

Thr Glu Pro Met Gln Val Ala Leu His Cys Thr Asn Gly Ser Val
    2780                2785                2790

Val Tyr His Glu Val Leu Asn Ala Met Glu Cys Lys Cys Ser Pro
    2795                2800                2805

Arg Lys Cys Ser Lys
    2810

<210> SEQ ID NO 3
<211> LENGTH: 567
<212> TYPE: PRT
<213> ORGANISM: Homo sapiens

<400> SEQUENCE: 3

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
                20                  25                  30

Asp Leu Glu Cys Met Ser Met Gly Cys Val Ser Gly Cys Leu Cys Pro
            35                  40                  45

Pro Gly Met Val Arg His Glu Asn Arg Cys Val Ala Leu Glu Arg Cys
        50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
```

```
            210                 215                 220
Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
            245                 250                 255

Asp Phe Gly Asn Ser Trp Lys Val Ser Ser Gln Cys Ala Asp Thr Arg
                260                 265                 270

Lys Val Pro Leu Asp Ser Ser Pro Ala Thr Cys His Asn Asn Ile Met
            275                 280                 285

Lys Gln Thr Met Val Asp Ser Ser Cys Arg Ile Leu Thr Ser Asp Val
        290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
                485                 490                 495

Glu Asp Ile Ser Glu Pro Pro Leu His Gln Glu Pro Gly Gly Leu Val
            500                 505                 510

Val Pro Pro Thr Asp Ala Pro Val Ser Pro Thr Thr Leu Tyr Val Glu
        515                 520                 525

Asp Ile Ser Glu Pro Pro Leu His Gln Glu Pro Gly Gly Leu Val Val
530                 535                 540

Pro Pro Thr Asp Ala Pro Val Ser Pro Thr Thr Leu Tyr Val Glu Asp
545                 550                 555                 560

Ile Ser Glu Pro Pro Leu His
                565

<210> SEQ ID NO 4
<211> LENGTH: 589
<212> TYPE: PRT
<213> ORGANISM: Homo sapiens

<400> SEQUENCE: 4

Met Ile Pro Ala Arg Phe Ala Gly Val Leu Leu Ala Leu Ala Leu Ile
1               5                   10                  15
```

-continued

```
Leu Pro Gly Thr Leu Cys Ser Leu Ser Cys Arg Pro Met Val Lys
             20                  25                  30

Leu Val Cys Pro Ala Asp Asn Leu Arg Ala Glu Gly Leu Glu Cys Thr
         35                  40                  45

Lys Thr Cys Gln Asn Tyr Asp Leu Glu Cys Met Ser Met Gly Cys Val
     50                  55                  60

Ser Gly Cys Leu Cys Pro Pro Gly Met Val Arg His Glu Asn Arg Cys
 65                  70                  75                  80

Val Ala Leu Glu Arg Cys Pro Cys Phe His Gln Gly Lys Glu Tyr Ala
                 85                  90                  95

Pro Gly Glu Thr Val Lys Ile Gly Cys Asn Thr Cys Val Cys Gln Asp
             100                 105                 110

Arg Lys Trp Asn Cys Thr Asp His Val Cys Asp Ala Thr Cys Ser Thr
         115                 120                 125

Ile Gly Met Ala His Tyr Leu Thr Phe Asp Gly Leu Lys Tyr Leu Phe
    130                 135                 140

Pro Gly Glu Cys Gln Tyr Val Leu Val Gln Asp Tyr Cys Gly Ser Asn
145                 150                 155                 160

Pro Gly Thr Phe Arg Ile Leu Val Gly Asn Lys Gly Cys Ser His Pro
                165                 170                 175

Ser Val Lys Cys Lys Lys Arg Val Thr Ile Leu Val Glu Gly Gly Glu
            180                 185                 190

Ile Glu Leu Phe Asp Gly Glu Val Asn Val Lys Arg Pro Met Lys Asp
        195                 200                 205

Glu Thr His Phe Glu Val Val Glu Ser Gly Arg Tyr Ile Ile Leu Leu
    210                 215                 220

Leu Gly Lys Ala Leu Ser Val Val Trp Asp Arg His Leu Ser Ile Ser
225                 230                 235                 240

Val Val Leu Lys Gln Thr Tyr Gln Glu Lys Val Cys Gly Leu Cys Gly
                245                 250                 255

Asn Phe Asp Gly Ile Gln Asn Asn Asp Leu Thr Ser Ser Asn Leu Gln
            260                 265                 270

Val Glu Glu Asp Pro Val Asp Phe Gly Asn Ser Trp Lys Val Ser Ser
        275                 280                 285

Gln Cys Ala Asp Thr Arg Lys Val Pro Leu Asp Ser Ser Pro Ala Thr
    290                 295                 300

Cys His Asn Asn Ile Met Lys Gln Thr Met Val Asp Ser Ser Cys Arg
305                 310                 315                 320

Ile Leu Thr Ser Asp Val Phe Gln Asp Cys Asn Lys Leu Val Asp Pro
                325                 330                 335

Glu Pro Tyr Leu Asp Val Cys Ile Tyr Asp Thr Cys Ser Cys Glu Ser
            340                 345                 350

Ile Gly Asp Cys Ala Cys Phe Cys Asp Thr Ile Ala Ala Tyr Ala His
        355                 360                 365

Val Cys Ala Gln His Gly Lys Val Val Thr Trp Arg Thr Ala Thr Leu
    370                 375                 380

Cys Pro Gln Ser Cys Glu Glu Arg Asn Leu Arg Glu Asn Gly Tyr Glu
385                 390                 395                 400

Cys Glu Trp Arg Tyr Asn Ser Cys Ala Pro Ala Cys Gln Val Thr Cys
                405                 410                 415

Gln His Pro Glu Pro Leu Ala Cys Pro Val Gln Cys Val Glu Gly Cys
            420                 425                 430

His Ala His Cys Pro Pro Gly Lys Ile Leu Asp Glu Leu Leu Gln Thr
```

```
                435                 440                 445
Cys Val Asp Pro Glu Asp Cys Pro Val Cys Glu Val Ala Gly Arg Arg
    450                 455                 460

Phe Ala Ser Gly Lys Lys Val Thr Leu Asn Pro Ser Asp Pro Glu His
465                 470                 475                 480

Cys Gln Ile Cys His Cys Asp Val Val Asn Leu Thr Cys Glu Ala Cys
                485                 490                 495

Gln Glu Pro Gly Gly Leu Val Val Pro Pro Thr Asp Ala Pro Val Ser
            500                 505                 510

Pro Thr Thr Leu Tyr Val Glu Asp Ile Ser Glu Pro Pro Leu His Gln
        515                 520                 525

Glu Pro Gly Gly Leu Val Val Pro Pro Thr Asp Ala Pro Val Ser Pro
    530                 535                 540

Thr Thr Leu Tyr Val Glu Asp Ile Ser Glu Pro Pro Leu His Gln Glu
545                 550                 555                 560

Pro Gly Gly Leu Val Val Pro Pro Thr Asp Ala Pro Val Ser Pro Thr
                565                 570                 575

Thr Leu Tyr Val Glu Asp Ile Ser Glu Pro Pro Leu His
            580                 585

<210> SEQ ID NO 5
<211> LENGTH: 1330
<212> TYPE: PRT
<213> ORGANISM: Homo sapiens

<400> SEQUENCE: 5

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220
```

```
Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
            245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
            325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
            405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
            485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
            565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
```

-continued

```
                645                 650                 655
Val Tyr Leu Gln Cys Gly Thr Pro Cys Asn Leu Thr Cys Arg Ser Leu
                660                 665                 670

Ser Tyr Pro Asp Glu Glu Cys Asn Glu Ala Cys Leu Glu Gly Cys Phe
                675                 680                 685

Cys Pro Pro Gly Leu Tyr Met Asp Glu Arg Gly Asp Cys Val Pro Lys
                690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
                740                 745                 750

Leu Ser Ser Pro Leu Ser His Arg Ser Lys Arg Ser Leu Ser Cys Arg
                755                 760                 765

Pro Pro Met Val Lys Leu Val Cys Pro Ala Asp Asn Leu Arg Ala Glu
                770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
                820                 825                 830

Gly Lys Glu Tyr Ala Pro Gly Glu Thr Val Lys Ile Gly Cys Asn Thr
                835                 840                 845

Cys Val Cys Gln Asp Arg Lys Trp Asn Cys Thr Asp His Val Cys Asp
850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
                900                 905                 910

Gly Cys Ser His Pro Ser Val Lys Cys Lys Lys Arg Val Thr Ile Leu
                915                 920                 925

Val Glu Gly Gly Glu Ile Glu Leu Phe Asp Gly Glu Val Asn Val Lys
                930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
                980                 985                 990

Cys Gly Leu Cys Gly Asn Phe Asp  Gly Ile Gln Asn Asn  Asp Leu Thr
                995                 1000                1005

Ser Ser  Asn Leu Gln Val Glu  Glu Asp Pro Val Asp  Phe Gly Asn
    1010                1015                1020

Ser Trp  Lys Val Ser Ser Gln  Cys Ala Asp Thr Arg  Lys Val Pro
    1025                1030                1035

Leu Asp  Ser Ser Pro Ala Thr  Cys His Asn Asn Ile  Met Lys Gln
    1040                1045                1050

Thr Met  Val Asp Ser Ser Cys  Arg Ile Leu Thr Ser  Asp Val Phe
    1055                1060                1065
```

-continued

Gln Asp Cys Asn Lys Leu Val Asp Pro Glu Pro Tyr Leu Asp Val
    1070                1075                1080

Cys Ile Tyr Asp Thr Cys Ser Cys Glu Ser Ile Gly Asp Cys Ala
1085                1090                1095

Cys Phe Cys Asp Thr Ile Ala Ala Tyr Ala His Val Cys Ala Gln
1100                1105                1110

His Gly Lys Val Val Thr Trp Arg Thr Ala Thr Leu Cys Pro Gln
1115                1120                1125

Ser Cys Glu Glu Arg Asn Leu Arg Glu Asn Gly Tyr Glu Cys Glu
1130                1135                1140

Trp Arg Tyr Asn Ser Cys Ala Pro Ala Cys Gln Val Thr Cys Gln
1145                1150                1155

His Pro Glu Pro Leu Ala Cys Pro Val Gln Cys Val Glu Gly Cys
1160                1165                1170

His Ala His Cys Pro Pro Gly Lys Ile Leu Asp Glu Leu Leu Gln
1175                1180                1185

Thr Cys Val Asp Pro Glu Asp Cys Pro Val Cys Glu Val Ala Gly
1190                1195                1200

Arg Arg Phe Ala Ser Gly Lys Lys Val Thr Leu Asn Pro Ser Asp
1205                1210                1215

Pro Glu His Cys Gln Ile Cys His Cys Asp Val Val Asn Leu Thr
1220                1225                1230

Cys Glu Ala Cys Gln Glu Pro Gly Gly Leu Val Val Pro Pro Thr
1235                1240                1245

Asp Ala Pro Val Ser Pro Thr Thr Leu Tyr Val Glu Asp Ile Ser
1250                1255                1260

Glu Pro Pro Leu His Gln Glu Pro Gly Gly Leu Val Val Pro Pro
1265                1270                1275

Thr Asp Ala Pro Val Ser Pro Thr Thr Leu Tyr Val Glu Asp Ile
1280                1285                1290

Ser Glu Pro Pro Leu His Gln Glu Pro Gly Gly Leu Val Val Pro
1295                1300                1305

Pro Thr Asp Ala Pro Val Ser Pro Thr Thr Leu Tyr Val Glu Asp
1310                1315                1320

Ile Ser Glu Pro Pro Leu His
1325                1330

<210> SEQ ID NO 6
<211> LENGTH: 629
<212> TYPE: PRT
<213> ORGANISM: Homo sapiens

<400> SEQUENCE: 6

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
                20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr

```
                    85                  90                  95
Asp His Val Cys Asp Ala Thr Cys Ser Thr Ile Gly Met Ala His Tyr
                100                 105                 110

Leu Thr Phe Asp Gly Leu Lys Tyr Leu Phe Pro Gly Glu Cys Gln Tyr
            115                 120                 125

Val Leu Val Gln Asp Tyr Cys Gly Ser Asn Pro Gly Thr Phe Arg Ile
        130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
                180                 185                 190

Val Glu Ser Gly Arg Tyr Ile Ile Leu Leu Gly Lys Ala Leu Ser
                195                 200                 205

Val Val Trp Asp Arg His Leu Ser Ile Ser Val Val Leu Lys Gln Thr
        210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
                260                 265                 270

Lys Val Pro Leu Asp Ser Ser Pro Ala Thr Cys His Asn Asn Ile Met
            275                 280                 285

Lys Gln Thr Met Val Asp Ser Ser Cys Arg Ile Leu Thr Ser Asp Val
        290                 295                 300

Phe Gln Asp Cys Asn Lys Leu Val Asp Pro Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
                485                 490                 495

Glu Asp Ile Ser Glu Pro Pro Leu His Gln Glu Pro Gly Gly Leu Val
            500                 505                 510
```

```
Val Pro Pro Thr Asp Ala Pro Val Ser Pro Thr Thr Leu Tyr Val Glu
        515                 520                 525

Asp Ile Ser Glu Pro Pro Leu His Gln Glu Pro Gly Gly Leu Val Val
    530                 535                 540

Pro Pro Thr Asp Ala Pro Val Ser Pro Thr Thr Leu Tyr Val Glu Asp
545                 550                 555                 560

Ile Ser Glu Pro Pro Leu His Gln Glu Pro Gly Gly Leu Val Val Pro
                565                 570                 575

Pro Thr Asp Ala Pro Val Ser Pro Thr Thr Leu Tyr Val Glu Asp Ile
            580                 585                 590

Ser Glu Pro Pro Leu His Gln Glu Pro Gly Gly Leu Val Val Pro Pro
        595                 600                 605

Thr Asp Ala Pro Val Ser Pro Thr Thr Leu Tyr Val Glu Asp Ile Ser
    610                 615                 620

Glu Pro Pro Leu His
625

<210> SEQ ID NO 7
<211> LENGTH: 651
<212> TYPE: PRT
<213> ORGANISM: Homo sapiens

<400> SEQUENCE: 7

Met Ile Pro Ala Arg Phe Ala Gly Val Leu Leu Ala Leu Ala Leu Ile
1               5                   10                  15

Leu Pro Gly Thr Leu Cys Ser Leu Ser Cys Arg Pro Pro Met Val Lys
            20                  25                  30

Leu Val Cys Pro Ala Asp Asn Leu Arg Ala Glu Gly Leu Glu Cys Thr
        35                  40                  45

Lys Thr Cys Gln Asn Tyr Asp Leu Glu Cys Met Ser Met Gly Cys Val
    50                  55                  60

Ser Gly Cys Leu Cys Pro Pro Gly Met Val Arg His Glu Asn Arg Cys
65                  70                  75                  80

Val Ala Leu Glu Arg Cys Pro Cys Phe His Gln Gly Lys Glu Tyr Ala
                85                  90                  95

Pro Gly Glu Thr Val Lys Ile Gly Cys Asn Thr Cys Val Cys Gln Asp
            100                 105                 110

Arg Lys Trp Asn Cys Thr Asp His Val Cys Asp Ala Thr Cys Ser Thr
        115                 120                 125

Ile Gly Met Ala His Tyr Leu Thr Phe Asp Gly Leu Lys Tyr Leu Phe
    130                 135                 140

Pro Gly Glu Cys Gln Tyr Val Leu Val Gln Asp Tyr Cys Gly Ser Asn
145                 150                 155                 160

Pro Gly Thr Phe Arg Ile Leu Val Gly Asn Lys Gly Cys Ser His Pro
                165                 170                 175

Ser Val Lys Cys Lys Lys Arg Val Thr Ile Leu Val Glu Gly Gly Glu
            180                 185                 190

Ile Glu Leu Phe Asp Gly Glu Val Asn Val Lys Arg Pro Met Lys Asp
        195                 200                 205

Glu Thr His Phe Glu Val Val Glu Ser Gly Arg Tyr Ile Ile Leu Leu
    210                 215                 220

Leu Gly Lys Ala Leu Ser Val Val Trp Asp Arg His Leu Ser Ile Ser
225                 230                 235                 240

Val Val Leu Lys Gln Thr Tyr Gln Glu Lys Val Cys Gly Leu Cys Gly
```

```
                         245                 250                 255
Asn Phe Asp Gly Ile Gln Asn Asn Asp Leu Thr Ser Ser Asn Leu Gln
                260                 265                 270

Val Glu Glu Asp Pro Val Asp Phe Gly Asn Ser Trp Lys Val Ser Ser
            275                 280                 285

Gln Cys Ala Asp Thr Arg Lys Val Pro Leu Asp Ser Ser Pro Ala Thr
        290                 295                 300

Cys His Asn Asn Ile Met Lys Gln Thr Met Val Asp Ser Ser Cys Arg
305                 310                 315                 320

Ile Leu Thr Ser Asp Val Phe Gln Asp Cys Asn Lys Leu Val Asp Pro
                325                 330                 335

Glu Pro Tyr Leu Asp Val Cys Ile Tyr Asp Thr Cys Ser Cys Glu Ser
            340                 345                 350

Ile Gly Asp Cys Ala Cys Phe Cys Asp Thr Ile Ala Ala Tyr Ala His
        355                 360                 365

Val Cys Ala Gln His Gly Lys Val Val Thr Trp Arg Thr Ala Thr Leu
    370                 375                 380

Cys Pro Gln Ser Cys Glu Glu Arg Asn Leu Arg Glu Asn Gly Tyr Glu
385                 390                 395                 400

Cys Glu Trp Arg Tyr Asn Ser Cys Ala Pro Ala Cys Gln Val Thr Cys
                405                 410                 415

Gln His Pro Glu Pro Leu Ala Cys Pro Val Gln Cys Val Glu Gly Cys
            420                 425                 430

His Ala His Cys Pro Pro Gly Lys Ile Leu Asp Glu Leu Leu Gln Thr
        435                 440                 445

Cys Val Asp Pro Glu Asp Cys Pro Val Cys Glu Val Ala Gly Arg Arg
    450                 455                 460

Phe Ala Ser Gly Lys Lys Val Thr Leu Asn Pro Ser Asp Pro Glu His
465                 470                 475                 480

Cys Gln Ile Cys His Cys Asp Val Val Asn Leu Thr Cys Glu Ala Cys
                485                 490                 495

Gln Glu Pro Gly Gly Leu Val Val Pro Pro Thr Asp Ala Pro Val Ser
            500                 505                 510

Pro Thr Thr Leu Tyr Val Glu Asp Ile Ser Glu Pro Pro Leu His Gln
        515                 520                 525

Glu Pro Gly Gly Leu Val Val Pro Pro Thr Asp Ala Pro Val Ser Pro
    530                 535                 540

Thr Thr Leu Tyr Val Glu Asp Ile Ser Glu Pro Pro Leu His Gln Glu
545                 550                 555                 560

Pro Gly Gly Leu Val Val Pro Pro Thr Asp Ala Pro Val Ser Pro Thr
                565                 570                 575

Thr Leu Tyr Val Glu Asp Ile Ser Glu Pro Pro Leu His Gln Glu Pro
            580                 585                 590

Gly Gly Leu Val Val Pro Pro Thr Asp Ala Pro Val Ser Pro Thr Thr
        595                 600                 605

Leu Tyr Val Glu Asp Ile Ser Glu Pro Pro Leu His Gln Glu Pro Gly
    610                 615                 620

Gly Leu Val Val Pro Pro Thr Asp Ala Pro Val Ser Pro Thr Thr Leu
625                 630                 635                 640

Tyr Val Glu Asp Ile Ser Glu Pro Pro Leu His
                645                 650

<210> SEQ ID NO 8
```

```
<211> LENGTH: 1392
<212> TYPE: PRT
<213> ORGANISM: Homo sapiens

<400> SEQUENCE: 8

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
                20                  25                  30

Ala Arg Cys Ser Leu Phe Gly Ser Asp Phe Val Asn Thr Phe Asp Gly
            35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
```

```
                385                 390                 395                 400
Asn Arg Tyr Phe Thr Phe Ser Gly Ile Cys Gln Tyr Leu Leu Ala Arg
                    405                 410                 415
Asp Cys Gln Asp His Ser Phe Ser Ile Val Ile Glu Thr Val Gln Cys
                    420                 425                 430
Ala Asp Asp Arg Asp Ala Val Cys Thr Arg Ser Val Thr Val Arg Leu
                    435                 440                 445
Pro Gly Leu His Asn Ser Leu Val Lys Leu Lys His Gly Ala Gly Val
                    450                 455                 460
Ala Met Asp Gly Gln Asp Val Gln Leu Pro Leu Leu Lys Gly Asp Leu
465                 470                 475                 480
Arg Ile Gln His Thr Val Thr Ala Ser Val Arg Leu Ser Tyr Gly Glu
                    485                 490                 495
Asp Leu Gln Met Asp Trp Asp Gly Arg Gly Arg Leu Leu Val Lys Leu
                    500                 505                 510
Ser Pro Val Tyr Ala Gly Lys Thr Cys Gly Leu Cys Gly Asn Tyr Asn
                    515                 520                 525
Gly Asn Gln Gly Asp Asp Phe Leu Thr Pro Ser Gly Leu Ala Glu Pro
        530                 535                 540
Arg Val Glu Asp Phe Gly Asn Ala Trp Lys Leu His Gly Asp Cys Gln
545                 550                 555                 560
Asp Leu Gln Lys Gln His Ser Asp Pro Cys Ala Leu Asn Pro Arg Met
                    565                 570                 575
Thr Arg Phe Ser Glu Glu Ala Cys Ala Val Leu Thr Ser Pro Thr Phe
                    580                 585                 590
Glu Ala Cys His Arg Ala Val Ser Pro Leu Pro Tyr Leu Arg Asn Cys
                    595                 600                 605
Arg Tyr Asp Val Cys Ser Cys Ser Asp Gly Arg Glu Cys Leu Cys Gly
        610                 615                 620
Ala Leu Ala Ser Tyr Ala Ala Ala Cys Ala Gly Arg Gly Val Arg Val
625                 630                 635                 640
Ala Trp Arg Glu Pro Gly Arg Cys Glu Leu Asn Cys Pro Lys Gly Gln
                    645                 650                 655
Val Tyr Leu Gln Cys Gly Thr Pro Cys Asn Leu Thr Cys Arg Ser Leu
                    660                 665                 670
Ser Tyr Pro Asp Glu Glu Cys Asn Glu Ala Cys Leu Glu Gly Cys Phe
                    675                 680                 685
Cys Pro Pro Gly Leu Tyr Met Asp Glu Arg Gly Asp Cys Val Pro Lys
        690                 695                 700
Ala Gln Cys Pro Cys Tyr Tyr Asp Gly Glu Ile Phe Gln Pro Glu Asp
705                 710                 715                 720
Ile Phe Ser Asp His His Thr Met Cys Tyr Cys Glu Asp Gly Phe Met
                    725                 730                 735
His Cys Thr Met Ser Gly Val Pro Gly Ser Leu Leu Pro Asp Ala Val
                    740                 745                 750
Leu Ser Ser Pro Leu Ser His Arg Ser Lys Arg Ser Leu Ser Cys Arg
            755                 760                 765
Pro Pro Met Val Lys Leu Val Cys Pro Ala Asp Asn Leu Arg Ala Glu
        770                 775                 780
Gly Leu Glu Cys Thr Lys Thr Cys Gln Asn Tyr Asp Leu Glu Cys Met
785                 790                 795                 800
Ser Met Gly Cys Val Ser Gly Cys Leu Cys Pro Pro Gly Met Val Arg
                    805                 810                 815
```

```
His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
            835                 840                 845

Cys Val Cys Gln Asp Arg Lys Trp Asn Cys Thr Asp His Val Cys Asp
        850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Arg Val Thr Ile Leu
            915                 920                 925

Val Glu Gly Gly Glu Ile Glu Leu Phe Asp Gly Glu Val Asn Val Lys
            930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
                980                 985                 990

Cys Gly Leu Cys Gly Asn Phe Asp  Gly Ile Gln Asn Asn  Asp Leu Thr
            995                1000                1005

Ser Ser  Asn Leu Gln Val Glu  Asp Pro Val Asp  Phe Gly Asn
        1010                1015                1020

Ser Trp  Lys Val Ser Ser Gln  Cys Ala Asp Thr Arg  Lys Val Pro
        1025                1030                1035

Leu Asp  Ser Ser Pro Ala Thr  Cys His Asn Asn Ile  Met Lys Gln
        1040                1045                1050

Thr Met  Val Asp Ser Ser Cys  Arg Ile Leu Thr Ser  Asp Val Phe
        1055                1060                1065

Gln Asp  Cys Asn Lys Leu Val  Asp Pro Glu Pro Tyr  Leu Asp Val
        1070                1075                1080

Cys Ile  Tyr Asp Thr Cys Ser  Cys Glu Ser Ile Gly  Asp Cys Ala
        1085                1090                1095

Cys Phe  Cys Asp Thr Ile Ala  Ala Tyr Ala His Val  Cys Ala Gln
        1100                1105                1110

His Gly  Lys Val Val Thr Trp  Arg Thr Ala Thr Leu  Cys Pro Gln
        1115                1120                1125

Ser Cys  Glu Glu Arg Asn Leu  Arg Glu Asn Gly Tyr  Glu Cys Glu
        1130                1135                1140

Trp Arg  Tyr Asn Ser Cys Ala  Pro Ala Cys Gln Val  Thr Cys Gln
        1145                1150                1155

His Pro  Glu Pro Leu Ala Cys  Pro Val Gln Cys Val  Glu Gly Cys
        1160                1165                1170

His Ala  His Cys Pro Pro Gly  Lys Ile Leu Asp Glu  Leu Leu Gln
        1175                1180                1185

Thr Cys  Val Asp Pro Glu Asp  Cys Pro Val Cys Glu  Val Ala Gly
        1190                1195                1200

Arg Arg  Phe Ala Ser Gly Lys  Lys Val Thr Leu Asn  Pro Ser Asp
        1205                1210                1215
```

Pro Glu His Cys Gln Ile Cys His Cys Asp Val Val Asn Leu Thr
    1220                1225                1230

Cys Glu Ala Cys Gln Glu Pro Gly Gly Leu Val Val Pro Pro Thr
    1235                1240                1245

Asp Ala Pro Val Ser Pro Thr Thr Leu Tyr Val Glu Asp Ile Ser
    1250                1255                1260

Glu Pro Pro Leu His Gln Glu Pro Gly Gly Leu Val Val Pro Pro
    1265                1270                1275

Thr Asp Ala Pro Val Ser Pro Thr Thr Leu Tyr Val Glu Asp Ile
    1280                1285                1290

Ser Glu Pro Pro Leu His Gln Glu Pro Gly Gly Leu Val Val Pro
    1295                1300                1305

Pro Thr Asp Ala Pro Val Ser Pro Thr Thr Leu Tyr Val Glu Asp
    1310                1315                1320

Ile Ser Glu Pro Pro Leu His Gln Glu Pro Gly Gly Leu Val Val
    1325                1330                1335

Pro Pro Thr Asp Ala Pro Val Ser Pro Thr Thr Leu Tyr Val Glu
    1340                1345                1350

Asp Ile Ser Glu Pro Pro Leu His Gln Glu Pro Gly Gly Leu Val
    1355                1360                1365

Val Pro Pro Thr Asp Ala Pro Val Ser Pro Thr Thr Leu Tyr Val
    1370                1375                1380

Glu Asp Ile Ser Glu Pro Pro Leu His
    1385                1390

<210> SEQ ID NO 9
<211> LENGTH: 661
<212> TYPE: PRT
<213> ORGANISM: Homo sapiens

<400> SEQUENCE: 9

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
                20                  25                  30

Asp Leu Glu Cys Met Ser Met Gly Cys Val Ser Gly Cys Leu Cys Pro
            35                  40                  45

Pro Gly Met Val Arg His Glu Asn Arg Cys Val Ala Leu Glu Arg Cys
        50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Gln Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

```
Val Glu Ser Gly Arg Tyr Ile Ile Leu Leu Gly Lys Ala Leu Ser
    195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
            245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
            275                 280                 285

Lys Gln Thr Met Val Asp Ser Ser Cys Arg Ile Leu Thr Ser Asp Val
            290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
            355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
            435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
            485                 490                 495

Glu Asp Ile Ser Glu Pro Pro Leu His Gln Glu Pro Gly Gly Leu Val
            500                 505                 510

Val Pro Pro Thr Asp Ala Pro Val Ser Pro Thr Thr Leu Tyr Val Glu
            515                 520                 525

Asp Ile Ser Glu Pro Pro Leu His Gln Glu Pro Gly Gly Leu Val Val
            530                 535                 540

Pro Pro Thr Asp Ala Pro Val Ser Pro Thr Thr Leu Tyr Val Glu Asp
545                 550                 555                 560

Ile Ser Glu Pro Pro Leu His Glu Glu Pro Glu Cys Asn Asp Ile Thr
                565                 570                 575

Ala Arg Leu Gln Tyr Val Lys Val Gly Ser Cys Lys Ser Glu Val Glu
            580                 585                 590

Val Asp Ile His Tyr Cys Gln Gly Lys Cys Ala Ser Lys Ala Met Tyr
            595                 600                 605
```

```
Ser Ile Asp Ile Asn Asp Val Gln Asp Gln Cys Ser Cys Cys Ser Pro
    610                 615                 620
Thr Arg Thr Glu Pro Met Gln Val Ala Leu His Cys Thr Asn Gly Ser
625                 630                 635                 640
Val Val Tyr His Glu Val Leu Asn Ala Met Glu Cys Lys Cys Ser Pro
                645                 650                 655
Arg Lys Cys Ser Lys
            660

<210> SEQ ID NO 10
<211> LENGTH: 683
<212> TYPE: PRT
<213> ORGANISM: Homo sapiens

<400> SEQUENCE: 10

Met Ile Pro Ala Arg Phe Ala Gly Val Leu Leu Ala Leu Ala Leu Ile
1               5                   10                  15
Leu Pro Gly Thr Leu Cys Ser Leu Ser Cys Arg Pro Pro Met Val Lys
            20                  25                  30
Leu Val Cys Pro Ala Asp Asn Leu Arg Ala Glu Gly Leu Glu Cys Thr
        35                  40                  45
Lys Thr Cys Gln Asn Tyr Asp Leu Glu Cys Met Ser Met Gly Cys Val
    50                  55                  60
Ser Gly Cys Leu Cys Pro Pro Gly Met Val Arg His Glu Asn Arg Cys
65                  70                  75                  80
Val Ala Leu Glu Arg Cys Pro Cys Phe His Gln Gly Lys Glu Tyr Ala
                85                  90                  95
Pro Gly Glu Thr Val Lys Ile Gly Cys Asn Thr Cys Val Cys Gln Asp
            100                 105                 110
Arg Lys Trp Asn Cys Thr Asp His Val Cys Asp Ala Thr Cys Ser Thr
        115                 120                 125
Ile Gly Met Ala His Tyr Leu Thr Phe Asp Gly Leu Lys Tyr Leu Phe
    130                 135                 140
Pro Gly Glu Cys Gln Tyr Val Leu Val Gln Asp Tyr Cys Gly Ser Asn
145                 150                 155                 160
Pro Gly Thr Phe Arg Ile Leu Val Gly Asn Lys Gly Cys Ser His Pro
                165                 170                 175
Ser Val Lys Cys Lys Arg Val Thr Ile Leu Val Glu Gly Gly Glu
            180                 185                 190
Ile Glu Leu Phe Asp Gly Glu Val Asn Val Lys Arg Pro Met Lys Asp
        195                 200                 205
Glu Thr His Phe Glu Val Val Glu Ser Gly Arg Tyr Ile Ile Leu Leu
    210                 215                 220
Leu Gly Lys Ala Leu Ser Val Val Trp Asp Arg His Leu Ser Ile Ser
225                 230                 235                 240
Val Val Leu Lys Gln Thr Tyr Gln Glu Lys Val Cys Gly Leu Cys Gly
                245                 250                 255
Asn Phe Asp Gly Ile Gln Asn Asn Asp Leu Thr Ser Ser Asn Leu Gln
            260                 265                 270
Val Glu Glu Asp Pro Val Asp Phe Gly Asn Ser Trp Lys Val Ser Ser
        275                 280                 285
Gln Cys Ala Asp Thr Arg Lys Val Pro Leu Asp Ser Ser Pro Ala Thr
    290                 295                 300
Cys His Asn Asn Ile Met Lys Gln Thr Met Val Asp Ser Ser Cys Arg
305                 310                 315                 320
```

Ile Leu Thr Ser Asp Val Phe Gln Asp Cys Asn Lys Leu Val Asp Pro
            325                 330                 335

Glu Pro Tyr Leu Asp Val Cys Ile Tyr Asp Thr Cys Ser Cys Glu Ser
            340                 345                 350

Ile Gly Asp Cys Ala Cys Phe Cys Asp Thr Ile Ala Ala Tyr Ala His
            355                 360                 365

Val Cys Ala Gln His Gly Lys Val Val Thr Trp Arg Thr Ala Thr Leu
            370                 375                 380

Cys Pro Gln Ser Cys Glu Glu Arg Asn Leu Arg Glu Asn Gly Tyr Glu
385                 390                 395                 400

Cys Glu Trp Arg Tyr Asn Ser Cys Ala Pro Ala Cys Gln Val Thr Cys
            405                 410                 415

Gln His Pro Glu Pro Leu Ala Cys Pro Val Gln Cys Val Glu Gly Cys
            420                 425                 430

His Ala His Cys Pro Pro Gly Lys Ile Leu Asp Glu Leu Leu Gln Thr
            435                 440                 445

Cys Val Asp Pro Glu Asp Cys Pro Val Cys Glu Val Ala Gly Arg Arg
            450                 455                 460

Phe Ala Ser Gly Lys Lys Val Thr Leu Asn Pro Ser Asp Pro Glu His
465                 470                 475                 480

Cys Gln Ile Cys His Cys Asp Val Val Asn Leu Thr Cys Glu Ala Cys
            485                 490                 495

Gln Glu Pro Gly Gly Leu Val Val Pro Pro Thr Asp Ala Pro Val Ser
            500                 505                 510

Pro Thr Thr Leu Tyr Val Glu Asp Ile Ser Glu Pro Pro Leu His Gln
            515                 520                 525

Glu Pro Gly Gly Leu Val Val Pro Pro Thr Asp Ala Pro Val Ser Pro
            530                 535                 540

Thr Thr Leu Tyr Val Glu Asp Ile Ser Glu Pro Pro Leu His Gln Glu
545                 550                 555                 560

Pro Gly Gly Leu Val Val Pro Pro Thr Asp Ala Pro Val Ser Pro Thr
            565                 570                 575

Thr Leu Tyr Val Glu Asp Ile Ser Glu Pro Pro Leu His Glu Glu Pro
            580                 585                 590

Glu Cys Asn Asp Ile Thr Ala Arg Leu Gln Tyr Val Lys Val Gly Ser
            595                 600                 605

Cys Lys Ser Glu Val Glu Val Asp Ile His Tyr Cys Gln Gly Lys Cys
            610                 615                 620

Ala Ser Lys Ala Met Tyr Ser Ile Asp Ile Asn Asp Val Gln Asp Gln
625                 630                 635                 640

Cys Ser Cys Cys Ser Pro Thr Arg Thr Glu Pro Met Gln Val Ala Leu
            645                 650                 655

His Cys Thr Asn Gly Ser Val Val Tyr His Glu Val Leu Asn Ala Met
            660                 665                 670

Glu Cys Lys Cys Ser Pro Arg Lys Cys Ser Lys
            675                 680

<210> SEQ ID NO 11
<211> LENGTH: 1423
<212> TYPE: PRT
<213> ORGANISM: Homo sapiens

<400> SEQUENCE: 11

Met Ile Pro Ala Arg Phe Ala Gly Val Leu Leu Ala Leu Ala Leu Ile

-continued

```
1               5                   10                  15
Leu Pro Gly Thr Leu Cys Ala Glu Gly Thr Arg Gly Arg Ser Ser Thr
                20                  25                  30
Ala Arg Cys Ser Leu Phe Gly Ser Asp Phe Val Asn Thr Phe Asp Gly
                35                  40                  45
Ser Met Tyr Ser Phe Ala Gly Tyr Cys Ser Tyr Leu Leu Ala Gly Gly
                50                  55                  60
Cys Gln Lys Arg Ser Phe Ser Ile Ile Gly Asp Phe Gln Asn Gly Lys
65                  70                  75                  80
Arg Val Ser Leu Ser Val Tyr Leu Gly Glu Phe Phe Asp Ile His Leu
                85                  90                  95
Phe Val Asn Gly Thr Val Thr Gln Gly Asp Gln Arg Val Ser Met Pro
                100                 105                 110
Tyr Ala Ser Lys Gly Leu Tyr Leu Glu Thr Glu Ala Gly Tyr Tyr Lys
                115                 120                 125
Leu Ser Gly Glu Ala Tyr Gly Phe Val Ala Arg Ile Asp Gly Ser Gly
                130                 135                 140
Asn Phe Gln Val Leu Leu Ser Asp Arg Tyr Phe Asn Lys Thr Cys Gly
145                 150                 155                 160
Leu Cys Gly Asn Phe Asn Ile Phe Ala Glu Asp Asp Phe Met Thr Gln
                165                 170                 175
Glu Gly Thr Leu Thr Ser Asp Pro Tyr Asp Phe Ala Asn Ser Trp Ala
                180                 185                 190
Leu Ser Ser Gly Glu Gln Trp Cys Glu Arg Ala Ser Pro Pro Ser Ser
                195                 200                 205
Ser Cys Asn Ile Ser Ser Gly Glu Met Gln Lys Gly Leu Trp Glu Gln
                210                 215                 220
Cys Gln Leu Leu Lys Ser Thr Ser Val Phe Ala Arg Cys His Pro Leu
225                 230                 235                 240
Val Asp Pro Glu Pro Phe Val Ala Leu Cys Glu Lys Thr Leu Cys Glu
                245                 250                 255
Cys Ala Gly Gly Leu Glu Cys Ala Cys Pro Ala Leu Leu Glu Tyr Ala
                260                 265                 270
Arg Thr Cys Ala Gln Glu Gly Met Val Leu Tyr Gly Trp Thr Asp His
                275                 280                 285
Ser Ala Cys Ser Pro Val Cys Pro Ala Gly Met Glu Tyr Arg Gln Cys
                290                 295                 300
Val Ser Pro Cys Ala Arg Thr Cys Gln Ser Leu His Ile Asn Glu Met
305                 310                 315                 320
Cys Gln Glu Arg Cys Val Asp Gly Cys Ser Cys Pro Glu Gly Gln Leu
                325                 330                 335
Leu Asp Glu Gly Leu Cys Val Glu Ser Thr Glu Cys Pro Cys Val His
                340                 345                 350
Ser Gly Lys Arg Tyr Pro Pro Gly Thr Ser Leu Ser Arg Asp Cys Asn
                355                 360                 365
Thr Cys Ile Cys Arg Asn Ser Gln Trp Ile Cys Ser Asn Glu Glu Cys
                370                 375                 380
Pro Gly Glu Cys Leu Val Thr Gly Gln Ser His Phe Lys Ser Phe Asp
385                 390                 395                 400
Asn Arg Tyr Phe Thr Phe Ser Gly Ile Cys Gln Tyr Leu Leu Ala Arg
                405                 410                 415
Asp Cys Gln Asp His Ser Phe Ser Ile Val Ile Glu Thr Val Gln Cys
                420                 425                 430
```

```
Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845
```

-continued

```
Cys Val Cys Gln Asp Arg Lys Trp Asn Cys Thr Asp His Val Cys Asp
        850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                    885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Arg Val Thr Ile Leu
            915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
            965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
            995                 1000                1005

Ser Ser  Asn Leu Gln Val Glu  Glu Asp Pro Val Asp  Phe Gly Asn
1010                1015                1020

Ser Trp  Lys Val Ser Ser Gln  Cys Ala Asp Thr Arg  Lys Val Pro
    1025                1030                1035

Leu Asp  Ser Ser Pro Ala Thr  Cys His Asn Asn Ile  Met Lys Gln
1040                1045                1050

Thr Met  Val Asp Ser Ser Cys  Arg Ile Leu Thr Ser  Asp Val Phe
    1055                1060                1065

Gln Asp  Cys Asn Lys Leu Val  Asp Pro Glu Pro Tyr  Leu Asp Val
    1070                1075                1080

Cys Ile  Tyr Asp Thr Cys Ser  Cys Glu Ser Ile Gly  Asp Cys Ala
    1085                1090                1095

Cys Phe  Cys Asp Thr Ile Ala  Ala Tyr Ala His Val  Cys Ala Gln
1100                1105                1110

His Gly  Lys Val Val Thr Trp  Arg Thr Ala Thr Leu  Cys Pro Gln
    1115                1120                1125

Ser Cys  Glu Glu Arg Asn Leu  Arg Glu Asn Gly Tyr  Glu Cys Glu
    1130                1135                1140

Trp Arg  Tyr Asn Ser Cys Ala  Pro Ala Cys Gln Val  Thr Cys Gln
    1145                1150                1155

His Pro  Glu Pro Leu Ala Cys  Pro Val Gln Cys Val  Glu Gly Cys
1160                1165                1170

His Ala  His Cys Pro Pro Gly  Lys Ile Leu Asp Glu  Leu Leu Gln
    1175                1180                1185

Thr Cys  Val Asp Pro Glu Asp  Cys Pro Val Cys Glu  Val Ala Gly
    1190                1195                1200

Arg Arg  Phe Ala Ser Gly Lys  Lys Val Thr Leu Asn  Pro Ser Asp
    1205                1210                1215

Pro Glu  His Cys Gln Ile Cys  His Cys Asp Val Val  Asn Leu Thr
    1220                1225                1230

Cys Glu  Ala Cys Gln Glu Pro  Gly Gly Leu Val Val  Pro Pro Thr
    1235                1240                1245

Asp Ala  Pro Val Ser Pro Thr  Thr Leu Tyr Val Glu  Asp Ile Ser
```

```
                1250                1255                1260

Glu Pro Pro Leu His Gln Glu Pro Gly Gly Leu Val Val Pro Pro
            1265                1270                1275

Thr Asp Ala Pro Val Ser Pro Thr Thr Leu Tyr Val Glu Asp Ile
        1280                1285                1290

Ser Glu Pro Pro Leu His Gln Glu Pro Gly Gly Leu Val Val Pro
    1295                1300                1305

Pro Thr Asp Ala Pro Val Pro Thr Thr Leu Tyr Val Glu Asp Ile
    1310                1315                1320

Ser Glu Pro Pro Leu His Glu Glu Pro Glu Cys Asn Asp Ile Thr
    1325                1330                1335

Ala Arg Leu Gln Tyr Val Lys Val Gly Ser Cys Lys Ser Glu Val
    1340                1345                1350

Glu Val Asp Ile His Tyr Cys Gln Gly Lys Cys Ala Ser Lys Ala
    1355                1360                1365

Met Tyr Ser Ile Asp Ile Asn Asp Val Gln Asp Gln Cys Ser Cys
    1370                1375                1380

Cys Ser Pro Thr Arg Thr Glu Pro Met Gln Val Ala Leu His Cys
    1385                1390                1395

Thr Asn Gly Ser Val Val Tyr His Glu Val Leu Asn Ala Met Glu
    1400                1405                1410

Cys Lys Cys Ser Pro Arg Lys Cys Ser Lys
    1415                1420

<210> SEQ ID NO 12
<211> LENGTH: 16
<212> TYPE: PRT
<213> ORGANISM: Homo sapiens

<400> SEQUENCE: 12

Ser Phe Ser Gln Asn Ser Arg His Gln Ala Tyr Arg Tyr Arg Arg Gly
1               5                   10                  15

<210> SEQ ID NO 13
<211> LENGTH: 1440
<212> TYPE: PRT
<213> ORGANISM: Homo sapiens

<400> SEQUENCE: 13

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
```

-continued

```
              130                 135                 140
Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
                180                 185                 190

His Lys Phe Ile Leu Leu Phe Ala Val Phe Asp Glu Gly Lys Ser Trp
            195                 200                 205

His Ser Glu Thr Lys Asn Ser Leu Met Gln Asp Arg Asp Ala Ala Ser
            210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
                260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
            290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
                340                 345                 350

Ser Glu Met Asp Val Val Arg Phe Asp Asp Asp Asn Ser Pro Ser Phe
            355                 360                 365

Ile Gln Ile Arg Ser Val Ala Lys Lys His Pro Lys Thr Trp Val His
            370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
            450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
            530                 535                 540

Ser Gly Leu Ile Gly Pro Leu Leu Ile Cys Tyr Lys Glu Ser Val Asp
545                 550                 555                 560
```

-continued

```
Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
        610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Gln Ala Tyr Arg
            740                 745                 750

Tyr Arg Arg Gly Glu Ile Thr Arg Thr Thr Leu Gln Ser Asp Gln Glu
        755                 760                 765

Glu Ile Asp Tyr Asp Asp Thr Ile Ser Val Glu Met Lys Lys Glu Asp
770                 775                 780

Phe Asp Ile Tyr Asp Glu Asp Glu Asn Gln Ser Pro Arg Ser Phe Gln
785                 790                 795                 800

Lys Lys Thr Arg His Tyr Phe Ile Ala Ala Val Glu Arg Leu Trp Asp
                805                 810                 815

Tyr Gly Met Ser Ser Ser Pro His Val Leu Arg Asn Arg Ala Gln Ser
            820                 825                 830

Gly Ser Val Pro Gln Phe Lys Lys Val Val Phe Gln Glu Phe Thr Asp
        835                 840                 845

Gly Ser Phe Thr Gln Pro Leu Tyr Arg Gly Glu Leu Asn Glu His Leu
    850                 855                 860

Gly Leu Leu Gly Pro Tyr Ile Arg Ala Glu Val Glu Asp Asn Ile Met
865                 870                 875                 880

Val Thr Phe Arg Asn Gln Ala Ser Arg Pro Tyr Ser Phe Tyr Ser Ser
                885                 890                 895

Leu Ile Ser Tyr Glu Glu Asp Gln Arg Gln Gly Ala Glu Pro Arg Lys
            900                 905                 910

Asn Phe Val Lys Pro Asn Glu Thr Lys Thr Tyr Phe Trp Lys Val Gln
        915                 920                 925

His His Met Ala Pro Thr Lys Asp Glu Phe Asp Cys Lys Ala Trp Ala
    930                 935                 940

Tyr Phe Ser Asp Val Asp Leu Glu Lys Asp Val His Ser Gly Leu Ile
945                 950                 955                 960

Gly Pro Leu Leu Val Cys His Thr Asn Thr Leu Asn Pro Ala His Gly
                965                 970                 975
```

```
Arg Gln Val Thr Val Gln Glu Phe Ala Leu Phe Phe Thr Ile Phe Asp
                980             985                 990

Glu Thr Lys Ser Trp Tyr Phe Thr Glu Asn Met Glu Arg Asn Cys Arg
            995             1000                1005

Ala Pro Cys Asn Ile Gln Met Glu Asp Pro Thr Phe Lys Glu Asn
       1010             1015             1020

Tyr Arg Phe His Ala Ile Asn Gly Tyr Ile Met Asp Thr Leu Pro
       1025             1030             1035

Gly Leu Val Met Ala Gln Asp Gln Arg Ile Arg Trp Tyr Leu Leu
       1040             1045             1050

Ser Met Gly Ser Asn Glu Asn Ile His Ser Ile His Phe Ser Gly
       1055             1060             1065

His Val Phe Thr Val Arg Lys Lys Glu Glu Tyr Lys Met Ala Leu
       1070             1075             1080

Tyr Asn Leu Tyr Pro Gly Val Phe Glu Thr Val Glu Met Leu Pro
       1085             1090             1095

Ser Lys Ala Gly Ile Trp Arg Val Glu Cys Leu Ile Gly Glu His
       1100             1105             1110

Leu His Ala Gly Met Ser Thr Leu Phe Leu Val Tyr Ser Asn Lys
       1115             1120             1125

Cys Gln Thr Pro Leu Gly Met Ala Ser Gly His Ile Arg Asp Phe
       1130             1135             1140

Gln Ile Thr Ala Ser Gly Gln Tyr Gly Gln Trp Ala Pro Lys Leu
       1145             1150             1155

Ala Arg Leu His Tyr Ser Gly Ser Ile Asn Ala Trp Ser Thr Lys
       1160             1165             1170

Glu Pro Phe Ser Trp Ile Lys Val Asp Leu Leu Ala Pro Met Ile
       1175             1180             1185

Ile His Gly Ile Lys Thr Gln Gly Ala Arg Gln Lys Phe Ser Ser
       1190             1195             1200

Leu Tyr Ile Ser Gln Phe Ile Ile Met Tyr Ser Leu Asp Gly Lys
       1205             1210             1215

Lys Trp Gln Thr Tyr Arg Gly Asn Ser Thr Gly Thr Leu Met Val
       1220             1225             1230

Phe Phe Gly Asn Val Asp Ser Ser Gly Ile Lys His Asn Ile Phe
       1235             1240             1245

Asn Pro Pro Ile Ile Ala Arg Tyr Ile Arg Leu His Pro Thr His
       1250             1255             1260

Tyr Ser Ile Arg Ser Thr Leu Arg Met Glu Leu Met Gly Cys Asp
       1265             1270             1275

Leu Asn Ser Cys Ser Met Pro Leu Gly Met Glu Ser Lys Ala Ile
       1280             1285             1290

Ser Asp Ala Gln Ile Thr Ala Ser Ser Tyr Phe Thr Asn Met Phe
       1295             1300             1305

Ala Thr Trp Ser Pro Ser Lys Ala Arg Leu His Leu Gln Gly Arg
       1310             1315             1320

Ser Asn Ala Trp Arg Pro Gln Val Asn Asn Pro Lys Glu Trp Leu
       1325             1330             1335

Gln Val Asp Phe Gln Lys Thr Met Lys Val Thr Gly Val Thr Thr
       1340             1345             1350

Gln Gly Val Lys Ser Leu Leu Thr Ser Met Tyr Val Lys Glu Phe
       1355             1360             1365

Leu Ile Ser Ser Ser Gln Asp Gly His Gln Trp Thr Leu Phe Phe
```

```
                       1370                1375                1380

Gln Asn Gly Lys Val Lys Val Phe Gln Gly Asn Gln Asp Ser Phe
            1385                1390                1395

Thr Pro Val Val Asn Ser Leu Asp Pro Pro Leu Leu Thr Arg Tyr
        1400                1405                1410

Leu Arg Ile His Pro Gln Ser Trp Val His Gln Ile Ala Leu Arg
        1415                1420                1425

Met Glu Val Leu Gly Cys Glu Ala Gln Asp Leu Tyr
        1430                1435                1440

<210> SEQ ID NO 14
<211> LENGTH: 1530
<212> TYPE: PRT
<213> ORGANISM: Homo sapiens

<400> SEQUENCE: 14

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300
```

```
Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
            325                 330                 335

Met Lys Asn Asn Glu Glu Ala Glu Asp Tyr Asp Asp Asp Leu Thr Asp
                340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
            690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
```

```
            725                 730                 735
Ile Glu Pro Arg Ser Phe Ser Gln Asn Ser Arg His Gln Glu Pro Gly
            740                 745                 750
Gly Leu Val Val Pro Pro Thr Asp Ala Pro Val Ser Pro Thr Thr Leu
            755                 760                 765
Tyr Val Glu Asp Ile Ser Glu Pro Pro Leu His Gln Glu Pro Gly Gly
            770                 775                 780
Leu Val Val Pro Pro Thr Asp Ala Pro Val Ser Pro Thr Thr Leu Tyr
785                 790                 795                 800
Val Glu Asp Ile Ser Glu Pro Pro Leu His Gln Glu Pro Gly Gly Leu
                805                 810                 815
Val Val Pro Pro Thr Asp Ala Pro Val Ser Pro Thr Thr Leu Tyr Val
                820                 825                 830
Glu Asp Ile Ser Glu Pro Pro Leu His Arg Tyr Arg Arg Gly Glu Ile
                835                 840                 845
Thr Arg Thr Thr Leu Gln Ser Asp Gln Glu Glu Ile Asp Tyr Asp Asp
850                 855                 860
Thr Ile Ser Val Glu Met Lys Lys Glu Asp Phe Asp Ile Tyr Asp Glu
865                 870                 875                 880
Asp Glu Asn Gln Ser Pro Arg Ser Phe Gln Lys Lys Thr Arg His Tyr
                885                 890                 895
Phe Ile Ala Ala Val Glu Arg Leu Trp Asp Tyr Gly Met Ser Ser Ser
                900                 905                 910
Pro His Val Leu Arg Asn Arg Ala Gln Ser Gly Ser Val Pro Gln Phe
                915                 920                 925
Lys Lys Val Val Phe Gln Glu Phe Thr Asp Gly Ser Phe Thr Gln Pro
930                 935                 940
Leu Tyr Arg Gly Glu Leu Asn Glu His Leu Gly Leu Leu Gly Pro Tyr
945                 950                 955                 960
Ile Arg Ala Glu Val Glu Asp Asn Ile Met Val Thr Phe Arg Asn Gln
                965                 970                 975
Ala Ser Arg Pro Tyr Ser Phe Tyr Ser Ser Leu Ile Ser Tyr Glu Glu
                980                 985                 990
Asp Gln Arg Gln Gly Ala Glu Pro Arg Lys Asn Phe Val Lys Pro Asn
                995                 1000                1005
Glu Thr Lys Thr Tyr Phe Trp Lys Val Gln His His Met Ala Pro
                1010                1015                1020
Thr Lys Asp Glu Phe Asp Cys Lys Ala Trp Ala Tyr Phe Ser Asp
                1025                1030                1035
Val Asp Leu Glu Lys Asp Val His Ser Gly Leu Ile Gly Pro Leu
                1040                1045                1050
Leu Val Cys His Thr Asn Thr Leu Asn Pro Ala His Gly Arg Gln
                1055                1060                1065
Val Thr Val Gln Glu Phe Ala Leu Phe Phe Thr Ile Phe Asp Glu
                1070                1075                1080
Thr Lys Ser Trp Tyr Phe Thr Glu Asn Met Glu Arg Asn Cys Arg
                1085                1090                1095
Ala Pro Cys Asn Ile Gln Met Glu Asp Pro Thr Phe Lys Glu Asn
                1100                1105                1110
Tyr Arg Phe His Ala Ile Asn Gly Tyr Ile Met Asp Thr Leu Pro
                1115                1120                1125
Gly Leu Val Met Ala Gln Asp Gln Arg Ile Arg Trp Tyr Leu Leu
                1130                1135                1140
```

-continued

```
Ser Met Gly Ser Asn Glu Asn Ile His Ser Ile His Phe Ser Gly
1145                1150                1155

His Val Phe Thr Val Arg Lys Lys Glu Glu Tyr Lys Met Ala Leu
1160                1165                1170

Tyr Asn Leu Tyr Pro Gly Val Phe Glu Thr Val Glu Met Leu Pro
1175                1180                1185

Ser Lys Ala Gly Ile Trp Arg Val Glu Cys Leu Ile Gly Glu His
1190                1195                1200

Leu His Ala Gly Met Ser Thr Leu Phe Leu Val Tyr Ser Asn Lys
1205                1210                1215

Cys Gln Thr Pro Leu Gly Met Ala Ser Gly His Ile Arg Asp Phe
1220                1225                1230

Gln Ile Thr Ala Ser Gly Gln Tyr Gly Gln Trp Ala Pro Lys Leu
1235                1240                1245

Ala Arg Leu His Tyr Ser Gly Ser Ile Asn Ala Trp Ser Thr Lys
1250                1255                1260

Glu Pro Phe Ser Trp Ile Lys Val Asp Leu Leu Ala Pro Met Ile
1265                1270                1275

Ile His Gly Ile Lys Thr Gln Gly Ala Arg Gln Lys Phe Ser Ser
1280                1285                1290

Leu Tyr Ile Ser Gln Phe Ile Ile Met Tyr Ser Leu Asp Gly Lys
1295                1300                1305

Lys Trp Gln Thr Tyr Arg Gly Asn Ser Thr Gly Thr Leu Met Val
1310                1315                1320

Phe Phe Gly Asn Val Asp Ser Ser Gly Ile Lys His Asn Ile Phe
1325                1330                1335

Asn Pro Pro Ile Ile Ala Arg Tyr Ile Arg Leu His Pro Thr His
1340                1345                1350

Tyr Ser Ile Arg Ser Thr Leu Arg Met Glu Leu Met Gly Cys Asp
1355                1360                1365

Leu Asn Ser Cys Ser Met Pro Leu Gly Met Glu Ser Lys Ala Ile
1370                1375                1380

Ser Asp Ala Gln Ile Thr Ala Ser Ser Tyr Phe Thr Asn Met Phe
1385                1390                1395

Ala Thr Trp Ser Pro Ser Lys Ala Arg Leu His Leu Gln Gly Arg
1400                1405                1410

Ser Asn Ala Trp Arg Pro Gln Val Asn Asn Pro Lys Glu Trp Leu
1415                1420                1425

Gln Val Asp Phe Gln Lys Thr Met Lys Val Thr Gly Val Thr Thr
1430                1435                1440

Gln Gly Val Lys Ser Leu Leu Thr Ser Met Tyr Val Lys Glu Phe
1445                1450                1455

Leu Ile Ser Ser Ser Gln Asp Gly His Gln Trp Thr Leu Phe Phe
1460                1465                1470

Gln Asn Gly Lys Val Lys Val Phe Gln Gly Asn Gln Asp Ser Phe
1475                1480                1485

Thr Pro Val Val Asn Ser Leu Asp Pro Pro Leu Leu Thr Arg Tyr
1490                1495                1500

Leu Arg Ile His Pro Gln Ser Trp Val His Gln Ile Ala Leu Arg
1505                1510                1515

Met Glu Val Leu Gly Cys Glu Ala Gln Asp Leu Tyr
1520                1525                1530
```

<210> SEQ ID NO 15
<211> LENGTH: 3807
<212> TYPE: DNA
<213> ORGANISM: Homo sapiens

<400> SEQUENCE: 15

| | | | | | |
|---|---|---|---|---|---|
| atgatccccg | ccagatttgc | cggcgtgctg | ctggccctgg | ctctgatcct | gcctggaaca | 60 |
| ctgtgtgccg | agggcaccag | aggcagatcc | agcaccgcca | gatgcagcct | gttcggcagc | 120 |
| gacttcgtga | acaccttcga | cggcagcatg | tacagcttcg | ccggctactg | ctcctacctg | 180 |
| ctggctggcg | gctgccagaa | gcggagcttt | agcatcatcg | gcgacttcca | gaacggcaag | 240 |
| cgggtgtccc | tgagcgtgta | cctgggcgag | ttcttcgaca | tccacctgtt | cgtgaacggc | 300 |
| accgtgaccc | aggcgatca | gagggtgtcc | atgccctacg | ccagcaaggg | cctgtacctg | 360 |
| gaaacagagg | ccggctatta | caagctgagc | ggcgaggcct | acggcttcgt | ggccagaatc | 420 |
| gatggcagcg | gcaacttcca | ggtgctgctg | agcgaccggt | acttcaacaa | gacctgcggc | 480 |
| ctgtgcggca | atttcaacat | cttcgccgag | gacgacttca | tgacccagga | aggcaccctg | 540 |
| accagcgacc | cctacgactt | cgccaatagc | tgggccctgt | ctagcggcga | gcagtggtgc | 600 |
| gaaagagcca | gccctcctag | cagcagctgc | aacatcagca | gcggcgagat | gcagaaaggc | 660 |
| ctgtgggagc | agtgccagct | gctgaagtcc | accagcgtgt | cgccaggtg | ccaccctctg | 720 |
| gtggaccctg | agccttttgt | ggccctgtgc | gagaaaacac | tgtgcgagtg | tgccggcgga | 780 |
| ctggaatgtg | cctgtcctgc | cctgctggaa | tacgccagaa | cctgcgctca | ggaagggatg | 840 |
| gtgctgtacg | gctggaccga | ccactctgcc | tgtagccctg | tgtgtcctgc | cggcatggaa | 900 |
| tatcggcagt | gcgtgtcccc | ctgcgccagg | acctgtcaga | gcctgcacat | caacgagatg | 960 |
| tgccaggaac | gctgcgtgga | cggctgtagc | tgtcctgagg | acagctgct | ggatgagggc | 1020 |
| ctgtgtgtgg | aaagcaccga | gtgcccttgt | gtgcacagcg | gcaagagata | ccccctggc | 1080 |
| accagcctga | gccgggactg | caatacctgc | atctgccgga | acagccagtg | gatctgctcc | 1140 |
| aacgaggaat | gcctggcga | gtgcctcgtg | acaggccaga | gccacttcaa | gagcttcgac | 1200 |
| aacagatact | tcaccttcag | cggcatctgc | cagtatctgc | tggccagaga | ctgccaggac | 1260 |
| cacagcttca | gcatcgtgat | cgagacagtg | cagtgcgccg | acgacagaga | tgccgtgtgc | 1320 |
| accagatccg | tgaccgtgcg | gctgcctggc | ctgcacaaca | gcctcgtgaa | gctgaaacac | 1380 |
| ggcgctgggg | tggccatgga | cggacaggac | gtgcagctgc | ctctgctgaa | gggcgacctg | 1440 |
| agaatccagc | acaccgtgac | agcctctgtg | cggctgagct | acggcgagga | cctccagatg | 1500 |
| gactgggatg | cagggcag | actgctcgtg | aaactgagcc | cagtgtatgc | cggcaagact | 1560 |
| tgtggactgt | gtggcaacta | caacggcaac | cagggcgacg | atttcctgac | cccttctggc | 1620 |
| ctggccgagc | ccgggtgga | agattttggc | aacgcctgga | agctgcacgg | cgactgtcag | 1680 |
| gatctccaga | agcagcacag | cgaccctgc | gccctgaacc | ccggatgac | cagattcagc | 1740 |
| gaagaggcct | gtgccgtgct | gaccagccct | accttgagg | cctgccacag | agccgtgtct | 1800 |
| ccactgcctt | acctgcggaa | ttgcagatac | gacgtgtgct | cctgctccga | cggccgcgaa | 1860 |
| tgtctgtgtg | gcgccctggc | ctcttatgcc | gccgcttgtg | ctggaagagg | cgtgcgggtg | 1920 |
| gcatggcggg | aaccaggcag | atgcgagctg | aactgccta | agggccaggt | gtacctccag | 1980 |
| tgcggcaccc | cctgcaacct | gacctgtaga | agcctgagct | accccgacga | agagtgcaac | 2040 |
| gaggcctgtc | tggaaggctg | cttttgccct | cccggcctgt | atatggacga | gcggggcgat | 2100 |
| tgtgtgccca | aggcccagtg | cccctgctac | tacgacggcg | agattttcca | gcccgaggac | 2160 |

| | | |
|---|---|---|
| atcttcagcg accaccacac catgtgctac tgcgaggatg gcttcatgca ctgcaccatg | 2220 | |
| agcggcgtgc caggctccct gctgcctgat gctgtgctgt ctagcccct gagccacaga | 2280 | |
| agcaagagaa gcctgtcttg cagaccccc atggtcaagc tcgtgtgccc tgccgacaac | 2340 | |
| ctgagagccg agggcctgga atgcaccaag acatgccaga actacgacct ggaatgcatg | 2400 | |
| agcatgggct gcgtgtccgg ctgtctgtgc cctcctggca tggtgcgcca cgagaataga | 2460 | |
| tgcgtggccc tggaacggtg cccgtgcttt catcagggca agagtacgc cccaggcgaa | 2520 | |
| accgtgaaga tcggctgcaa cacatgcgtg tgtcaggacc ggaagtggaa ctgcaccgac | 2580 | |
| cacgtgtgcg acgccacctg tagcacaatc ggcatggccc actacctgac cttcgatggc | 2640 | |
| ctgaagtacc tgttccccgg cgagtgtcag tacgtgctgg tgcaggatta ctgcggcagc | 2700 | |
| aaccccggca ccttcagaat cctcgtgggc aacaagggct gtagccaccc ctccgtgaag | 2760 | |
| tgcaagaaac gcgtgaccat cctggtggaa ggcggagaga tcgagctgtt cgacggcgaa | 2820 | |
| gtgaacgtga agcggcccat gaaggacgag acacacttcg aggtggtgga aagcggccgg | 2880 | |
| tacatcatcc tgctgctggg caaagccctg tccgtcgtgt gggacagaca cctgagcatc | 2940 | |
| agcgtggtgc tgaagcagac ctaccaggaa aaagtgtgcg ggctgtgtgg gaactttgac | 3000 | |
| ggcatccaga caacgatct gaccagcagc aatctccagg tggaagagga ccccgtggac | 3060 | |
| ttcggcaatt cctggaaggt gtccagccag tgtgccgaca ccagaaaggt gcccctggat | 3120 | |
| agcagccccg ccacatgcca caacaacatc atgaagcaga caatggtgga cagcagctgc | 3180 | |
| cgcatcctga cctccgatgt gtttcaggac tgcaacaaac tggtggaccc cgaaccctac | 3240 | |
| ctggacgtgt gcatctacga cacatgcagc tgcgagagca tcggcgattg cgcctgcttc | 3300 | |
| tgcgacacca ttgccgccta cgcccatgtg tgcgcccagc acggaaaggt cgtgacttgg | 3360 | |
| agaaccgcca ccctgtgccc acagagctgc gaggaacgga acctgcggga aaacggctac | 3420 | |
| gagtgcgagt ggcggtacaa cagctgtgcc ccagcctgcc aagtgacctg ccagcaccct | 3480 | |
| gaacctctgg cttgccccgt gcagtgcgtg gaaggatgtc acgcccattg cccacccggc | 3540 | |
| aagatcctgg atgagctgct ccagaccgt gtggacccag aggactgccc agtgtgcgaa | 3600 | |
| gtggccggaa gaagattcgc ctccggcaag aaagtgaccc tgaatccctc cgaccccgag | 3660 | |
| cactgtcaga tttgtcactg cgacgtcgtg aatctgacat gcgaagcctg ccaggaacct | 3720 | |
| ggcggactgg tggtgcctcc tacagatgcc cctgtgtccc ccaccaccct gtacgtggaa | 3780 | |
| gatatcagcg agccccccct gcactaa | 3807 | |

<210> SEQ ID NO 16
<211> LENGTH: 93
<212> TYPE: DNA
<213> ORGANISM: Homo sapiens

<400> SEQUENCE: 16

| | | |
|---|---|---|
| caggaacctg gcggactggt ggtgcctcct acagatgccc ctgtgtcccc caccaccctg | 60 | |
| tacgtggaag atatcagcga gccccccctg cac | 93 | |

<210> SEQ ID NO 17
<211> LENGTH: 3993
<212> TYPE: DNA
<213> ORGANISM: Homo sapiens

<400> SEQUENCE: 17

| | | |
|---|---|---|
| atgatccccg ccagatttgc cggcgtgctg ctggccctgg ctctgatcct gcctggaaca | 60 | |

-continued

```
ctgtgtgccg agggcaccag aggcagatcc agcaccgcca gatgcagcct gttcggcagc    120
gacttcgtga acaccttcga cggcagcatg tacagcttcg ccggctactg ctcctacctg    180
ctggctggcg gctgccagaa gcggagcttt agcatcatcg gcgacttcca gaacggcaag    240
cgggtgtccc tgagcgtgta cctgggcgag ttcttcgaca tccacctgtt cgtgaacggc    300
accgtgaccc agggcgatca gagggtgtcc atgccctacg ccagcaaggg cctgtacctg    360
gaaacagagg ccggctatta caagctgagc ggcgaggcct acggcttcgt ggccagaatc    420
gatggcagcg gcaacttcca ggtgctgctg agcgaccggt acttcaacaa gacctgcggc    480
ctgtgcggca atttcaacat cttcgccgag gacgacttca tgacccagga aggcacccrg    540
accagcgacc cctacgactt cgccaatagc tgggccctgt ctagcggcga gcagtggtgc    600
gaaagagcca gccctcctag cagcagctgc aacatcagca gcggcgagat gcagaaaggc    660
ctgtgggagc agtgccagct gctgaagtcc accagcgtgt cgccaggtg ccaccctctg    720 gtggaccctg agccttttgt ggccctgtgc gagaaaacac tgtgcgagtg tgccggcgga    780
ctggaatgtg cctgtcctgc cctgctggaa tacgccagaa cctgcgctca ggaagggatg    840
gtgctgtacg gctggaccga ccactctgcc tgtagccctg tgtgtcctgc cggcatggaa    900
tatcggcagt gcgtgtcccc ctgcgccagg acctgtcaga gctgcacat caacgagatg    960 tgccaggaac gctgcgtgga cggctgtagc tgtcctgagg acagctgct ggatgagggc   1020 ctgtgtgtgg aaagcaccga gtgcccttgt gtgcacagcg gcaagagata ccccctggc   1080 accagcctga gccgggactg caataccctgc atctgccgga acagccagtg gatctgctcc   1140
aacgaggaat gccctggcga gtgcctcgtg acaggccaga gccacttcaa gagcttcgac   1200
aacagatact tcaccttcag cggcatctgc cagtatctgc tggccagaga ctgccaggac   1260
cacagcttca gcatcgtgat cgagacagtg cagtgcgccg acgacagaga tgccgtgtgc   1320
accagatccg tgaccgtgcg gctgcctggc ctgcacaaca gcctcgtgaa gctgaaacac   1380
ggcgctgggg tggccatgga cggacaggac gtgcagctgc ctctgctgaa gggcgacctg   1440
agaatccagc acaccgtgac agcctctgtg cggctgagct acggcgagga cctccagatg   1500
gactgggatg gcaggggcag actgctcgtg aaactgagcc cagtgtatgc cggcaagact   1560
tgtggactgt gtggcaacta caacggcaac cagggcgacg atttcctgac cccttctggc   1620
ctggccgagc ccgggtgga agattttggc aacgcctgga gctgcacgg cgactgtcag   1680 gatctccaga agcagcacag cgacccttgc gccctgaacc cccggatgac cagattcagc   1740
gaagaggcct gtgccgtgct gaccagccct acctttgagg cctgccacag agccgtgtct   1800
ccactgcctt acctgcggaa ttgcagatac gacgtgtgct cctgctccga cggccgcgaa   1860
tgtctgtgtg gcgccctggc ctcttatgcc gccgcttgtg ctggaagagg cgtgcgggtg   1920
gcatggcggg aaccaggcag atgcgagctg aactgcccta agggccaggt gtacctccag   1980
tgcggcaccc cctgcaacct gacctgtaga agcctgagct accccgacga agagtgcaac   2040
gaggcctgtc tggaaggctg cttttgccct cccggcctgt atatggacga gcggggcgat   2100
tgtgtgccca aggcccagtg cccctgctac tacgacggcg agattttcca gcccgaggac   2160
atcttcagcg accaccacac catgtgctac tgcgaggatg gcttcatgca ctgcaccatg   2220
agcggcgtgc aggctccct gctgcctgat gctgtgctgt ctagccccct gagccacaga   2280
agcaagagaa gcctgtcttg cagacccccc atggtcaagc tcgtgtgccc tgccgacaac   2340
ctgagagccg agggcctgga atgcaccaag acatgccaga actacgacct ggaatgcatg   2400
agcatgggct gcgtgtccgg ctgtctgtgc cctcctggca tggtgcgcca cgagaataga   2460
```

```
tgcgtggccc tggaacggtg cccgtgcttt catcagggca aagagtacgc cccaggcgaa    2520
accgtgaaga tcggctgcaa cacatgcgtg tgtcaggacc ggaagtggaa ctgcaccgac    2580
cacgtgtgcg acgccacctg tagcacaatc ggcatggccc actacctgac cttcgatggc    2640
ctgaagtacc tgttccccgg cgagtgtcag tacgtgctgg tgcaggatta ctgcggcagc    2700
aaccccggca ccttcagaat cctcgtgggc aacaagggct gtagccaccc ctccgtgaag    2760
tgcaagaaac gcgtgaccat cctggtggaa ggcggagaga tcgagctgtt cgacggcgaa    2820
gtgaacgtga agcggcccat gaaggacgag acacacttcg aggtggtgga aagcggccgg    2880
tacatcatcc tgctgctggg caaagccctg tccgtcgtgt gggacagaca cctgagcatc    2940
agcgtggtgc tgaagcagac ctaccaggaa aaagtgtgcg ggctgtgtgg aactttgac    3000 ggcatccaga caacgatct gaccagcagc aatctccagg tggaagagga ccccgtggac    3060
ttcggcaatt cctggaaggt gtccagccag tgtgccgaca ccagaaaggt gcccctggat    3120
agcagccccg ccacatgcca caacaacatc atgaagcaga caatggtgga cagcagctgc    3180
cgcatcctga cctccgatgt gtttcaggac tgcaacaaac tggtggaccc cgaaccctac    3240
ctggacgtgt gcatctacga cacatgcagc tgcgagagca tcggcgattg cgcctgcttc    3300
tgcgacacca ttgccgccta cgcccatgtg tgcgcccagc acggaaaggt cgtgacttgg    3360
agaaccgcca ccctgtgccc acagagctgc gaggaacgga acctgcggga aaacggctac    3420
gagtgcgagt ggcggtacaa cagctgtgcc ccagcctgcc aagtgacctg ccagcaccct    3480
gaacctctgg cttgccccgt gcagtgcgtg aaggatgtc acgcccattg cccacccggc    3540
aagatcctgg atgagctgct ccagacctgt gtggacccag aggactgccc agtgtgcgaa    3600
gtggccggaa gaagattcgc ctccggcaag aaagtgaccc tgaatccctc cgaccccgag    3660
cactgtcaga tttgtcactg cgacgtcgtg aatctgacat gcgaagcctg ccaggaacct    3720
ggcggactgg tggtgcctcc tacagatgcc cctgtgtccc ccaccaccct gtacgtggaa    3780
gatatcagcg agccccccct gcaccaggaa cctggcggac tggtggtgcc tcctacagac    3840
gctcctgtgt ctcctacaac actgtatgtg aagatatttt ccgagcctcc tctgcatcag    3900
gaaccagggg gcctggtggt gccaccaact gatgcaccag tgtctccaac tactctgtac    3960
gtggaagata tttctgaacc cccccctgcat taa                                3993
```

<210> SEQ ID NO 18
<211> LENGTH: 4179
<212> TYPE: DNA
<213> ORGANISM: Homo sapiens

<400> SEQUENCE: 18

```
atgatcccg ccagatttgc cggcgtgctg ctggccctgg ctctgatcct gcctggaaca    60
ctgtgtgccg agggcaccag aggcagatcc agcaccgcca gatgcagcct gttcggcagc    120
gacttcgtga caccttcga cggcagcatg tacagcttcg ccggctactg ctcctacctg    180
ctggctggcg gctgccagaa gcggagcttt agcatcatcg gcgacttcca gaacggcaag    240
cgggtgtccc tgagcgtgta cctgggcgag ttcttcgaca tccacctgtt cgtgaacggc    300
accgtgaccc agggcgatca gagggtgtcc atgcctacg ccagcaaggg cctgtacctg    360
gaaacagagg ccggctatta caagctgagc ggcgaggcct acggcttcgt ggccagaatc    420
gatggcagcg gcaacttcca ggtgctgctg agcgaccggg acttcaacaa gacctgcggc    480
ctgtgcggca atttcaacat cttcgccgag gacgacttca tgacccagga aggcaccctg    540
```

-continued

```
accagcgacc cctacgactt cgccaatagc tgggccctgt ctagcggcga gcagtggtgc   600
gaaagagcca gccctcctag cagcagctgc aacatcagca gcggcgagat gcagaaaggc   660
ctgtgggagc agtgccagct gctgaagtcc accagcgtgt cgccaggtg ccaccctctg    720
gtggaccctg agccttttgt ggccctgtgc gagaaaacac tgtgcgagtg tgccggcgga   780
ctggaatgtg cctgtcctgc cctgctggaa tacgccagaa cctgcgctca ggaagggatg   840
gtgctgtacg gctggaccga ccactctgcc tgtagccctg tgtgtcctgc cggcatggaa   900
tatcggcagt gcgtgtcccc ctgcgccagg acctgtcaga gcctgcacat caacgagatg   960
tgccaggaac gctgcgtgga cggctgtagc tgtcctgagg acagctgct ggatgagggc    1020
ctgtgtgtgg aaagcaccga gtgcccttgt gtgcacagcg gcaagagata cccccctggc   1080
accagcctga gccgggactg caataccctg atctgccgga acagccagtg gatctgctcc   1140
aacgaggaat gccctggcga gtgcctcgtg acaggccaga gccacttcaa gagcttcgac   1200
aacagatact tcaccttcag cggcatctgc cagtatctgc tggccagaga ctgccaggac   1260
cacagcttca gcatcgtgat cgagacagtg cagtgcgccg acgacagaga tgccgtgtgc   1320
accagatccg tgaccgtgcg gctgcctggc ctgcacaaca gcctcgtgaa gctgaaacac   1380
ggcgctgggg tggccatgga cggacaggac gtgcagctgc ctctgctgaa gggcgacctg   1440
agaatccagc acaccgtgac agcctctgtg cggctgagct acggcgagga cctccagatg   1500
gactgggatg gcaggggcag actgctcgtg aaactgagcc cagtgtatgc cggcaagact   1560
tgtggactgt gtggcaacta acggcaac cagggcgacg atttcctgac ccctttctggc   1620
ctggccgagc cccgggtgga agattttggc aacgcctgga gctgcacgg cgactgtcag    1680
gatctccaga gcagcacag cgacccttgc gccctgaacc cccggatgac cagattcagc    1740
gaagaggcct gtgccgtgct gaccagccct acctttgagg cctgccacag agccgtgtct   1800
ccactgcctt acctgcggaa ttgcagatac gacgtgtgct cctgctccga cggccgcgaa   1860
tgtctgtgtg gcgccctggc ctcttatgcc gccgcttgtg ctggaagagg cgtgcgggtg   1920
gcatggcggg aaccaggcag atgcgagctg aactgcccta agggccaggt gtacctccag   1980
tgcggcaccc cctgcaacct gacctgtaga agcctgagct accccgacga agagtgcaac   2040
gaggcctgtc tggaaggctg cttttgccct cccggcctgt atatggacga gcggggcgat   2100
tgtgtgccca ggcccagtg cccctgctac tacgacggcg agattttcca gcccgaggac   2160
atcttcagcg accaccacac catgtgctac tgcgaggatg gcttcatgca ctgcaccatg   2220
agcggcgtgc caggctccct gctgcctgat gctgtgctgt ctagcccct gagccacaga    2280
agcaagagaa gcctgtcttg cagaccccc atggtcaagc tcgtgtgccc tgccgacaac    2340
ctgagagccg agggcctgga atgcaccaag acatgccaga actacgacct ggaatgcatg   2400
agcatgggct gcgtgtccgg ctgtctgtgc cctcctggca tggtgcgcca cgagaataga   2460
tgcgtggccc tggaacggtg cccgtgcttt catcagggca agagtacgc cccaggcgaa   2520
accgtgaaga tcgctgcaa cacatgcgtg tgtcaggacc ggaagtggaa ctgcaccgac   2580
cacgtgtgcg acgccacctg tagcacaatc ggcatggccc actacctgac cttcgatggc   2640
ctgaagtacc tgttccccgg cgagtgtcag tacgtgctgg tgcaggatta ctgcggcagc   2700
aaccccggca ccttcagaat cctcgtgggc aacaagggct gtagccaccc ctccgtgaag   2760
tgcaagaaac gcgtgaccat cctggtggaa ggcggagaga tcgagctgtt cgacggcgaa   2820
gtgaacgtga gcggcccat gaaggacgag acacacttcg aggtggtgga aagcggccgg   2880
tacatcatcc tgctgctggg caaagccctg tccgtcgtgt gggacagaca cctgagcatc   2940
```

```
agcgtggtgc tgaagcagac ctaccaggaa aaagtgtgcg ggctgtgtgg gaactttgac    3000
ggcatccaga caacgatct gaccagcagc aatctccagg tggaagagga ccccgtggac    3060
ttcggcaatt cctggaaggt gtccagccag tgtgccgaca ccagaaaggt gcccctggat    3120
agcagccccg ccacatgcca caacaacatc atgaagcaga caatggtgga cagcagctgc    3180
cgcatcctga cctccgatgt gtttcaggac tgcaacaaac tggtggaccc cgaaccctac    3240
ctggacgtgt gcatctacga cacatgcagc tgcgagagca tcggcgattg cgcctgcttc    3300
tgcgacacca ttgccgccta cgcccatgtg tgcgcccagc acggaaaggt cgtgacttgg    3360
agaaccgcca ccctgtgccc acagagctgc gaggaacgga acctgcggga aaacggctac    3420
gagtgcgagt ggcggtacaa cagctgtgcc ccagcctgcc aagtgacctg ccagcaccct    3480
gaacctctgg cttgccccgt gcagtgcgtg aaggatgtc acgcccattg cccacccggc    3540
aagatcctgg atgagctgct ccagacctgt gtggacccag aggactgccc agtgtgcgaa    3600
gtggccggaa gaagattcgc ctccggcaag aaagtgaccc tgaatccctc cgaccccgag    3660
cactgtcaga tttgtcactg cgacgtcgtg aatctgacat gcgaagcctg ccaggaacct    3720
ggcggactgt ggtgcctcc tacagatgcc cctgtgtccc ccaccaccct gtacgtggaa    3780
gatatcagcg agccccccct gcaccaagaa cctggtggac tggtggtgcc tcctacagat    3840
gctcctgtgt ctcccaccac actgtacgtg aagatatca gcgagcctcc tctgcaccaa    3900
gagccaggcg gacttgtggt cccaccaact gatgcccctg tcagccctac aactctgtac    3960
gtcgaggaca tctccgagcc accactgcat caagaacctg gcggccttgt cgttcctcca    4020
acagacgcac ctgttagccc aactacactg tatgttgagg acataagcga accgcctctc    4080
catcaagaac ccggtggtct tgttgtccca cctacagacg ccccagtctc tcctaccact    4140
ctctatgtcg aagatatttc cgaacctcca ctgcactaa                          4179
```

<210> SEQ ID NO 19
<211> LENGTH: 4275
<212> TYPE: DNA
<213> ORGANISM: Homo sapiens

<400> SEQUENCE: 19

```
atgatccccg ccagatttgc cggcgtgctg ctggccctgg ctctgatcct gcctggaaca     60
ctgtgtgccg agggcaccag aggcagatcc agcaccgcca gatgcagcct gttcggcagc    120
gacttcgtga caccttcga cggcagcatg tacagcttcg ccggctactg ctcctacctg    180
ctggctggcg gctgccagaa gcggagcttt agcatcatcg gcgacttcca gaacggcaag    240
cgggtgtccc tgagcgtgta cctgggcgag ttcttcgaca tccacctgtt cgtgaacggc    300
accgtgaccc agggcgatca gagggtgtcc atgccctacg ccagcaaggg cctgtacctg    360
gaaacagagg ccggctatta caagctgagc ggcgaggcct acggcttcgt ggccagaatc    420
gatggcagcg gcaacttcca ggtgctgctg agcgaccggt acttcaacaa gacctgcggc    480
ctgtgcggca atttcaacat cttcgccgag gacgacttca tgacccagga aggcacccct    540
accagcgacc cctacgactt cgccaatagc tgggcctgt ctagcggcga gcagtggtgc    600
gaaagagcca gccctcctag cagcagctgc aacatcagca gcggcgagat gcagaaaggc    660
ctgtgggagc agtgccagct gctgaagtcc accagcgtgt cgccaggtg ccaccctctg    720 gtggaccctg agcctttgt ggccctgtgc gagaaaacac tgtgcgagtg tgccggcgga    780
ctggaatgtg cctgtcctgc cctgctggaa tacgccagaa cctgcgctca ggaagggatg    840
```

```
gtgctgtacg gctggaccga ccactctgcc tgtagccctg tgtgtcctgc cggcatggaa      900
tatcggcagt gcgtgtcccc ctgcgccagg acctgtcaga gcctgcacat caacgagatg      960
tgccaggaac gctgcgtgga cggctgtagc tgtcctgagg acagctgct ggatgagggc      1020
ctgtgtgtgg aaagcaccga gtgcccttgt gtgcacagcg gcaagagata ccccctggc      1080
accagcctga gccgggactg caataccctg catctgccga acagccagtg gatctgctcc      1140
aacgaggaat gccctggcga gtgcctcgtg acaggccaga gccacttcaa gagcttcgac      1200
aacagatact tcaccttcag cggcatctgc cagtatctgc tggccagaga ctgccaggac      1260
cacagcttca gcatcgtgat cgagacagtg cagtgcgccg acgacagaga tgccgtgtgc      1320
accagatccg tgaccgtgcg gctgcctggc ctgcacaaca gcctcgtgaa gctgaaacac      1380
ggcgctgggg tggccatgga cggacaggac gtgcagctgc ctctgctgaa gggcgacctg      1440
agaatccagc acaccgtgac agcctctgtg cggctgagct acggcgagga cctccagatg      1500
gactgggatg gcaggggcag actgctcgtg aaactgagcc cagtgtatgc cggcaagact      1560
tgtggactgt gtggcaacta caacggcaac cagggcgacg atttcctgac cccttctggc      1620
ctggccgagc ccgggtgga agattttggc aacgcctgga gctgcacgg cgactgtcag      1680
gatctccaga agcagcacag cgaccctgc gccctgaacc ccggatgac cagattcagc      1740
gaagaggcct gtgccgtgct gaccagcccct accttgagg cctgccacag agccgtgtct      1800
ccactgcctt acctgcggaa ttgcagatac gacgtgtgct cctgctccga cggccgcgaa      1860
tgtctgtgtg gcgccctggc ctcttatgcc gccgcttgtg ctggaagagg cgtgcgggtg      1920
gcatggcggg aaccaggcag atgcgagctg aactgcccta agggccaggt gtacctccag      1980
tgcggcaccc cctgcaacct gacctgtaga agcctgagct accccgacga agagtgcaac      2040
gaggcctgtc tggaaggctg ctttttgccct cccggcctgt atatggacga gcggggcgat      2100
tgtgtgccca aggcccagtg cccctgctac tacgacggcg agattttcca gcccgaggac      2160
atcttcagcg accaccacac catgtgctac tgcgaggatg gcttcatgca ctgcaccatg      2220
agcggcgtgc caggctccct gctgcctgat gctgtgctgt ctagccccct gagccacaga      2280
agcaagagaa gcctgtcttg cagaccccca atggtcaagc tcgtgtgccc tgccgacaac      2340
ctgagagccg agggcctgga atgcaccaag acatgccaga actacgacct ggaatgcatg      2400
agcatgggct gcgtgtccgg ctgtctgtgc cctcctggca tggtgcgcca cgagaataga      2460
tgcgtggccc tggaacggtg cccgtgcttt catcagggca agagtacgc cccaggcgaa      2520
accgtgaaga tcggctgcaa cacatgcgtg tgtcaggacc ggaagtggaa ctgcaccgac      2580
cacgtgtgcg acgccacctg tagcacaatc ggcatggccc actacctgac cttcgatggc      2640
ctgaagtacc tgttcccgg cgagtgtcag tacgtgctgg tgcaggatta ctgcggcagc      2700
aaccccggca ccttcagaat cctcgtgggc aacaagggct gtagccaccc ctccgtgaag      2760
tgcaagaaac gcgtgaccat cctggtggaa ggcggagaga tcgagctgtt cgacggcgaa      2820
gtgaacgtga gcggcccat gaaggacgag acacacttcg aggtggtgga aagcggccgg      2880
tacatcatcc tgctgctggg caaagccctg tccgtcgtgt gggacagaca cctgagcatc      2940
agcgtggtgc tgaagcagac ctaccaggaa aaagtgtgcg gctgtgtgg aactttgac      3000
ggcatccaga caacgatct gaccagcagc aatctccagg tggaagagga ccccgtggac      3060
ttcggcaatt cctggaaggt gtccagccag tgtgccgaca ccagaaaggt gcccctggat      3120
agcagccccg ccacatgcca caacaacatc atgaagcaga caatggtgga cagcagctgc      3180
cgcatcctga cctccgatgt gttttcagga ctgcaacaaac tggtggaccc cgaaccctac      3240
```

-continued

| | |
|---|---|
| ctggacgtgt gcatctacga cacatgcagc tgcgagagca tcggcgattg cgcctgcttc | 3300 |
| tgcgacacca ttgccgccta cgcccatgtg tgcgcccagc acggaaaggt cgtgacttgg | 3360 |
| agaaccgcca ccctgtgccc acagagctgc gaggaacgga acctgcggga aaacggctac | 3420 |
| gagtgcgagt ggcggtacaa cagctgtgcc ccagcctgcc aagtgacctg ccagcaccct | 3480 |
| gaacctctgg cttgccccgt gcagtgcgtg aaggatgtc acgcccattg cccacccggc | 3540 |
| aagatcctgg atgagctgct ccagaccgt gtggacccag aggactgccc agtgtgcgaa | 3600 |
| gtggccggaa gaagattcgc ctccggcaag aaagtgaccc tgaatccctc cgaccccgag | 3660 |
| cactgtcaga tttgtcactg cgacgtcgtg aatctgacat gcgaagcctg ccaggaacct | 3720 |
| ggcggactgg tggtgcctcc tacagatgcc cctgtgtccc ccaccaccct gtacgtggaa | 3780 |
| gatatcagcg agcccccct gcaccaagaa cctggtggac tggtggtgcc tcctacagat | 3840 |
| gctcctgtgt ctcccaccac actgtacgtg aagatatca gcgagcctcc tctgcaccaa | 3900 |
| gagccaggcg gacttgtggt cccaccaact gatgcccctg tcagccctac aactctgtac | 3960 |
| gtcgaggaca tctccgagcc accactgcac gaggaacccg agtgcaacga tatcaccgcc | 4020 |
| agactgcagt acgtgaaagt gggcagctgc aagagcgagg tggaagtgga catccactac | 4080 |
| tgccagggca gtgtgccag caaggccatg tacagcatcg acatcaacga cgtgcaggac | 4140 |
| cagtgcagct gctgcagccc aacaagaacc gagcctatgc aggtcgccct gcactgtaca | 4200 |
| aatggcagcg tggtgtacca cgaggtgctg aacgccatgg aatgcaagtg cagccccaga | 4260 |
| aagtgcagca agtaa | 4275 |

<210> SEQ ID NO 20
<211> LENGTH: 4659
<212> TYPE: DNA
<213> ORGANISM: Homo sapiens

<400> SEQUENCE: 20

| | |
|---|---|
| atgcaaatag agctctccac ctgcttcttt ctgtgccttt tgcgattctg ctttagtgcc | 60 |
| accagaagat actacctggg tgcagtggaa ctgtcatggg actatatgca aagtgatctc | 120 |
| ggtgagctgc ctgtggacgc aagatttcct cctagagtgc caaaatcttt tccattcaac | 180 |
| acctcagtcg tgtacaaaaa gactctgttt gtagaattca cggatcacct tttcaacatc | 240 |
| gctaagccaa ggccacctg atgggtctg ctaggtccta ccatccaggc tgaggtttat | 300 |
| gatacagtgg tcattacact taagaacatg gcttcccatc ctgtcagtct tcatgctgtt | 360 |
| ggtgtatcct actggaaagc ttctgaggga gctgaatatg atgatcagac cagtcaaagg | 420 |
| gagaaagaag atgataaagt cttccctggt ggaagccata catatgtctg gcaggtcctg | 480 |
| aaagagaatg gtccaatggc ctctgaccca ctgtgcctta cctactcata tctttctcat | 540 |
| gtggacctgg taaaagactt gaattcaggc ctcattggag ccctactagt atgtagagaa | 600 |
| gggagtctgg ccaaggaaaa gacacagacc ttgcacaaat ttatactact ttttgctgta | 660 |
| tttgatgaag ggaaaagttg gcactcagaa acaaagaact ccttgatgca ggatagggat | 720 |
| gctgcatctg ctcgggcctg gcctaaaatg cacacagtca atggttatgt aaacaggtct | 780 |
| ctgccaggtc tgattggatg ccacaggaaa tcagtctatt ggcatgtgat tggaatgggc | 840 |
| accactcctg aagtgcactc aatattcctc gaaggtcaca catttcttgt gaggaaccat | 900 |
| cgccaggcgt cctggaaat ctcgccaata actttcctta ctgctcaaac actcttgatg | 960 |
| gaccttggac agtttctact gttttgtcat atctcttccc accaacatga tggcatggaa | 1020 |

```
gcttatgtca aagtagacag ctgtccagag gaaccccaac tacgaatgaa aaataatgaa    1080
gaagcggaag actatgatga tgatcttact gattctgaaa tggatgtggt caggtttgat    1140
gatgacaact ctccttcctt tatccaaatt cgctcagttg ccaagaagca tcctaaaact    1200
tgggtacatt acattgctgc tgaagaggag gactgggact atgctcsctt agtcctcgcc    1260
cccgatgaca gaagttataa aagtcaatat ttgaacaatg cccctcagcg gattggtagg    1320
aagtacaaaa aagtccgatt tatggcatac acagatgaaa cctttaagac tcgtgaagct    1380
attcagcatg aatcaggaat cttgggacct ttactttatg gggaagttgg agacacactg    1440
ttgattatat ttaagaatca agcaagcaga ccatataaca tctaccctca cggaatcact    1500
gatgtccgtc ctttgtattc aaggagatta ccaaaaggtg taaaacattt gaaggatttt    1560
ccaattctgc caggagaaat attcaaatat aaatggacag tgactgtaga agatgggcca    1620
actaaatcag atcctcggtg cctgacccgc tattactcta gtttcgttaa tatggagaga    1680
gatctagctt caggactcat tggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt ccttctgtc ttcttctctg gatataccttt caaacacaaa    2040 atggtctatg aagacacact caccctattc ccattctcag agaaactgt cttcatgtcg    2100 atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaga attcaagaca tcaggaacct ggcggactgg tggtgcctcc tacagatgcc    2340
cctgtgtccc ccaccaccct gtacgtggaa gatatcagcg agccccccct gcaccaggaa    2400
cctggcggac tggtggtgcc tcctacagac gctcctgtgt ctcctacaac actgtatgtg    2460
gaagatattt ccgagcctcc tctgcatcag gaaccagggg gcctggtggt gccaccaact    2520
gatgcaccag tgtctccaac tactctgtac gtggaagata tttctgaacc cccctgcat    2580 caagcttatc gataccgtcg aggggaaata actcgtacta ctcttcagtc agatcaagag    2640
gaaattgact atgatgatac catatcagtt gaaatgaaga aggaagattt tgacatttat    2700
gatgaggatg aaaatcagag cccccgcagc tttcaaaaga aaacacgaca ctatttttatt    2760 gctgcagtgg agaggctctg ggattatggg atgagtagct ccccacatgt tctaagaaac    2820
agggctcaga gtggcagtgt ccctcagttc aagaaagttg ttttccagga atttactgat    2880
ggctccttta ctcagcccctt ataccgtgga gaactaaatg aacatttggg actcctgggg    2940
ccatatataa gagcagaagt tgaagataat atcatggtaa ctttcagaaa tcaggcctct    3000
cgtccctatt ccttctattc tagccttatt tcttatgagg aagatcagag gcaaggagca    3060
gaacctagaa aaaactttgt caagcctaat gaaaccaaaa cttactttgt gaaagtgcaa    3120
catcatatgg cacccactaa agatgagttt gactgcaaag cctgggctta tttctctgat    3180
gttgacctgg aaaaagatgt gcactcaggc ctgattggac cccttctggt ctgccacact    3240
aacacactga accctgctca tgggagacaa gtgacagtac aggaatttgc tctgttttc    3300 accatctttg atgagaccaa aagctggtac ttcactgaaa atatgaaag aaactgcagg    3360 gctccctgca atatccagat ggaagatccc acttttaaag agaattatcg cttccatgca    3420
```

```
atcaatggct acataatgga tacactacct ggcttagtaa tggctcagga tcaaaggatt    3480
cgatggtatc tgctcagcat gggcagcaat gaaaacatcc attctattca tttcagtgga    3540
catgtgttca ctgtacgaaa aaagaggag tataaaatgg cactgtacaa tctctatcca     3600 ggtgttttg agacagtgga aatgttacca tccaaagctg gaatttggcg ggtggaatgc     3660
cttattggcg agcatctaca tgctgggatg agcacctttt ttctggtgta cagcaataag    3720
tgtcagactc ccctgggaat ggcttctgga cacattagag attttcagat tacagcttca    3780
ggacaatatg gacagtgggc cccaaagctg gccagacttc attattccgg atcaatcaat    3840
gcctggagca ccaaggagcc cttttcttgg atcaaggtgg atctgttggc accaatgatt    3900
attcacggca tcaagaccca gggtgcccgt cagaagttct ccagcctcta catctctcag    3960
tttatcatca tgtatagtct tgatgggaag aagtggcaga cttatcgagg aaattccact    4020
ggaaccttaa tggtcttctt tggcaatgtg gattcatctg gataaaaca caatatttt     4080 aaccctccaa ttattgctcg atacatccgt ttgcacccaa ctcattatag cattcgcagc    4140
actcttcgca tggagttgat gggctgtgat ttaaatagtt gcagcatgcc attgggaatg    4200
gagagtaaag caatatcaga tgcacagatt actgcttcat cctactttac caatatgttt    4260
gccacctggt ctccttcaaa agctcgactt cacctccaag ggaggagtaa tgcctggaga    4320
cctcaggtga ataatccaaa agagtggctg caagtggact tccagaagac aatgaaagtc    4380
acaggagtaa ctactcaggg agtaaaatct ctgcttacca gcatgtatgt gaaggagttc    4440
ctcatctcca gcagtcaaga tggccatcag tggaccctct tttttcagaa tggcaaagta    4500
aaggtttttc agggaaatca agactccttc acacctgtgg tgaactctct agacccaccg    4560
ttactgactc gctaccttcg aattcacccc cagagttggg tgcaccagat tgccctgagg    4620
atggaggttc tgggctgcga ggcacaggac ctctactga                           4659
```

<210> SEQ ID NO 21
<211> LENGTH: 1533
<212> TYPE: PRT
<213> ORGANISM: Homo sapiens

<400> SEQUENCE: 21

```
Ala Thr Arg Arg Tyr Tyr Leu Gly Ala Val Glu Leu Ser Trp Asp Tyr
 1               5                  10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
        50                  55                  60

Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
```

```
                145                 150                 155                 160
            His Val Asp Leu Val Lys Asp Leu Asn Ser Gly Leu Ile Gly Ala Leu
                            165                 170                 175

Leu Val Cys Arg Glu Gly Ser Leu Ala Lys Glu Lys Thr Gln Thr Leu
                            180                 185                 190

His Lys Phe Ile Leu Leu Phe Ala Val Phe Asp Glu Gly Lys Ser Trp
                            195                 200                 205

His Ser Glu Thr Lys Asn Ser Leu Met Gln Asp Arg Asp Ala Ala Ser
                            210                 215                 220

Ala Arg Ala Trp Pro Lys Met His Thr Val Asn Gly Tyr Val Asn Arg
            225                 230                 235                 240

Ser Leu Pro Gly Leu Ile Gly Cys His Arg Lys Ser Val Tyr Trp His
                            245                 250                 255

Val Ile Gly Met Gly Thr Thr Pro Glu Val His Ser Ile Phe Leu Glu
                            260                 265                 270

Gly His Thr Phe Leu Val Arg Asn His Arg Gln Ala Ser Leu Glu Ile
                            275                 280                 285

Ser Pro Ile Thr Phe Leu Thr Ala Gln Thr Leu Leu Met Asp Leu Gly
                            290                 295                 300

Gln Phe Leu Leu Phe Cys His Ile Ser Ser His Gln His Asp Gly Met
            305                 310                 315                 320

Glu Ala Tyr Val Lys Val Asp Ser Cys Pro Glu Glu Pro Gln Leu Arg
                            325                 330                 335

Met Lys Asn Asn Glu Glu Ala Glu Asp Tyr Asp Asp Asp Leu Thr Asp
                            340                 345                 350

Ser Glu Met Asp Val Val Arg Phe Asp Asp Asp Asn Ser Pro Ser Phe
                            355                 360                 365

Ile Gln Ile Arg Ser Val Ala Lys Lys His Pro Lys Thr Trp Val His
                            370                 375                 380

Tyr Ile Ala Ala Glu Glu Glu Asp Trp Asp Tyr Ala Pro Leu Val Leu
            385                 390                 395                 400

Ala Pro Asp Asp Arg Ser Tyr Lys Ser Gln Tyr Leu Asn Asn Gly Pro
                            405                 410                 415

Gln Arg Ile Gly Arg Lys Tyr Lys Lys Val Arg Phe Met Ala Tyr Thr
                            420                 425                 430

Asp Glu Thr Phe Lys Thr Arg Glu Ala Ile Gln His Glu Ser Gly Ile
                            435                 440                 445

Leu Gly Pro Leu Leu Tyr Gly Glu Val Gly Asp Thr Leu Leu Ile Ile
                            450                 455                 460

Phe Lys Asn Gln Ala Ser Arg Pro Tyr Asn Ile Tyr Pro His Gly Ile
            465                 470                 475                 480

Thr Asp Val Arg Pro Leu Tyr Ser Arg Arg Leu Pro Lys Gly Val Lys
                            485                 490                 495

His Leu Lys Asp Phe Pro Ile Leu Pro Gly Glu Ile Phe Lys Tyr Lys
                            500                 505                 510

Trp Thr Val Thr Val Glu Asp Gly Pro Thr Lys Ser Asp Pro Arg Cys
                            515                 520                 525

Leu Thr Arg Tyr Tyr Ser Ser Phe Val Asn Met Glu Arg Asp Leu Ala
                            530                 535                 540

Ser Gly Leu Ile Gly Pro Leu Leu Ile Cys Tyr Lys Glu Ser Val Asp
            545                 550                 555                 560

Gln Arg Gly Asn Gln Ile Met Ser Asp Lys Arg Asn Val Ile Leu Phe
                            565                 570                 575
```

-continued

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Gln Ala Tyr Arg
            740                 745                 750

Tyr Arg Arg Gly Glu Ile Thr Arg Thr Thr Leu Gln Ser Asp Gln Glu
        755                 760                 765

Glu Ile Asp Tyr Asp Asp Thr Ile Ser Val Glu Met Lys Lys Glu Asp
    770                 775                 780

Phe Asp Ile Tyr Asp Glu Asp Glu Asn Gln Ser Pro Arg Ser Phe Gln
785                 790                 795                 800

Lys Lys Thr Arg His Tyr Phe Ile Ala Ala Val Glu Arg Leu Trp Asp
                805                 810                 815

Tyr Gly Met Ser Ser Pro His Val Leu Arg Asn Arg Ala Gln Ser
            820                 825                 830

Gly Ser Val Pro Gln Phe Lys Lys Val Val Phe Gln Glu Phe Thr Asp
        835                 840                 845

Gly Ser Phe Thr Gln Pro Leu Tyr Arg Gly Glu Leu Asn Glu His Leu
    850                 855                 860

Gly Leu Leu Gly Pro Tyr Ile Arg Ala Glu Val Glu Asp Asn Ile Met
865                 870                 875                 880

Val Thr Phe Arg Asn Gln Ala Ser Arg Pro Tyr Ser Phe Tyr Ser Ser
                885                 890                 895

Leu Ile Ser Tyr Glu Glu Asp Gln Arg Gln Gly Ala Glu Pro Arg Lys
            900                 905                 910

Asn Phe Val Lys Pro Asn Glu Thr Lys Thr Tyr Phe Trp Lys Val Gln
        915                 920                 925

His His Met Ala Pro Thr Lys Asp Glu Phe Asp Cys Lys Ala Trp Ala
    930                 935                 940

Tyr Phe Ser Asp Val Asp Leu Glu Lys Asp Val His Ser Gly Leu Ile
945                 950                 955                 960

Gly Pro Leu Leu Val Cys His Thr Asn Thr Leu Asn Pro Ala His Gly
                965                 970                 975

Arg Gln Val Thr Val Gln Glu Phe Ala Leu Phe Phe Thr Ile Phe Asp
            980                 985                 990

```
Glu Thr Lys Ser Trp Tyr Phe Thr Glu Asn Met Glu Arg Asn Cys Arg
        995                 1000                1005

Ala Pro Cys Asn Ile Gln Met Glu Asp Pro Thr Phe Lys Glu Asn
    1010                1015                1020

Tyr Arg Phe His Ala Ile Asn Gly Tyr Ile Met Asp Thr Leu Pro
    1025                1030                1035

Gly Leu Val Met Ala Gln Asp Gln Arg Ile Arg Trp Tyr Leu Leu
    1040                1045                1050

Ser Met Gly Ser Asn Glu Asn Ile His Ser Ile His Phe Ser Gly
    1055                1060                1065

His Val Phe Thr Val Arg Lys Lys Glu Glu Tyr Lys Met Ala Leu
    1070                1075                1080

Tyr Asn Leu Tyr Pro Gly Val Phe Glu Thr Val Glu Met Leu Pro
    1085                1090                1095

Ser Lys Ala Gly Ile Trp Arg Val Glu Cys Leu Ile Gly Glu His
    1100                1105                1110

Leu His Ala Gly Met Ser Thr Leu Phe Leu Val Tyr Ser Asn Lys
    1115                1120                1125

Cys Gln Thr Pro Leu Gly Met Ala Ser Gly His Ile Arg Asp Phe
    1130                1135                1140

Gln Ile Thr Ala Ser Gly Gln Tyr Gly Gln Trp Ala Pro Lys Leu
    1145                1150                1155

Ala Arg Leu His Tyr Ser Gly Ser Ile Asn Ala Trp Ser Thr Lys
    1160                1165                1170

Glu Pro Phe Ser Trp Ile Lys Val Asp Leu Leu Ala Pro Met Ile
    1175                1180                1185

Ile His Gly Ile Lys Thr Gln Gly Ala Arg Gln Lys Phe Ser Ser
    1190                1195                1200

Leu Tyr Ile Ser Gln Phe Ile Ile Met Tyr Ser Leu Asp Gly Lys
    1205                1210                1215

Lys Trp Gln Thr Tyr Arg Gly Asn Ser Thr Gly Thr Leu Met Val
    1220                1225                1230

Phe Phe Gly Asn Val Asp Ser Ser Gly Ile Lys His Asn Ile Phe
    1235                1240                1245

Asn Pro Pro Ile Ile Ala Arg Tyr Ile Arg Leu His Pro Thr His
    1250                1255                1260

Tyr Ser Ile Arg Ser Thr Leu Arg Met Glu Leu Met Gly Cys Asp
    1265                1270                1275

Leu Asn Ser Cys Ser Met Pro Leu Gly Met Glu Ser Lys Ala Ile
    1280                1285                1290

Ser Asp Ala Gln Ile Thr Ala Ser Ser Tyr Phe Thr Asn Met Phe
    1295                1300                1305

Ala Thr Trp Ser Pro Ser Lys Ala Arg Leu His Leu Gln Gly Arg
    1310                1315                1320

Ser Asn Ala Trp Arg Pro Gln Val Asn Asn Pro Lys Glu Trp Leu
    1325                1330                1335

Gln Val Asp Phe Gln Lys Thr Met Lys Val Thr Gly Val Thr Thr
    1340                1345                1350

Gln Gly Val Lys Ser Leu Leu Thr Ser Met Tyr Val Lys Glu Phe
    1355                1360                1365

Leu Ile Ser Ser Ser Gln Asp Gly His Gln Trp Thr Leu Phe Phe
    1370                1375                1380

Gln Asn Gly Lys Val Lys Val Phe Gln Gly Asn Gln Asp Ser Phe
```

|   |   |   |   |   |   |   |   |   |   |
|---|---|---|---|---|---|---|---|---|---|
| | | 1385 | | | 1390 | | | 1395 | |
| Thr | Pro | Val | Val | Asn | Ser | Leu | Asp | Pro | Pro | Leu | Leu | Thr | Arg | Tyr |
| 1400 | | | | | 1405 | | | | 1410 | |
| Leu | Arg | Ile | His | Pro | Gln | Ser | Trp | Val | His | Gln | Ile | Ala | Leu | Arg |
| 1415 | | | | | 1420 | | | | 1425 | |
| Met | Glu | Val | Leu | Gly | Cys | Glu | Ala | Gln | Asp | Leu | Tyr | Gln | Glu | Pro |
| 1430 | | | | | 1435 | | | | 1440 | |
| Gly | Gly | Leu | Val | Val | Pro | Pro | Thr | Asp | Ala | Pro | Val | Ser | Pro | Thr |
| 1445 | | | | | 1450 | | | | 1455 | |
| Thr | Leu | Tyr | Val | Glu | Asp | Ile | Ser | Glu | Pro | Pro | Leu | His | Gln | Glu |
| 1460 | | | | | 1465 | | | | 1470 | |
| Pro | Gly | Gly | Leu | Val | Val | Pro | Pro | Thr | Asp | Ala | Pro | Val | Ser | Pro |
| 1475 | | | | | 1480 | | | | 1485 | |
| Thr | Thr | Leu | Tyr | Val | Glu | Asp | Ile | Ser | Glu | Pro | Pro | Leu | His | Gln |
| 1490 | | | | | 1495 | | | | 1500 | |
| Glu | Pro | Gly | Gly | Leu | Val | Val | Pro | Pro | Thr | Asp | Ala | Pro | Val | Ser |
| 1505 | | | | | 1510 | | | | 1515 | |
| Pro | Thr | Thr | Leu | Tyr | Val | Glu | Asp | Ile | Ser | Glu | Pro | Pro | Leu | His |
| 1520 | | | | | 1525 | | | | 1530 | |

<210> SEQ ID NO 22
<211> LENGTH: 4659
<212> TYPE: DNA
<213> ORGANISM: Homo sapiens

<400> SEQUENCE: 22

```
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc aaaatctttt tccattcaac     180
acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgg tcattacact taagaacatg gcttcccatc ctgtcagtct tcatgctgtt     360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaagacttg aattcaggc ctcattggag ccctactagt atgtagagaa     600
gggagtctgg ccaaggaaaa gacacagacc ttgcacaaat ttatactact ttttgctgta     660
tttgatgaag ggaaaagttg gcactcagaa acaagaact ccttgatgca ggatagggat     720
gctgcatctg ctcgggcctg gcctaaaatg cacacagtca atggttatgt aaacaggtct     780
ctgccaggtc tgattggatg ccacaggaaa tcagtctatt ggcatgtgat tggaatgggc     840
accactcctg aagtgcactc aatattcctc gaaggtcaca catttcttgt gaggaaccat     900
cgccaggcgt ccttggaaat ctcgccaata actttcctta ctgctcaaac actcttgatg     960
gaccttggac agtttctact gttttgtcat atctcttccc accaacatga tggcatggaa    1020
gcttatgtca agtagacag ctgtccagag gaaccccaac tacgaatgaa aaataatgaa    1080
gaagcggaag actatgatga tgatcttact gattctgaaa tggatgtggt caggtttgat    1140
gatgacaact ctccttcctt tatccaaatt cgctcagttg ccaagaagca tcctaaaact    1200
tgggtacatt acattgctgc tgaagaggag gactgggact atgctccctt agtcctcgcc    1260
```

```
cccgatgaca gaagttataa aagtcaatat ttgaacaatg gccctcagcg gattggtagg    1320
aagtacaaaa aagtccgatt tatggcatac acagatgaaa cctttaagac tcgtgaagct    1380
attcagcatg aatcaggaat cttgggacct ttactttatg gggaagttgg agacacactg    1440
ttgattatat ttaagaatca agcaagcaga ccatataaca tctaccctca cggaatcact    1500
gatgtccgtc ctttgtattc aaggagatta ccaaaggtg taaaacattt gaaggatttt    1560
ccaattctgc caggagaaat attcaaatat aaatggacag tgactgtaga agatgggcca    1620
actaaatcag atcctcggtg cctgacccgc tattactcta gtttcgttaa tatggagaga    1680
gatctagctt caggactcat tggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg atataccttt caaacacaaa    2040
atggtctatg aagacacact caccctattc ccattctcag agaaactgt cttcatgtcg    2100
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaga attcaagaca tcaagcttat cgataccgtc gagggaaat aactcgtact    2340
actcttcagt cagatcaaga ggaaattgac tatgatgata ccatatcagt tgaaatgaag    2400
aaggaagatt ttgacatttta tgatgaggat gaaaatcaga gccccgcag ctttcaaaag    2460
aaaacacgac actattttat tgctgcagtg gagaggctct gggattatgg gatgagtagc    2520
tccccacatg ttctaagaaa cagggctcag agtggcagtg tccctcagtt caagaaagtt    2580
gttttccagg aatttactga tggctccttt actcagccct tataccgtgg agaactaaat    2640
gaacatttgg gactcctggg gccatatata agagcagaag ttgaagataa tatcatggta    2700
actttcagaa atcaggcctc tcgtcctat tccttctatt ctagccttat ttcttatgag    2760
gaagatcaga ggcaaggagc agaacctaga aaaactttg tcaagcctaa tgaaaccaaa    2820
acttactttt ggaaagtgca acatcatatg gcacccacta agatgagtt tgactgcaaa    2880
gcctgggctt atttctctga tgttgacctg gaaaaagatg tgcactcagg cctgattgga    2940
cccttctgg tctgccacac taacacactg aaccctgctc atgggagaca agtgacagta    3000
caggaatttg ctctgttttt caccatcttt gatgagacca aaagctggta cttcactgaa    3060
aatatggaaa gaaactgcag ggctccctgc aatatccaga tggaagatcc cacttttaaa    3120
gagaattatc gcttccatgc aatcaatggc tacataatgg atacactacc tggcttagta    3180
atggctcagg atcaaaggat tcgatggtat ctgctcagca tgggcagcaa tgaaaacatc    3240
cattctattc atttcagtgg acatgtgttc actgtacgaa aaaagagga gtataaaatg    3300
gcactgtaca atctctatcc aggtgttttt gagacagtgg aaatgttacc atccaaagct    3360
ggaatttggc gggtggaatg ccttattggc gagcatctac atgctgggat gagcacactt    3420
tttctggtgt acagcaataa gtgtcagact cccctgggaa tggcttctgg acacattaga    3480
gattttcaga ttacagcttc aggacaatat ggacagtggg ccccaaagct ggccagactt    3540
cattattccg gatcaatcaa tgcctggagc accaaggagc ccttttcttg gatcaaggtg    3600
gatctgttgg caccaatgat tattcacggc atcaagaccc agggtgcccg tcagaagttc    3660
```

```
tccagcctct acatctctca gtttatcatc atgtatagtc ttgatgggaa gaagtggcag    3720
acttatcgag gaaattccac tggaacctta atggtcttct ttggcaatgt ggattcatct    3780
gggataaaac acaatatttt taaccctcca attattgctc gatacatccg tttgcaccca    3840
actcattata gcattcgcag cactcttcgc atggagttga tgggctgtga tttaaatagt    3900
tgcagcatgc cattgggaat ggagagtaaa gcaatatcag atgcacagat tactgcttca    3960
tcctacttta ccaatatgtt tgccacctgg tctccttcaa aagctcgact tcacctccaa    4020
gggaggagta atgcctggag acctcaggtg aataatccaa aagagtggct gcaagtggac    4080
ttccagaaga caatgaaagt cacaggagta actactcagg gagtaaaatc tctgcttacc    4140
agcatgtatg tgaaggagtt cctcatctcc agcagtcaag atggccatca gtggaccctc    4200 tttttcaga atggcaaagt aaaggttttt cagggaaatc aagactcctt cacacctgtg    4260
gtgaactctc tagacccacc gttactgact cgctaccttc gaattcaccc ccagagttgg    4320
gtgcaccaga ttgccctgag gatggaggtt ctgggctgcg aggcacagga cctctaccag    4380
gaacctggcg gactggtggt gcctcctaca gatgcccctg tgtccccac  caccctgtac    4440 gtggaagata tcagcgagcc ccccctgcac caggaacctg gcggactggt ggtgcctcct    4500
acagacgctc ctgtgtctcc tacaacactg tatgtggaag atatttccga gcctcctctg    4560
catcaggaac caggggggcct ggtggtgcca ccaactgatg caccagtgtc tccaactact    4620
ctgtacgtgg aagatatttc tgaaccccc  ctgcattga                            4659
```

GLYCOSYLATED VWF FUSION PROTEINS WITH IMPROVED PHARMACOKINETICS

SEQUENCE LISTING

A sequence listing in electronic (ASCII text file) format is filed with this application and incorporated herein by reference. The name of the ASCII text file is "2018_1978A_ST25.txt"; the file was created on Jun. 7, 2024; the size of the file is 167,445 bytes.

FIELD OF THE INVENTION

The invention relates to the half-life prolongation of proteins, in particular human coagulation factors such as von Willebrand factor (VWF) and factor VIII (FVIII).

BACKGROUND OF THE INVENTION

Hemophilia is a group of hereditary genetic disorders that impair the body's ability to control blood clotting or coagulation. In its most common form, Hemophilia A, clotting factor VIII (FVIII) is deficient. Hemophilia A occurs in about 1 in 5,000-10,000 male births. The FVIII protein is an essential cofactor in blood coagulation with multifunctional properties. The deficiency of FVIII can be treated with plasma-derived concentrates of FVIII or with recombinantly produced FVIII. The treatment with FVIII concentrates has led to a normalized life of the hemophilia patients.

Hemophilia A patients are treated with FVIII on demand or as a prophylactic therapy administered several times a week. For prophylactic treatment, 15-25 IU/kg bodyweight of FVIII is administered three times a week, which is necessary due to the constant need of FVIII and its short half-life in the blood system, which in humans is only about 11 hours (Ewenstein et al., 2004).

In the blood, under normal conditions, the FVIII molecule is always associated with its cofactor von Willebrand factor (VWF), which stabilizes the FVIII molecule from different forms of degeneration. The non-covalent complex of FVIII and VWF has a high binding affinity of 0.2-0.3 nM (Vlot et al., 1996).

Historically, Hemophilia A has been treated with FVIII originating from human blood plasma. However, since the 1990s, different recombinantly produced FVIII proteins were marketed. However, neither the plasma-derived nor the recombinant produced FVIII proteins have optimal pharmacokinetic properties. Like many other therapeutic proteins they are subject to metabolic turnover by peptidases, which significantly limits their in vivo half-life.

As reviewed by Tiede et al. (2015), attempts for prolonging FVIII half-life include Fc fusion (Eloctate, Elocta, efmoroctocog alfa), addition of polyethylene glycol (turoctocog alfa pegol [N8-GP], BAY 94-9027, BAX 855), and a single-chain construct (CSL627). All these technologies change the FVIII molecule and result in approximate 1.5 times half-life prolonged FVIII.

Further half-life extension of FVIII is limited to the VWF half-life. As shown by Yee et al., the human VWF D'D3 domain is sufficient to stabilize FVIII in plasma. However, a D'D3-Fc fusion protein is able to extend FVIII half-life only in VWF−/− mice. In Hemophilia A mice, the D'D3-Fc construct does not result in FVIII half-life prolongation due to ineffective competition of the protein fragments with endogenous VWF for FVIII binding.

WO 2014/011819 A2 describes successful half-life prolongation of a FVIII construct containing the D'D3 domain of VWF, the Fc domain of IgG and XTEN. Since this construct does not bind to endogenous VWF, the same half-life prolonging effect is seen in both VWF/FVIII-double knock-out (DKO) and Hemophilia A mice. However, although fully functional in vitro, it exhibits markedly reduced activity in vivo.

Other approaches for increasing the half-life of therapeutic proteins include the genetic fusion of the therapeutic protein to a protein with naturally long half-life such as transferrin and albumin, or to protein domains such as the C-terminal peptide (CTP) of chorionic gonadotropin (CG).

CG belongs to the glycoprotein hormone family that includes luteinizing hormone (LH), follicle-stimulating hormone (FSH), and thyroid-stimulating hormone (TSH). These glycohormones are heterodimeric and consist of a common α-subunit and unique β-subunits that confer their different activities. The half-life of human CG (hCG) is significantly longer than the half-life of its counterparts LH, FSH and TSH. It was shown that the O-glycosylated CTP of hCG-β is responsible for this half-life prolongation. The CTP is described to consist of the sequence FQSSSS*KAPPPS*LPSPS*RLPGPS*DTPILPQ (SEQ ID NO:23), which possesses four O-glycosylation sites (denoted by S*) (Birken et al., 1977).

As reviewed in Strohl et al (2015), different fusion proteins of a therapeutic protein and CTP have been developed and are presently in clinical trials. The therapeutic proteins include FSH (Elonva®), FVIIa, FIX, IFN-β and oxyntomodulin.

SUMMARY OF THE INVENTION

The present invention is inter alia based on the finding that the addition of a cluster of O-glycosylated amino acids (which is present in full-length human VWF) to a fragment of VWF leads to a significant increase in its half-life. The half-life of the fusion protein is prolonged in comparison to the VWF fragment without the additional O-glycan cluster.

Thus, according to a first aspect, the invention relates to a fusion protein comprising a main protein and at least one extension peptide, wherein the amino acid sequence of the main protein is identical or similar to the amino acid sequence of a mammalian protein, such as VWF, or a fragment thereof, and said extension peptide comprises a cluster of O-glycosylated amino acids.

Interestingly, the extension peptide including the cluster of O-glycosylated amino acids, which is added to a fragment of VWF, is derived from this exact protein, namely VWF. Accordingly, the applicant has identified a general principle for extending the half-life of proteins. This general principle is the addition of an intrinsic cluster of O-glycosylated amino acids of a protein to said protein or fragment thereof.

Thus, according to a preferred embodiment of the fusion protein according to the first aspect, the amino acid sequence of the one or more extension peptides is identical or similar to a non-repeated amino acid sequence section of said mammalian protein or fragment, in particular of said main protein.

The further conclusion from the findings of the inventors is that the cluster of 0-glycosylated amino acids of VWF identified by SEQ ID NO: 1 is useful as a half-life extension peptide.

As the half-life extending property is not limited to VWF, according to a further preferred embodiment of the first aspect, the one or more extension peptides have a sequence identity of at least 90%, preferably at least 95%, more preferably at least 98%, most preferably at least 100% to an O-glycosylated peptide of VWF, in particular to SEQ ID NO: 1.

In a second aspect, the invention relates to a polynucleotide encoding a fusion protein according to the first aspect.

According to the third aspect, the invention relates to a vector containing the polynucleotide according to the second aspect.

In a fourth aspect, the invention relates to a host cell containing the polynucleotide according to the second aspect or the vector according to the third aspect, wherein the host cell is a mammalian cell.

The inventors have found that not only the half-life of VWF is increased, but also the half-life of its binding partner FVIII. Thus, according to a fifth aspect, the invention relates to the use of a fusion protein according to the first aspect for increasing the half-life of a second protein, wherein the fusion protein is capable of binding to said second protein.

Thus, in the resulting complex or composition of the fusion protein and the second protein, the second protein also has an increased half-life.

Therefore, in a sixth aspect, the invention relates to a composition of a first protein and a second protein, wherein said first protein is a fusion protein according to the first aspect and is capable of binding said second protein, and said second protein is a therapeutic protein comprising an amino acid sequence that is identical or similar to the amino acid sequence of a second mammalian protein or fragment thereof.

And according to a seventh aspect, the invention relates to a complex of a first protein and a second protein, wherein said first protein is a fusion protein according to the first aspect, and said second protein has an amino acid sequence which is identical or similar to the amino acid sequence of a second mammalian protein or fragment thereof.

Finally, in an eighth aspect, the invention also relates to a pharmaceutical composition comprising the fusion protein according to the first aspect, a composition according to the sixth aspect, or a complex according to the seventh aspect, for use in the treatment or prevention of a bleeding disorder, preferably selected from treatment of PUPs, or the treatment of ITI and other related bleeding disorder treatments.

FIGURES

FIG. 1 shows schematic representations of A) a VWF fragment OCTA 11, and B) a fusion protein according to the invention with a VWF fragment as main protein: OCTA 12; C) a fusion protein according to the invention with a VWF fragment as main protein: OCTA14; D) a fusion protein according to the invention with a VWF fragment as main protein: OCTA15.

FIG. 2 shows a time-course of FVIII activity following intravenous administration of FVIII co-formulated with different VWF proteins or plasma-derived full-length VWF in FVIII/VWF double knock out (DKO) mice plasma. The data points and error bars represent the mean and standard deviation (SD) of 5 values. Due to the small size several of the error bars are not discernible.

DETAILED DESCRIPTION OF THE INVENTION

Figure 1:
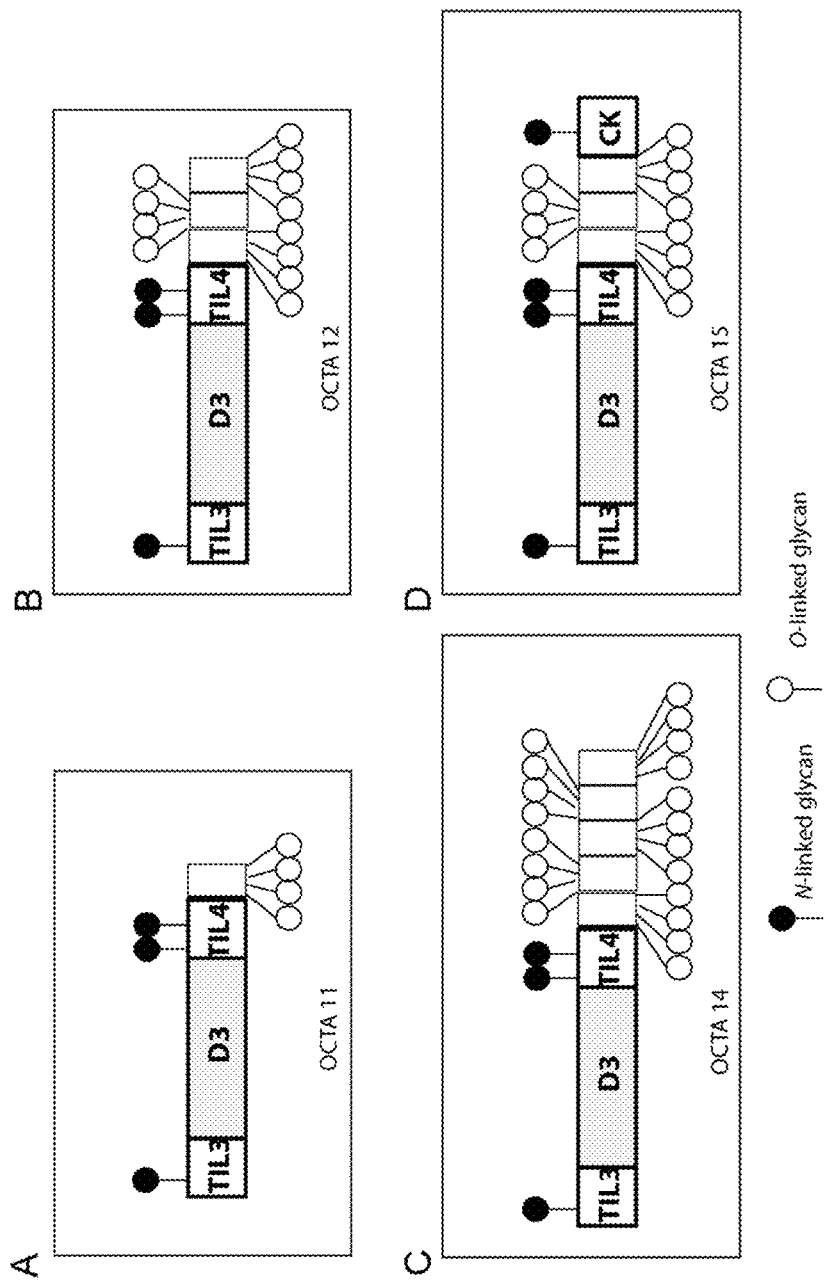

In order to provide a clear and consistent understanding of the specification and claims, and the scope to be given such terms, the following definitions are provided.

Definitions

A "peptide" as used herein may be composed of any number of amino acids of any type, preferably naturally occurring amino acids, which, preferably, are linked by peptide bonds. In particular, a peptide comprises at least 3 amino acids, preferably at least 5, at least 7, at least 9, at least 12, or at least 15 amino acids. Furthermore, there is no upper limit for the length of a peptide. However, preferably, a peptide according to the invention does not exceed a length of 500 amino acids, more preferably it does not exceed a length of 300 amino acids; even more preferably it is not longer than 250 amino acids.

Thus, the term "peptide" includes "oligopeptides", which usually refer to peptides with a length of 2 to 10 amino acids, and "polypeptides" which usually refer to peptides with a length of more than 10 amino acids.

A "protein" as used herein may contain one or more polypeptide chains. Proteins with more than one polypeptide chain are often expressed as one polypeptide chain from one gene and cleaved post translationally. Thus, the terms "polypeptide" and "protein" are used interchangeably. The polypeptides and proteins as used herein include chemically synthesized proteins as well as naturally synthesized proteins which are encoded by genes. The polypeptides or proteins may be obtained from a natural source, such as human blood or produced in cell culture as recombinant proteins.

The term "therapeutic protein" as used herein relates to proteins or polypeptides with a therapeutic effect, i.e. proteins used as active pharmaceutical ingredient.

According to the invention the terms "protein precursor", "pro-protein" or "pro-peptide", relate to an inactive protein (or peptide) that can be turned into an active form by post-translational modification, enzymatic cleavage of a portion of the amino acid sequence.

The relatedness between two amino acid sequences or between two nucleotide sequences is described by the parameter "sequence identity". For purposes of the present invention, the degree of sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et a/., 2000, Trends Genet. 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the no brief option) is used as the percent identity and is calculated as follows:

$$(\text{Identical Residues} \times 100)/(\text{Length of Alignment} - \text{Total Number of Gaps in Alignment}).$$

For purposes of the present invention, the degree of sequence identity between two nucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et a/., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Desoxyribonucleotides×100)/(Length of Alignment−Total Number of Gaps in Alignment)

The terms "similarity" and "similar" as used herein with respect to the definition of a peptide or polynucleotide relate to a specified degree of sequence identity of the amino acid sequence or nucleotide sequence with a reference. A similar amino sequence is taken to include an amino acid sequence that is at least 80%, 85%, 86%, 87%, 88%, 89%, 90%, 91%, 92%, 93%, 94%, 95%, 96%, 97%, 98% or even 99% identical to the subject sequence. Typically, similar sequences will include the same residues in positions that are relevant for the function of the peptide or polynucleotide, such as active site residues or glycosylated amino acids, however though may include any number of conservative amino acid substitutions. A similar nucleotide sequence is taken to include a nucleotide sequence that is at least 80%, 85%, 86%, 87%, 88%, 89%, 90%, 91%, 92%, 93%, 94%, 95%, 96%, 97%, 98% or even 99% identical to the subject sequence.

"Identical" as used herein refers to an amino acid or nucleotide sequence identity to a reference sequence of 100%.

The term "recombinant" when used in reference to a cell, nucleic acid, protein or vector, indicates that the cell, nucleic acid, protein or vector has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell, or express native genes at different levels or under different conditions than found in nature.

The term "half-life" as used herein is the time required for plasma/blood concentration to decrease by 50% after pseudo-equilibrium of distribution has been reached (in accordance with the definition in Toutain et al., 2005). The term "half life" is also referred to as "circulatory half-life", "terminal half-life" or "elimination half-life".

As used herein, the terms "transformed," "stably transformed," and "transgenic," used with reference to a cell means that the cell contains a non-native (e.g. heterologous) nucleic acid sequence integrated into its genome or carried as an episome that is maintained through multiple generations.

The term "fragment" as used herein refers to a polypeptide that has an amino-terminal and/or carboxy terminal deletion of one or more amino acids as compared to the native or wild-type protein but where the remaining amino acid sequence is identical to the corresponding positions in the amino acid sequence deduced from a full-length cDNA. Fragments are typically at least 50 amino acids in length.

The term "glycosylation" as used herein refers to the attachment of glycans to molecules, for example to proteins. Glycosylation may be an enzymatic reaction. The attachment formed may be through covalent bonds. Accordingly, a glycosylated polypeptide as used herein is a polypeptide to which one or multiple glycans are attached. The phrase "highly glycosylated" refers to a molecule such as an enzyme which is glycosylated at all or nearly all of the available glycosylation sites, for instance O- linked or N-linked glycosylation sites.

The term "glycan" as used herein refers to a polysaccharide or oligosaccharide, or the carbohydrate section of a glycoprotein or glycosylated polypeptide. Glycans may be homo- or heteropolymers of monosaccharide residues. They may be linear or branched molecules. Glycans typically contain at least three sugars, and can be linear or branched. A glycan may include natural sugar residues (e.g., glucose, N-acetylglucosamine, N-acetyl neuraminic acid, N-acetylgalactosamine, galactose, mannose, fucose, arabinose, ribose, xylose, etc.) and/or modified sugars (e.g., 2'-fluororibose, 2'-deoxyribose, phosphomannose, 6'-sulfo-N-acetylglucosamine, etc.).

The term "O-glycans" as used herein refers to glycans that are generally found covalently linked to serine and threonine residues of mammalian glycoproteins. 0-glycans may be α-linked via an N-acetylgalactosamine (GalNAc) moiety to the —OH of serine or threonine by an O-glycosidic bond. Other linkages include α-linked O-fucose, β-linked O-xylose, α-linked O-mannose, β-linked O-GlcNAc (N-acetylglucosamine), α- or β-linked O-galactose, and α- or β-linked O-glucose glycans.

According to the invention, the terms "O-glycosylation cluster", "O-glycan cluster" and "cluster of O-glycosylated amino acids" are used interchangeably and related to two or more of O-glycosylated amino acids.

The term "sialylated" as used herein refers to molecules in particular glycans that have been reacted with sialic acid or its derivatives.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim, except for impurities ordinarily associated therewith. When the phrase "consists of" appears in a clause of the body of a claim, rather than immediately following the preamble, it limits only the element set forth in that clause; other elements are not excluded from the claim as a whole. The transitional phrase "consisting essentially of" limits the scope of a claim to the specified materials or steps "and those that do not materially affect the basic and novel characteristic(s)" of the claimed invention. "A 'consisting essentially of' claim occupies a middle ground between closed claims that are written in a 'consisting of' format and fully open claims that are drafted in a 'comprising' format."

In the context of the invention for practical reasons the term "glycosylated protein" such as the fusion protein is used in the singular form. Generally, in praxis, proteins occur in a composition of protein molecules of the same type. However, in the case of glycosylated proteins, glycosylation will not be identical in every molecule of the composition. For example, not all of the individual molecules of the composition may be glycosylated to 100%. Moreover, differences in the glycans bound to a specific 0-glycosylation site may arise. Accordingly, in the present application a reference to the "fusion protein" also relates to a composition of fusion protein molecules with identical amino acid sequences but variances in the O-glycan structure.

The terms "binding affinity" or "affinity" as used herein indicate the strength of the binding between two molecules, in particular a ligand and a protein target. Binding affinities are influenced by non-covalent intermolecular interactions between the two molecules such as hydrogen bonding, electrostatic interactions, hydrophobic interactions, and van der Waals forces.

An immune response as used herein relates to adaptive or innate immune response. The innate immune response refers to nonspecific defense mechanisms that are activated immediately or within hours of an antigen's appearance in the body. These mechanisms include physical barriers such as skin, chemicals in the blood, and immune system cells that attack foreign cells in the body. The innate immune response is activated by chemical properties of the antigen. The adaptive immune response refers to antigen-specific immune response. For this, the antigen first must be processed and recognized. Once an antigen has been recognized, the adaptive immune system creates a large number of immune cells specifically designed to attack that antigen.

Fusion Protein

According to a first aspect the invention provides a fusion protein comprising a main protein and at least one extension peptide, wherein the amino acid sequence of the main protein is identical or similar to the amino acid sequence of a mammalian protein or a fragment thereof, and said extension peptide comprises a cluster of O-glycosylated amino acids.

The inventors have identified a modification of proteins leading to an increase in half-life, namely the addition of an extension peptide which contains a cluster of 0-glycosylated amino acids. As shown in the examples, the fusion of O-glycosylation cluster 1 of human VWF as extension peptide to a fragment of VWF leads to a fusion protein (OCTA 12) with an increased half-life as compared to the VWF fragment (OCTA 11) alone.

The half-life ($t_{1/2}$) may be calculated by linear regression analysis of the log-linear portion of the individual plasma concentration-time curves or by non-linear regression using one-phase exponential decay model. Exemplary software programs for calculation are GraphPad Prism version 6.07 (La Jolla, CA 92037 USA) and WinNonlin, version 6.4 (Pharsight Corporation, Mountain View, CA, USA).

The calculations are based on the following equations:

$$t_{\frac{1}{2}} = \frac{\ln 2}{K_{el}} \ [h]$$

$$\frac{dc}{dt} = K_{el} \cdot c \ [h]$$

$K_{el}$=elimination rate constant
$t_{1/2}$=elimination half-life
c=concentration
t=time Thus, according to one embodiment, the fusion protein has an increased half-life compared to the main protein without extension peptide.

As it was possible to increase the half-life of a VWF fragment with a cluster of glycosylated amino acids derived from the VWF, the inventors have identified a novel principle for half-life prolongation. That is, the increase in half-life of a protein or fragment of a protein by addition of a cluster of O-glycosylated amino acids that is also present in the naturally occurring protein.

Thus, according to one embodiment of the fusion protein, the amino acid sequence of the one or more extension peptide is identical or similar to a section of said mammalian protein. This section of the mammalian protein is in particular a non-repeated amino acid sequence.

A non-repeated amino acid sequence as used herein is a sequence that is found in only one copy in a naturally occurring mammalian protein according to the invention. Thus, the non-repeated amino acid sequence explicitly excludes any repeated sequences naturally occurring in proteins. A sequence is in particular considered repeated if the sequence consists of more than 20 amino acids, preferably more than 15 amino acids, more preferably more than 10 amino acids, and the mammalian protein contains more than one of this sequence.

Repeated sequences can be derived from so-called variable number tandem repeats. A variable number tandem repeat (VNTR) is a location in a genome where a short nucleotide sequence is organized as a "tandem repeat". "Tandem repeats" occur in DNA when a pattern of one or more nucleotides is repeated and the repetitions are directly adjacent to each other. VNTRs are found on many chromosomes, and often show variations in length between individuals. In case tandem repeats are located in protein coding DNA sequences, these lead to amino acid sequence repeats. Examples are the tandem repeats found in all members of the mucin protein family. Mucins are a family of high molecular weight, heavily glycosylated proteins produced by epithelial tissues in most organisms of the animal kingdom. A non-repeated amino acid sequence according to the invention explicitly excludes such amino acid sequence tandem repeats, in particular the mucin tandem repeats.

The extension peptide may not only be derived from the same mammalian protein as the main protein but more specifically may contain a section that is also present in the main protein. Thus, according to one embodiment, the amino acid sequence of the one or more extension peptide is identical or similar to a non-repeated amino acid sequence section of said main protein.

Preferably, the one or more extension peptides are not derived from chorionic gonadotropin β-subunit (CG-β). The C-terminal peptide (CTP) of the chorionic gonadotropin β-subunit was shown to increase the half-life of other proteins such as FSH, FVIIa, and FIX. However, for the case that an hCG has been described with an additional CTP, i.e. more than one CTP copy, this protein is specifically excluded from the subject matter of the invention. Thus, in particular the extension peptide is not identical or similar to the CTP of CG-β.

According to the present invention, two or more O-glycosylated amino acids in close proximity of the amino acid sequence are considered as a cluster. Thus, according to one embodiment of the fusion protein, the cluster of O-glycosylated amino acids of the at least one extension peptide contains at least two O-glycosylated amino acids. The cluster may contain for example 2, 3, 4, 5, 6, 7, 8, 9, 10, 11, 12, 13, 14, or 15 O-glycosylated amino acids.

According to theory, the half-life extending effect is based on the negative charge of the O-glycans. Thus, the effect of half-life prolongation should increase with the number of O-glycosylated amino acids in the cluster. Thus, the cluster preferably contains at least three O-glycosylated amino acids. As shown in the Examples a significant half-life propagation effect was achieved with an extension peptide with a cluster of four O-glycosylated amino acids. Thus, according to a preferred embodiment the cluster contains at least four O-glycosylated amino acids.

In addition to the O-glycosylated amino acids of a cluster also N-glycosylated amino acids may be present. Preferably there are no N-glycosylated amino acids in the O-glycosylation cluster.

In case more than one extension peptide is present, the clusters of the extension peptides may have different numbers of O-glycosylated amino acids. For example, the fusion protein may contain one cluster with two and a second cluster with four O-glycosylated amino acids. Furthermore, one cluster may contain three O-glycosylation sites and the other four O-glycosylation sites.

The O-glycosylated amino acids of the extension peptide can be the mucin-type O-glycosylated amino acids serine (Ser) and threonine (Thr). However, also O-glycosylated tyrosine (Tyr), hydroxylysine (Hydroxy-Lys) or hydroxyproline (Hydroxy-Pro) are known in the art. Thus, the one or more O-glycosylated amino acids in the fusion protein, in particular in the extension peptide, may be selected from Ser, Thr, Tyr, Hydroxy-Lys and Hydroxy-Pro.

The extension peptide fused to the VWF fragment in OCTA 12, which leads to a half-life prolongation of said fragment, contains both O-glycosylated threonine residues and serine residues. Thus, according to one embodiment of the first aspect, the cluster of O-glycosylated amino acids contains at least one O-glycosylated threonine. Preferably, said cluster contains both a threonine and a serine as O-glycosylated amino acids. Interestingly, the extension peptide of OCTA 12 contains two vicinal threonine residues that are O-glycosylated. Thus, in one embodiment the extension peptide contains at least two vicinal O-glycosylated threonine residues.

As explained above, it is believed that the negative charge of the protein surface generated by the O-glycans leads to the half-life prolongation. Without wanting to be bound to the theory, it is believed that for manifestation of the effect two or more O-glycans in close proximity are needed. The effect may become weakened or abolished if the gaps between the O-glycans are too large, i.e. with less than one O-glycosylated amino acid in 15 amino acids. Thus, according to one embodiment of the fusion protein, the at least one extension peptide contains at least one O-glycosylated amino acid in 15 amino acids.

More preferably, the at least one extension peptide contains at least one 0-glycosylation site in 10 amino acids. As shown in the examples, the tested extension peptide contains clusters with one O-glycosylation site in 8 amino acids. Thus, according to a preferred embodiment the one or more clusters contain at least one glycosylation site in 8 amino acids.

The length of the extension peptide is defined by two different aspects. The extension peptide must be long enough to contain the recognition sites facilitating the glycosylation of the O-glycosylated amino acids. Thus, the extension peptide should be at least 10 amino acids in length. On the other hand, the shorter the extension peptide is, the less likely it is to interfere with the structural integrity or activity and thus the therapeutic effect of the main protein. Thus, the extension peptide should not exceed 100 amino acids. According to one embodiment the one or more extension peptides have a length in the range from 15 to 60 amino acids. In order to allow four amino acids to be O-glycosylated within the extension peptide, the length is preferably in the range from 22 to 40 amino acids. More preferably, the length of the extension peptide is about the length of the extension peptides in OCTA 12, i.e. in the range from 26 to 36 amino acids. According to one embodiment the one or more extension peptides have a length of about 31 amino acids.

The findings of the present inventors do not only lead to the conclusion of the principle of adding one or more copies of an O-glycosylated peptide naturally present in a protein to increase the half-life of that same protein or fragment thereof. Additionally, the presented results make it credible that the specific O-glycosylated peptide of VWF—in analogy to the CTP—can increase the half-life of other proteins, i.e. of proteins in general.

Thus, according to one embodiment, the one or more extension peptides have a sequence identity of at least 90% to an O-glycosylated peptide of human VWF. This human VWF derived extension peptide may be fused to other mammalian proteins or fragments thereof, such as FVIII. The sequence identity of the one or more extension peptides is preferably at least 95% to an O-glycosylated peptide of human VWF. More preferably the sequence identity is at least 98%. Most preferably the sequence of an extension peptide is identical to an O-glycosylated peptide of human VWF.

The O-glycosylated peptide of human VWF includes preferably at least partially O-glycosylation cluster 2 of VWF (amino acids 1238-1268 of SEQ ID NO: 2): QEPG-GLVVPPTDAPVSPTTLYVEDISEPPLH (SEQ ID NO: 1) or a variant thereof. Thus, according to one embodiment, the extension peptide has a sequence identity to SEQ ID NO: 1 of at least 90%. The sequence identity to SEQ ID NO: 1 is preferably at least 95%. More preferably, the sequence identity of the extension peptide to SEQ ID NO: 1 is at least 98%. Most preferably, the one or more extension peptides have a sequence identity to SEQ ID NO: 1 of 100%.

The main protein is based on a mammalian protein, i.e. contains an amino acid sequence similar or identical to a mammalian protein or fragment thereof. The mammalian protein is in particular a human protein.

The mammalian protein to which the amino acid sequence of the main protein is similar or identical to may be a glycosylated protein. According to one embodiment of the fusion protein, the main protein comprises a glycosylated section of the mammalian protein. According to another embodiment, the main protein comprises at least one cluster of O-glycosylated amino acids. This cluster of O-glycosylated amino acids may be identical to the cluster of O-glycosylated amino acids in the extension peptide.

The mammalian protein, on which the main protein is based, is more preferably a blood protein. According to one embodiment, the mammalian protein is a human blood protein.

The mammalian blood protein may be a blood clotting factor, a transport protein, a protease inhibitor, an immunoglobulin, a cell related plasma protein, an apolipoprotein, a complement factor, a growth factor, an antiangiogenic protein, a highly glycosylated protein, a blood factor or another blood protein.

The blood clotting factor, in particular human blood clotting factor, is preferably selected from the group consisting of fibrinogen (FI), prothrombin (FII), tissue factor (FIII), FV, FVII, FVIII, FIX, FX, FXI, FXII, and FXIII, VWF, and ADAMTS13.

It is appreciated that the clotting factors FI, FII, FV, FVII, FVIII, FIX, FX, FXI, FXII, and FXIII can be in a non-active or an activated form. Thus, in the context of the invention, a reference to FI, FII, FV, FVII, FVIII, FIX, FX, FXI, FXII, and FXIII includes the activated forms FIa (fibrin), FIIa (thrombin), FVa, FIXa, FVIIa, FVIIIa, FXa, FXIa, FXIIa, and FXIIIa, respectively unless explicitly stated otherwise or from the context, the activated form is logically excluded. Thus, e.g. in this context FI, FII, FV, FIX, FVII, FVIII, FX, FXI, FXII, and FXIII may be read as FI/FIa, FII/FIIa, FV/FVa, FVII/FVIIa, FVIII/FVIIIa, FIX/FXIa, FX/FXa, FXI/FXIa, FXII/FXIIa, and FXIII/FXIIIa.

The transport protein, in particular human transport protein, may be selected from albumin, transferrin, ceruloplasmin, haptoglobin, hemoglobin, and hemopexin.

According to one embodiment the mammalian protein is a protease inhibitor, in particular human protease inhibitor. Examples of such protease inhibitors are β-antithrombin, α-antithrombin, pre-latent-antithrombin, oxidized-antithrombin, 2-macroglobulin, C1-inhibitor, tissue factor pathway inhibitor (TFPI), heparin cofactor II, protein C inhibitor (PAI-3), Protein C, Protein S, and Protein Z.

Examples of immunoglobulin's such as polyclonal antibodies (IgG), monoclonal antibodies, IgG1, IgG2, IgG3, IgG4, IgA, IgA1, IgA2, IgM, IgE, IgD, and Bence Jones protein.

The cell related plasma protein may be for example, fibronectin, thromboglobulin, or platelet factor 4. Examples of apolipoproteins are apo A-I, apo A-II, and apo E.

Complement factors according to the invention are e.g. Factor B, Factor D, Factor H, Factor I, C3b-Inactivator, properdin, C4-binding protein etc.

Examples of growth factors include Platelet derived growth factor (PDGF), Epidermal growth factor (EGF), Transforming growth factor alfa (TGF-α), Transforming growth factor beta (TGF-α), Fibroblast growth factor (FGF) and Hepatocyte growth factor (HGF).

Antiangionetic proteins include latent-antithrombin, prelatent-antithrombin, oxidized-antithrombin and plasminogen.

Examples of highly glycosylated proteins are alfa-1-acid glycoprotein, antichymotrypsin, inter-α-trypsin inhibitor, α-2-HS glycoprotein, C-reactive protein, Blood factors may be, e.g., erythropoeitin, interferon, tumor factors, tPA, or gCSF.

Other human blood proteins include histidine-rich glycoprotein, mannan binding lectin, C4-binding protein, fibronectin, GC-globulin, plasminogen/plasmin, α-1 microglobulin, C-reactive protein.

The mammalian protein is in particular selected from human VWF, fibrinogen, prothrombin, FIII, FV, FVII, FVIII, FIX, FX, FXI, FXII, FXIII, ADAMTS13, antithrombin, alpha-1 antitrypsin, C1-inhibitor, antichymotrypsin, PAI-1, PAI-3, 2-macroglobulin, TFPI, heparin cofactor II, Protein Z, Protein C, and Protein S.

Factor VIII in humans is coded by the F8 gene which comprises 187.000 base pairs in six exons. The transcribed mRNA has a length of 9.029 base pairs and is translated to a protein with 2.351 amino acids from which 19 amino acids are removed. The FVIII molecule in humans is glycosylated on 31 amino acids, with 25 N-glycosylations, and 6 O-glycosylations (see Kannicht et al., 2013).

After translation, the amino acid chain is cleaved by specific proteases in positions leading to the formation of a heavy chain with about 200 kDa and a light chain with about 80 kDa. The domain organization is typically characterized as A1-A2-B-A3-C1-C2. The light chain is a made-up of domains A3-C1-C2. The heavy chain is in principal composed of the domains A1-A2-B. Heavy chains found in plasma have a heterogeneous composition with molecular weights varying from 90 to 200 kDa. The reason for this are the heterogeneity in its glycosylation, the existence of splice variants and existence of proteolytic products such the B domain depleted heavy chain A1-A2. The amino acid sequence of the full length FVIII is identified by amino acids 20 to 2.351 of P00451 of UniProtKB, sequence version 1 of Jul. 21, 1986 (in the following UniProtKB P00451.1).

According to one embodiment the mammalian protein, to which the main protein is similar or identical, is human full length FVIII identified by amino acids 20 to 2.351 of UniProtKB P00451.1. According to another embodiment the main protein is FVIII, in which at least part of the B-domain is missing. In this regard the entire B-domain may be missing. The missing part of the B-domain is optionally replaced by a linker. The linker sequence has in particular the following amino acids sequence SFSQNSRHQAYRYRRG (SEQ ID NO: 12). An example of a FVIII in which the B-domain is replaced by a linker, is Simoctocog alfa, the active ingredient of NUWIQ® (human coagulation factor VIII) or VIHLUMA® (human coagulation factor VIII). Simoctocog alfa has the following sequence:

(SEQ ID NO: 13)
ATRRYYLGAVELSWDYMQSDLGELPVDARFPPRVPKSFPFNTSVVYKKTL

FVEFTDHLFNIAKPRPPWMGLLGPTIQAEVYDTVVITLKNMASHPVSLHA

VGVSYWKASEGAEYDDQTSQREKEDDKVFPGGSHTYVWQVLKENGPMASD

PLCLTYSYLSHVDLVKDLNSGLIGALLVCREGSLAKEKTQTLHKFILLFA

VFDEGKSWHSETKNSLMQDRDAASARAWPKMHTVNGYVNRSLPGLIGCHR

KSVVWHVIGMGTTPEVHSIFLEGHTFLVRNHRQASLEISPITFLTAQTLL

MDLGQFLLECHISSHQHDGMEAYVKVDSCPEEPQLRMKNNEEAEDYDDDL

TDSEMDVVREDDDNSPSFIQIRSVAKKHPKTWVHYIAAEEEDWDYAPLVL

APDDRSYKSQYLNNGPQRIGRKYKKVRFMAYTDETFKTREAIQHESGILG

PLLYGEVGDTLLIIFKNQASRPYNTYPHGITDVRPLYSRRLPKGVKHLKD

FPILPGEIFKYKWTVTVEDGPTKSDPRCLTRYYSSFVNMERDLASGLIGP

LLICYKESVDQRGNQIMSDKRNVILFSVFDENRSWYLTENIQRFLPNPAG

VQLEDPEFQASNIMHSINGYVFDSLQLSVCLHEVAYWYILSIGAQTDFLS

VFFSGYTFKHKMVYEDTLTLFPFSGETVFMSMENPGLWILGCHNSDFRNR

GMTALLKVSSCDKNTGDYYEDSYEDISAYLLSKNNAIEPRSFSQNSRHQA

YRYRRGEITRTTLQSDQEEIDYDDTISVEMKKEDFDIYDEDENQSPRSFQ

KKTRHYFIAAVERLWDYGMSSSPHVLRNRAQSGSVPQFKKVVFQEFTDGS

FTQPLYRGELNEHLGLLGPYIRAEVEDNIMVTFRNQASRPYSFYSSLISY

EEDQRQGAEPRKNEVKPNETKTYFWKVQHHMAPTKDEFDCKAWAYESDVD

LEKDVHSGLIGPLLVCHTNTLNPAHGRQVTVQEFALFFTIFDETKSWYFT

ENMERNCRAPCNIQMEDPITKENYRFHAINGYIMDTLPGLVMAQDQRIRW

YLLSMGSNENIHSIHFSGHVETVRKKEEYKMALYNLYPGVFETVEMLPSK

AGIWRVECLIGEHLHAGMSTLFLVYSNKCQTPLGMASGHIRDFQITASGQ

YGQWAPKLARLHYSGSINAWSTKEPFSWIKVDLLAPMIIHGIKTQGARQK

FSSLYISQFIIMYSLDGKKWQTYRGNSTGTLMVFFGNVDSSGIKHNIFNP

PIIARYIRLHPTHYSIRSTLRMELMGCDLNSCSMPLGMESKAISDAQITA

SSYFTNMFATWSPSKARLHLQGRSNAWRPQVNNPKEWLQVDFQKTMKVTG

-continued

VTTQGVKSLLTSMYVKEFLISSSQDGHQWTLFFQNGKVKVFQGNQDSFTP

VVNSLDPPLLTRYLRIHPQSWVHQIALRMEVLGCEAQDLY

VWF is a multimeric adhesive glycoprotein present in the plasma of mammals, which has multiple physiological functions. During primary hemostasis, VWF acts as a mediator between specific receptors on the platelet surface and components of the extracellular matrix such as collagen. Moreover, VWF serves as a carrier and stabilizing protein for pro-coagulant Factor VIII. VWF is synthesized in endothelial cells and megakaryocytes as a 2813 amino acid precursor molecule.

The domain organization of VWF is typically characterized as TiI3-D3-TIL4-A1-A2-A3-D4-C1-C2-C3-CK.

The precursor polypeptide, pre-pro-VWF, consists of a 22-residue signal peptide, a 741-residue pro-peptide (domains D1-D2) and the 2050-residue polypeptide found in mature plasma Von Willebrand Factor (Fischer et al., 1994). Full length VWF is identified by entry P04275 of UniprotKB (entry version 224 of Apr. 12, 2017).

The human VWF according to the present invention has an amino acid sequence of any of the sequences said UniprotKB P04275, in particular SEQ ID NO: 2 (isoform 1). VWF contains two clusters of O-glycosylated amino acids. The first clusters of O-glycosylated amino acid is found between amino acids 1238 to 1268 of SEQ ID NO: 2. The second cluster includes amino acids 1468 to 1487 of SEQ ID NO: 2.

Upon secretion into plasma, VWF circulates in the form of various species with different molecular sizes. These VWF molecules consist of oligo- and multimers of the mature subunit of 2050 amino acid residues. VWF can be usually found in plasma as multimers ranging in size approximately from 500 to 20.000 kDa (Furlan et al., 1996).

According to one embodiment, the main protein has an amino acid sequence that is identical or similar to the sequence of human mature VWF.

According to another embodiment the main protein has an amino acid sequence that is similar or identical to the sequence of a fragment of human VWF.

For example, in the fragment of human VWF one or more of the domains A1, A2, A3, D4, C1, C2, C3, CK may be missing relative to the human mature VWF (TiI3-D3-TIL4-A1-A2-A3-D4-C1-C2-C3-CK). The fragment VWF fragment may, for example, have a domain organization selected from the following group consisting of TiI3-D3-TIL4-A1, TiI3-D3-TIL4-A1-A2, TiI3-D3-TIL4-A1-A2-A3, TiI3-D3-TIL4-A1-A2-A3-D4, TiI3-D3-TIL4-A1-A2-A3-D4-C1, TiI3-D3-TIL4-A1-A2-A3-D4-C1-C2, and TiI3-D3-TIL4-A1-A2-A3-D4-C1-C2-C3-CK.

In this regard the fragment of human VWF is in particular a fragment starting with amino acid 764 of SEQ ID NO: 2. Amino acids 764 to 1035 of SEQ ID NO: 2 comprise the FVIII binding domain of VWF.

The main protein may for example contain a fragment of VWF as defined in WO 2015/185758 A2. As shown in WO 2015/185758 A2, the complex of FVIII and the VWF fragments as defined therein exhibit a reduced binding to phospholipids membranes compared to FVIII alone as well as a reduced binding to collagen III and heparin compared to the complex of FVIII and full length VWF.

The fragment of VWF preferably starting with amino acid 764 of SEQ ID NO: 2 preferably ends with an amino acid of SEQ ID NO: 2 in the range from 1905 to 2153. According to one embodiment the VWF fragment ends with an amino acid of VWF in the range from 2030 to 2153 of SEQ ID NO: 2. According to a further embodiment the VWF fragment ends with an amino acid of SEQ ID NO: 2 in the range from 2100 to 2153.

According to one embodiment the main protein has an amino acid sequence that is similar or identical to amino acids 764 to 1268 of SEQ ID NO: 2. According to one embodiment the amino acid sequence of the main has an identity of at least 90%, to amino acids 764 to 1268 of SEQ ID NO: 2. The amino acid sequence of the main protein may also have an identity of at least 95% to amino acids 764 to 1268 of SEQ ID NO: 2. Furthermore, the identity to amino acids 764 to 1268 of SEQ ID NO: 2 of the amino acid sequence of the main protein may be at least 98%. In particular, the amino acid sequence of the main protein may have an identity to amino acids 764 to 1268 of SEQ ID NO:2 of 100%.

According to one embodiment the main protein has an amino acid sequence that is similar or identical to amino acids 764 to 1905 of SEQ ID NO: 2. According to one embodiment the amino acid sequence of the main has an identity of at least 90%, to amino acids 764 to 1905 of SEQ ID NO: 2. The amino acid sequence of the main protein may also have an identity of at least 95% to amino acids 764 to 1905 of SEQ ID NO: 2. Furthermore, the identity to amino acids 764 to 1905 of SEQ ID NO: 2 of the amino acid sequence of the main protein may be at least 98%. In particular, the amino acid sequence of the main protein may have an identity to amino acids 764 to 1905 of SEQ ID NO: 2 of 100%.

The fusion protein may contain any number of extension peptides, such as one, two, three, four, five, six, seven, eight, nine, or ten extension peptides. The fusion protein OCTA 12 contains two copies of the extension peptide and exhibits a significant increase in half-life as compared to the VWF fragment OCTA 11. Thus, according to one embodiment the fusion protein contains at least two extension peptides.

It is presently understood that the half-life prolongation effect is at least partially based on the negative charge of the O-glycans of the extension peptide. Thus, an increase in the copy number of the extension peptide leads to a further increase of the effect of half-life prolongation. This is confirmed by OCTA 14, which contains four copies of the extension peptide. Thus, according to one embodiment the fusion protein contains at least four extension peptides.

On the other hand, with the copy number of the extension peptide, the chance increases that the extension peptides interfere with the structural integrity or activity and, thus, the therapeutic effect of the main protein. Therefore, according to one embodiment the number of extension peptides is below 11.

The fusion protein may comprise further peptide components in addition to the main protein and the extension peptides. In particular, in addition to the extension peptide according to the invention the fusion protein may contain further peptides for half-life prolongation, such as CTP, XTEN, transferrin or fragments thereof, albumin or fragments thereof.

It is also possible that the main protein is a fragment of a mammalian protein and the fusion protein contains a further fragment of the same mammalian protein. In particular the two fragments are separated by one or more extension peptides. An example of such a protein is OCTA 15, which contains amino acids 764 to 1268 of VWF, two extension peptides with the sequence SEQ ID NO: 1 and the "cystein knot domain" of VWF consisting of amino acids 2721 to 2813 of SEQ ID NO: 2.

In the fusion protein, one or more extension peptides may be linked to the N-terminus or C-terminus of the main protein. Specifically, the fusion protein may contain one or more extension peptides linked to the N-terminus and one or more extension peptides linked to the C-terminus of the main protein.

As the fusion protein may contain further peptides in addition to the main protein and the one or more extension peptides. Accordingly, the extension peptides may be directly or indirectly linked to the main protein. In this regard, "directly linked" means that the amino acid sequences of the main protein and an extension peptide are directly adjacent. "Indirectly linked" means that between the main protein and the extension peptide a further peptide is located. In particular, a linker peptide could be located between the main protein and the extension peptide. The linker may contain a cleavage site, making the extension peptide cleavable from the main protein. The main protein, the one or more extension peptides and optionally the further peptides may be produced by joining of the genes, cDNAs, or sequences encoding them. Accordingly, the main protein, the one or more extension peptides and optionally the further peptides are linked by peptide bonds. According to the invention, the peptides of the fusion protein may instead be connected via other linkers such as chemical linkers or glycosidic bonds. Preferably, the peptides of the fusion protein are connected by peptide bonds.

According to one embodiment an extension peptide is directly linked to the C-terminus of the main protein. In particular, the fusion protein contains at least two consecutive extension peptides linked to the C-terminus of the main protein.

The fusion protein may be linked to two one or more affinity tags. Examples of affinity tags are polyhistidine, protein A, glutathione S transferase, substance P, FLAG, streptavidin, and an immunoglobulin heavy chain constant region. While the affinity tag generally forms part of the amino acid sequence of the full construct, the affinity tag is not considered as part of the fusion protein. The one or more affinity tags are preferably linked to the C-terminus or the N-terminus of the fusion protein. In case the fusion protein is linked to one or more affinity tags, the fusion protein preferably contains a cleavage site between the affinity tag and the rest of the protein making the affinity tag cleavable, e.g. by protease cleavage.

According to one embodiment, one extension peptide forms the N-terminus of the fusion protein. As explained above the N-terminal amino acid of said extension peptide is optionally linked to an affinity tag. According to one embodiment, one extension peptide forms the C-terminus of the fusion protein. As explained above the C-terminal amino acid of said extension peptide is optionally linked to an affinity tag.

According to one embodiment the fusion protein according to any of the preceding claims, wherein the fusion protein comprises at least 4, preferably at least 8, more preferably at least 12 additional O-glycans compared to the main protein.

According to one embodiment the fusion protein comprises a dimerization domain; in particular the main protein comprises a dimerization domain. In VWF, the dimers are formed by the binding of the CK-domains. Thus, in case the main protein is a VWF fragment, it preferably comprises the CK-domain.

A representative fusion protein according to the invention is OCTA 12. OCTA 12 has the following amino acid sequence (SEQ ID NO: 3):

```
SLSCRPPMVKLVCPADNLRAEGLECTKTCQNYDLECMSMGCVSGCLCPPG
MVRHENRCVALERCPCFHQGKEYAPGETVKIGCNTCVCQDRKWNCTDHVC
DATCSTIGMAHYLTFDGLKYLFPGECQYVLVQDYCGSNPGTFRILVGNKG
CSHPSVKCKKRVTILVEGGEIELFDGEVNVKRPMKDETHFEVVESGRYII
LLLGKALSVVWDRHLSISVVLKQTYQEKVCGLCGNFDGIQNNDLTSSNLQ
VEEDPVDFGNSWKVSSQCADTRKVPLDSSPATCHNNIMKQTMVDSSCRIL
TSDVFQDCNKLVDPEPYLDVCIYDTCSCESIGDCACFCDTIAAYAHVCAQ
HGKVVTWRTATLCPQSCEERNLRENGYECEWRYNSCAPACQVTCQHPEPL
ACPVQCVEGCHAHCPPGKILDELLQTCVDPEDCPVCVAGRRFASGKKVTL
NPSDPEHCQICHCDVVNLTCEACQEPGGLVVPPTDAPVSPTTLYVEDISE
PPLHQEPGGLVVPPTDAPVSPTTLYVEDISEPPLHQEPGGLVVPPTDAPV
SPTTLYVEDISEPPLH
```

OCTA 12 is a fusion protein of the VWF fragment of amino acids 764 to 1268 of SEQ ID NO: 2 and two copies of an extension peptide (bold) bound to the C-terminus consisting of the amino acids 1238 to 1268 of SEQ ID NO: 2.

According to one embodiment the amino acid sequence of the fusion protein has an identity of at least 90% to SEQ ID NO: 3. The amino acid sequence of the fusion protein may also have an identity of at least 95% to SEQ ID NO: 3. Furthermore, the identity to SEQ ID NO: 3 of the amino acid sequence of the fusion protein may be at least 98%. In particular, the amino acid sequence of the fusion protein may have an identity to SEQ ID NO: 3 of 100%.

The following sequence (SEQ ID NO: 4) represents OCTA 12 with an additional 12 amino acid signal peptide (bold and underlined). An expression of this peptide provides a monomeric form of OCTA 12. The signal peptide is cleaved off.

```
                                        (SEQ ID NO: 4)
MIPARFAGVLLALALILPGTLCSLSCRPPMVKLVCPADNLRAEGLECTKT
CQNYDLECMSMGCVSGCLCPPGMVRHENRCVALERCPCFHQGKEYAPGET
VKIGCNTCVCQDRKWNCTDHVCDATCSTIGMAHYLTFDGLKYLFPGECQY
VLVQDYCGSNPGTFRILVGNKGCSHPSVKCKKRVTILVEGGEIELFDGEV
NVKRPMKDETHFEVVESGRYIILLLGKALSVVWDRHLSISVVLKQTYQEK
VCGLCGNFDGIQNNDLTSSNLQVEEDPVDFGNSWKVSSQCADTRKVPLDS
SPATCHNNIMKQTMVDSSCRILTSDVFQDCNKLVDPEPYLDVCIYDTCSC
ESIGDCACFCDTIAAYAHVCAQHGKVVTWRTATLCPQSCEERNLRENGYE
CEWRYNSCAPACQVTCQHPEPLACPVQCVEGCHAHCPPGKILDELLQTCV
DPEDCPVCVAGRRFASGKKVTLNPSDPEHCQICHCDVVNLTCEACQEPGG
LVVPPTDAPVSPTTLYVEDISEPPLHQEPGGLVVPPTDAPVSPTTLYVED
ISEPPLHQEPGGLVVPPTDAPVSPTTLYVEDISEPPLH
```

According to one embodiment the amino acid sequence of the fusion protein has an identity of at least 90% to SEQ ID NO: 4. The amino acid sequence of the fusion protein may also have an identity of at least 95% to SEQ ID NO: 4. Furthermore, the identity to SEQ ID NO: 4 of the amino acid sequence of the fusion protein may be at least 98%. In particular, the amino acid sequence of the fusion protein may have an identity to SEQ ID NO: 4 of 100%.

A further representative fusion protein according to the invention is Pro-OCTA 12 including OCTA 12 and a pro-peptide (bold) with a signal peptide (bold and underlined). Pro-OCTA 12 is identified by SEQ ID NO: 5:

(SEQ ID NO: 5)
<u>MIPARFAGVLLALALILPGTLC</u>AEGTRGRSSTARCSLEGSDEVNTEDGSM

YSFAGYCSYLLAGGCQKRSFSIIGDFQNGKRVSLSVYLGEFFDIHLFVNG

TVTQGDQRVSMPYASKGLYLETEAGYYKLSGEAYGFVARIDGSGNFQVLL

SDRYFNKTCGLCGNENIFAEDDFMTQEGTLTSDPYDFANSWALSSGEQWC

ERASPPSSSCNISSGEMQKGLWEQCQLLKSTSVFARCHPLVDPEPFVALC

EKTLCECAGGLECACPALLEYARTCAQEGMVLYGWTDHSACSPVCPAGME

YRQCVSPCARTCQSLHINEMCQERCVDGCSCPEGQLLDEGLCVESTECPC

VHSGKRYPPGTSLSRDCNTCICRNSQWICSNEECPGECLVTGQSHFKSFD

NRYFTFSGICQYLLARDCQDHSFSIVIETVQCADDRDAVCTRSVTVRLPG

LHNSLVKLKHGAGVAMDGQDVQLPLLKGDLRIQHTVTASVRLSYGEDLQM

DWDGRGRLLVKLSPVYAGKTCGLCGNYNGNQGDDFLTPSGLAEPRVEDFG

NAWKLHGDCQDLQKQHSDPCALNPRMTRFSEEACAVLTSPTFEACHRAVS

PLPYLRNCRYDVCSCSDGRECLCGALASYAAACAGRGVRVAWREPGRCEL

NCPKGQVYLQCGTPCNLTCRSLSYPDEECNEACLEGCFCPPGLYMDERGD

CVPKAQCPCYYDGEIFQPEDIFSDHHTMCYCEDGFMHCTMSGVPGSLLPD

AVLSSPLSHRSKRSLSCRPPMVKLVCPADNLRAEGLECTKTCQNYDLECM

SMGCVSGCLCPPGMVRHENRCVALERCPCFHQGKEYAPGETVKIGCNTCV

CQDRKWNCTDHVCDATCSTIGMAHYLTFDGLKYLFPGECQYVLVQDYCGS

NPGTFRILVGNKGCSHPSVKCKKRVTILVEGGEIELFDGEVNVKRPMKDE

THFEVVESGRYIILLLGKALSVVWDRHLSISVVLKQTYQEKVCGLCGNFD

GIQNNDLTSSNLQVEEDPVDFGNSWKVSSQCADTRKVPLDSSPATCHNNI

MKQTMVDSSCRILTSDVFQDCNKLVDPEPYLDVCIYDTCSCESIGDCACF

CDTIAAYAHVCAQHGKVVTWRTATLCPQSCEERNLRENGYECEWRYNSCA

PACQVTCQHPEPLACPVQCVEGCHAHCPPGKILDELLQTCVDPEDCPVCE

VAGRRFASGKKVTLNPSDPEHCQICHCDVVNLTCEACQEPGGLVVPPTDA

PVSPTTLYVEDISEPPLHQEPGGLVVPPTDAPVSPTTLYVEDISEPPLHQ

EPGGLVVPPTDAPVSPTTLYVEDISEPPLH

Expression of Pro-OCTA 12 results in the formation of dimers. The peptide dimers remain after cleavage of the propeptide.

According to one embodiment the amino acid sequence of the fusion protein has an identity of at least 90%, to SEQ ID NO: 5. The amino acid sequence of the fusion protein may also have an identity of at least 95% to SEQ ID NO: 5. Furthermore, the identity to SEQ ID NO: 5 of the amino acid sequence of the fusion protein may be at least 98%. In particular, the amino acid sequence of the fusion protein may have an identity to SEQ ID NO: 5 of 100%.

A further representative fusion protein according to the invention is OCTA 14. OCTA 14 has the following amino acid sequence:

(SEQ ID NO: 6)
SLSCRPPMVKLVCPADNLRAEGLECTKTCQNYDLECMSMGCVSGCLCPPG

MVRHENRCVALERCPCFHQGKEYAPGETVKIGCNTCVCQDRKWNCTDHVC

DATCSTIGMAHYLTFDGLKYLFPGECQYVLVQDYCGSNPGTFRILVGNKG

CSHPSVKCKKRVTILVEGGEIELFDGEVNVKRPMKDETHFEVVESGRYII

LLLGKALSVVWDRHLSISVVLKQTYQEKVCGLCGNFDGIQNNDLTSSNLQ

VEEDPVDFGNSWKVSSQCADTRKVPLDSSPATCHNNIMKQTMVDSSCRIL

TSDVFQDCNKLVDPEPYLDVCIYDTCSCESIGDCACFCDTIAAYAHVCAQ

HGKVVTWRTATLCPQSCEERNLRENGYECEWRYNSCAPACQVTCQHPEPL

ACPVQCVEGCHAHCPPGKILDELLQTCVDPEDCPVCVAGRRFASGKKVTL

NPSDPEHCQICHCDVVNLTCEACQEPGGLVVPPTDAPVSPTTLYVEDISE

PPLHQEPGGLVVPPTDAPVSPTTLYVEDISEPPLHQEPGGLVVPPTDAPV

SPTTLYVEDISEPPLHQEPGGLVVPPTDAPVSPTTLYVEDISEPPLHQEP

GGLVVPPTDAPVSPTTLYVEDISEPPLH

OCTA 14 is a fusion protein of the VWF fragment of amino acids 764 to 1268 of SEQ ID NO: 2 and four copies of an extension peptide (bold) bound to the C-terminus consisting of the amino acids 1238 to 1268 of SEQ ID NO: 2.

According to one embodiment the amino acid sequence of the fusion protein has an identity of at least 90% to SEQ ID NO: 6. The amino acid sequence of the fusion protein may also have an identity of at least 95% to SEQ ID NO: 6. Furthermore, the identity to SEQ ID NO: 6 of the amino acid sequence of the fusion protein may be at least 98%. In particular, the amino acid sequence of the fusion protein may have an identity to SEQ ID NO: 6 of 100%.

The following sequence (SEQ ID NO: 7) represents OCTA 14 with an additional 12 amino acid signal peptide (bold and underlined). An expression of this peptide provides a monomeric form of OCTA 14. The signal peptide is cleaved off.

(SEQ ID NO: 7)
<u>MIPARFAGVLLALALILPGTLC</u>SLSCRPPMVKLVCPADNLRAEGLECTKT

CQNYDLECMSMGCVSGCLCPPGMVRHENRCVALERCPCFHQGKEYAPGET

VKIGCNTCVCQDRKWNCTDHVCDATCSTIGMAHYLTFDGLKYLFPGECQY

VLVQDYCGSNPGTFRILVGNKGCSHPSVKCKKRVTILVEGGEIELFDGEV

NVKRPMKDETHFEVVESGRYIILLLGKALSVVWDRHLSISVVLKQTYQEK

VCGLCGNFDGIQNNDLTSSNLQVEEDPVDFGNSWKVSSQCADTRKVPLDS

SPATCHNNIMKQTMVDSSCRILTSDVFQDCNKLVDPEPYLDVCIYDTCSC

ESIGDCACFCDTIAAYAHVCAQHGKVVTWRTATLCPQSCEERNLRENGYE

CEWRYNSCAPACQVTCQHPEPLACPVQCVEGCHAHCPPGKILDELLQTCV

DPEDCPVCVAGRRFASGKKVTLNPSDPEHCQICHCDVVNLTCEACQEPGG

LVVPPTDAPVSPTTLYVEDISEPPLHQEPGGLVVPPTDAPVSPTTLYVED

ISEPPLHQEPGGLVVPPTDAPVSPTTLYVEDISEPPLHQEPGGLVVPPTD

APVSPTTLYVEDISEPPLHQEPGGLVVPPTDAPVSPTTLYVEDISEPPLH

According to one embodiment the amino acid sequence of the fusion protein has an identity of at least 90% to SEQ ID NO: 7. The amino acid sequence of the fusion protein may also have an identity of at least 95% to SEQ ID NO: 7. Furthermore, the identity to SEQ ID NO: 7 of the amino acid sequence of the fusion protein may be at least 98%. In particular, the amino acid sequence of the fusion protein may have an identity to SEQ ID NO: 7 of 100%.

A further representative fusion protein according to the invention is Pro-OCTA 14 including OCTA 14 and a pro-peptide (bold) with a signal peptide (bold and underlined). Pro-OCTA 14 is identified by SEQ ID NO: 8:

(SEQ ID NO: 8)
MIPARFAGVLLALALILPGTLCAEGTRGRSSTARCSLEGSDEVNTEDGSM

YSFAGYCSYLLAGGCQKRSFSIIGDFQNGKRVSLSVYLGEFFDIHLFVNG

TVTQGDQRVSMPYASKGLYLETEAGYYKLSGEAYGFVARIDGSGNFQVLL

SDRYFNKTCGLCGNENIFAEDDFMTQEGTLTSDPYDFANSWALSSGEQWC

ERASPPSSSCNISSGEMQKGLWEQCQLLKSTSVFARCHPLVDPEPFVALC

EKTLCECAGGLECACPALLEYARTCAQEGMVLYGWTDHSACSPVCPAGME

YRQCVSPCARTCQSLHINEMCQERCVDGCSCPEGQLLDEGLCVESTECPC

VHSGKRYPPGTSLSRDCNTCICRNSQWICSNEECPGECLVTGQSHFKSFD

NRYFTESGICQYLLARDCQDHSFSIVIETVQCADDRDAVCTRSVTVRLPG

LHNSLVKLKHGAGVAMDGQDVQLPLLKGDLRIQHTVTASVRLSYGEDLQM

DWDGRGRLLVKLSPVYAGKTCGLCGNYNGNQGDDFLTPSGLAEPRVEDFG

NAWKLHGDCQDLQKQHSDPCALNPRMTRFSEEACAVLTSPTFEACHRAVS

PLPYLRNCRYDVCSCSDGRECLCGALASYAAACAGRGVRVAWREPGRCEL

NCPKGQVYLQCGTPCNLTCRSLSYPDEECNEACLEGCFCPPGLYMDERGD

CVPKAQCPCYYDGEIFQPEDIFSDHHTMCYCEDGFMHCTMSGVPGSLLPD

AVLSSPLSHRSKRSLSCRPPMVKLVCPADNLRAEGLECTKTCQNYDLECM

SMGCVSGCLCPPGMVRHENRCVALERCPCFHQGKEYAPGETVKIGCNTCV

CQDRKWNCTDHVCDATCSTIGMAHYLTFDGLKYLFPGECQYVLVQDYCGS

NPGTFRILVGNKGCSHPSVKCKKRVTILVEGGEIELFDGEVNVKRPMKDE

THFEVVESGRYIILLLGKALSVVWDRHLSISVVLKQTYQEKVCGLCGNFD

GIQNNDLTSSNLQVEEDPVDFGNSWKVSSQCADTRKVPLDSSPATCHNNI

MKQTMVDSSCRILTSDVFQDCNKLVDPEPYLDVCIYDTCSCESIGDCACF

CDTIAAYAHVCAQHGKVVTWRTATLCPQSCEERNLRENGYECEWRYNSCA

PACQVTCQHPEPLACPVQCVEGCHAHCPPGKILDELLQTCVDPEDCPVCE

VAGRRFASGKKVTLNPSDPEHCQICHCDVVNLTCEACQEPGGLVVPPTDA

PVSPTTLYVEDISEPPLHQEPGGLVVPPTDAPVSPTTLYVEDISEPPLHQ

EPGGLVVPPTDAPVSPTTLYVEDISEPPLHQEPGGLVVPPTDAPVSPTTL

YVEDISEPPLHQEPGGLVVPPTDAPVSPTTLYVEDISEPPLH

According to one embodiment the amino acid sequence of the fusion protein has an identity of at least 90% to SEQ ID NO: 8. The amino acid sequence of the fusion protein may also have an identity of at least 95% to SEQ ID NO: 8. Furthermore, the identity to SEQ ID NO: 8 of the amino acid sequence of the fusion protein may be at least 98%. In particular, the amino acid sequence of the fusion protein may have an identity to SEQ ID NO: 8 of 100%.

A further representative fusion protein according to the invention is OCTA 15. OCTA 15 has the following amino acid sequence:

(SEQ ID NO: 9)
SLSCRPPMVKLVCPADNLRAEGLECTKTCQNYDLECMSMGCVSGCLCPPG

MVRHENRCVALERCPCFHQGKEYAPGETVKIGCNTCVCQDRKWNCTDHVC

DATCSTIGMAHYLTFDGLKYLFPGECQYVLVQDYCGSNPGTFRILVGNKG

CSHPSVKCKKRVTILVEGGEIELFDGEVNVKRPMKDETHFEVVESGRYII

LLLGKALSVVWDRHLSISVVLKQTYQEKVCGLCGNFDGIQNNDLTSSNLQ

VEEDPVDFGNSWKVSSQCADTRKVPLDSSPATCHNNIMKQTMVDSSCRIL

TSDVFQDCNKLVDPEPYLDVCIYDTCSCESIGDCACFCDTIAAYAHVCAQ

HGKVVTWRTATLCPQSCEERNLRENGYECEWRYNSCAPACQVTCQHPEPL

ACPVQCVEGCHAHCPPGKILDELLQTCVDPEDCPVCEVAGRRFASGKKVT

LNPSDPEHCQICHCDVVNLTCEACQEPGGLVVPPTDAPVSPTTLYVEDIS

EPPLHQEPGGLVVPPTDAPVSPTTLYVEDISEPPLHQEPGGLVVPPTDAP

VPTTLYVEDISEPPLHEEPECNDITARLQYVKVGSCKSEVEVDIHYCQGK

CASKAMYSIDINDVQDQCSCCSPTRTEPMQVALHCTNGSVVYHEVLNAME

CKCSPRKCSK

OCTA 15 is a fusion protein of the VWF fragment of amino acids 764 to 1268 of SEQ ID NO: 2, two copies of an extension peptide (bold) bound to the C-terminus consisting of the amino acids 1238 to 1268 of SEQ ID NO: 2 and the "cystein knot domain" of VWF consisting of amino acids 2721 to 2813 of SEQ ID NO: 2.

According to one embodiment the amino acid sequence of the fusion protein has an identity of at least 90% to SEQ ID NO: 9. The amino acid sequence of the fusion protein may also have an identity of at least 95% to SEQ ID NO: 9. Furthermore, the identity to SEQ ID NO: 9 of the amino acid sequence of the fusion protein may be at least 98%. In particular, the amino acid sequence of the fusion protein may have an identity to SEQ ID NO: 9 of 100%.

The following sequence (SEQ ID NO: 10) represents OCTA 15 with an additional 12 amino acid signal peptide (bold and underlined). An expression of this peptide provides a dimeric form of OCTA 15. The signal peptide is cleaved off.

(SEQ ID NO: 10)
MIPARFAGVLLALALILPGTLCSLSCRPPMVKLVCPADNLRAEGLECTKT

CQNYDLECMSMGCVSGCLCPPGMVRHENRCVALERCPCFHQGKEYAPGET

VKIGCNTCVCQDRKWNCTDHVCDATCSTIGMAHYLTFDGLKYLFPGECQY

VLVQDYCGSNPGTFRILVGNKGCSHPSVKCKKRVTILVEGGEIELFDGEV

NVKRPMKDETHFEVVESGRYIILLLGKALSVVWDRHLSISVVLKQTYQEK

VCGLCGNFDGIQNNDLTSSNLQVEEDPVDFGNSWKVSSQCADTRKVPLDS

SPATCHNNIMKQTMVDSSCRILTSDVFQDCNKLVDPEPYLDVCIYDTCSC

ESIGDCACFCDTIAAYAHVCAQHGKVVTWRTATLCPQSCEERNLRENGYE

CEWRYNSCAPACQVTCQHPEPLACPVQCVEGCHAHCPPGKILDELLQTCV

DPEDCPVCEVAGRRFASGKKVTLNPSDPEHCQICHCDVVNLTCEACQEPG

GLVVPPTDAPVSPTTLYVEDISEPPLHQEPGGLVVPPTDAPVSPTTLYVE

DISEPPLHQEPGGLVVPPTDAPVPTTLYVEDISEPPLHEEPECNDITARL

QYVKVGSCKSEVEVDIHYCQGKCASKAMYSIDINDVQDQCSCCSPTRTEP

MQVALHCTNGSVVYHEVLNAMECKCSPRKCSK

According to one embodiment the amino acid sequence of the fusion protein has an identity of at least 90% to SEQ ID NO: 10. The amino acid sequence of the fusion protein may also have an identity of at least 95% to SEQ ID NO: 10. Furthermore, the identity to SEQ ID NO: 10 of the amino acid sequence of the fusion protein may be at least 98%. In particular, the amino acid sequence of the fusion protein may have an identity to SEQ ID NO: 10 of 100%.

A further representative fusion protein according to the invention is Pro-OCTA 15 including OCTA 15 and a pro-peptide (bold) with a signal peptide (bold and underlined). The expression of this sequence will result in formation of multimers. Pro-OCTA 15 is identified by SEQ ID NO: 11:

(SEQ ID NO: 11)
MIPARFAGVLLALALILPGTLCAEGTRGRSSTARCSLFGSDFVNTFDGSM

YSFAGYCSYLLAGGCQKRSFSIIGDFQNGKRVSLSVYLGEFFDIHLFVNG

TVTQGDQRVSMPYASKGLYLETEAGYYKLSGEAYGFVARIDGSGNFQVLL

SDRYFNKTCGLCGNFNIFAEDDFMTQEGTLTSDPYDFANSWALSSGEQWC

ERASPPSSSCNISSGEMQKGLWEQCQLLKSTSVFARCHPLVDPEPFVALC

EKTLCECAGGLECACPALLEYARTCAQEGMVLYGWTDHSACSPVCPAGME

YRQCVSPCARTCQSLHINEMCQERCVDGCSCPEGQLLDEGLCVESTECPC

VHSGKRYPPGTSLSRDCNTCICRNSQWICSNEECPGECLVTGQSHFKSFD

NRYFTFSGICQYLLARDCQDHSFSIVIETVQCADDRDAVCTRSVTVRLPG

LHNSLVKLKHGAGVAMDGQDVQLPLLKGDLRIQHTVTASVRLSYGEDLQM

DWDGRGRLLVKLSPVYAGKTCGLCGNYNGNQGDDFLTPSGLAEPRVEDEG

NAWKLHGDCQDLQKQHSDPCALNPRMTRFSEEACAVLTSPTFEACHRAVS

PLPYLRNCRYDVCSCSDGRECLCGALASYAAACAGRGVRVAWREPGRCEL

NCPKGQVYLQCGTPCNLTCRSLSYPDEECNEACLEGCFCPPGLYMDERGD

CVPKAQCPCYYDGEIFQPEDIFSDHHTMCYCEDGEMHCTMSGVPGSLLPD

AVLSSPLSHRSKRSLSCRPPMVKLVCPADNLRAEGLECTKTCQNYDLECM

SMGCVSGCLCPPGMVRHENRCVALERCPCFHQGKEYAPGETVKIGCNTCV

CQDRKWNCTDHVCDATCSTIGMAHYLTFDGLKYLFPGECQYVLVQDYCGS

NPGTFRILVGNKGCSHPSVKCKKRVTILVEGGEIELFDGEVNVKRPMKDE

THFEVVESGRYIILLLGKALSVVWDRHLSISVVLKQTYQEKVCGLCGNFD

GIQNNDLTSSNLQVEEDPVDFGNSWKVSSQCADTRKVPLDSSPATCHNNI

MKQTMVDSSCRILTSDVFQDCNKLVDPEPYLDVCIYDTCSCESIGDCACF

CDTIAAYAHVCAQHGKVVTWRTATLCPQSCEERNLRENGYECEWRYNSCA

PACQVTCQHPEPLACPVQCVEGCHAHCPPGKILDELLQTCVDPEDCPVCE

VAGRRFASGKKVTLNPSDPEHCQICHCDVVNLTCEACQEPGGLVVPPTDA

PVSPTTLYVEDISEPPLHQEPGGLVVPPTDAPVSPTTLYVEDISEPPLHQ

EPGGLVVPPTDAPVPTTLYVEDISEPPLHEEPECNDITARLQYVKVGSCK

SEVEVDIHYCQGKCASKAMYSIDINDVQDQCSCCSPTRTEPMQVALHCTN

GSVVYHEVLNAMECKCSPRKCSK

According to one embodiment the amino acid sequence of the fusion protein has an identity of at least 90% to SEQ ID NO: 11. The amino acid sequence of the fusion protein may also have an identity of at least 95% to SEQ ID NO: 11. Furthermore, the identity to SEQ ID NO: 11 of the amino acid sequence of the fusion protein may be at least 98%. In particular, the amino acid sequence of the fusion protein may have an identity to SEQ ID NO: 11 of 100%.

According to one embodiment of the invention the fusion protein is a modified FVIII protein based on Simoctocog alfa with two or more copies of the extension peptide.

In this embodiment, the main protein is preferably identical or similar to the heavy chain of FVIII, in particular to amino acids 20 to 759 of UniprotKB P00451.1. The fusion protein with a main protein identical or similar to the heavy chain of FVIII, in particular to amino acids 20 to 759 of UniprotKB P00451.1, preferably additionally contains a linker similar or identical to SEQ ID NO: 12 and a further amino acid sequence similar or identical to the light chain as identified by amino acids 1668 to 2351 of UniprotKB entry P0045.1.

The extension peptides may be fused to the C-terminus of the light chain. Alternatively, the extension peptides are located between the heavy chain and the light chain. In this regard the extension peptides may be connected to the C-terminus or the N-terminus of the linker. The extension peptides may also replace the linker. Moreover, the linker sequence may be interrupted by one or more extension peptides. It is also possible that extension peptides are located both between heavy and the light chain and on the C-terminus of the light chain.

Preferably, the fusion protein based on Simoctocog alfa contains, from the N-terminus to the C-terminus, the heavy chain of FVIII, a first part of a linker, two or more, preferably three extension peptides (bold), a second part of a linker (underlined and bold) and the light chain. An example of such a protein is the protein identified by SEQ ID NO: 14:

(SEQ ID NO: 14)
ATRRYYLGAVELSWDYMQSDLGELPVDARFPPRVPKSFPFNTSVVYKKTL

FVEFTDHLFNIAKPRPPWMGLLGPTIQAEVYDTVVITLKNMASHPVSLHA

VGVSYWKASEGAEYDDQTSQREKEDDKVFPGGSHTYVWQVLKENGPMASD

PLCLTYSYLSHVDLVKDLNSGLIGALLVCREGSLAKEKTQTLHKFILLFA

VFDEGKSWHSETKNSLMQDRDAASARAWPKMHTVNGYVNRSLPGLIGCHR

KSVYWHVIGMGTTPEVHSIFLEGHTFLVRNHRQASLEISPITFLTAQTLL

MDLGQFLLFCHISSHQHDGMEAYVKVDSCPEEPQLRMKNNEEAEDYDDDL

TDSEMDVVRFDDDNSPSFIQIRSVAKKHPKTWVHYIAAEEEDWDYAPLVL

APDDRSYKSQYLNNGPQRIGRKYKKVRFMAYTDETFKTREAIQHESGILG

PLLYGEVGDTLLIIFKNQASRPYNTYPHGITDVRPLYSRRLPKGVKHLKD

FPILPGEIFKYKWTVTVEDGPTKSDPRCLTRYYSSFVNMERDLASGLIGP

LLICYKESVDQRGNQIMSDKRNVILFSVEDENRSWYLTENIQRFLPNPAG

VQLEDPEFQASNIMHSINGYVFDSLQLSVCLHEVAYWYILSIGAQTDFLS

-continued
VFFSGYTFKHKMVYEDTLTLFPFSGETVFMSMENPGLWILGCHNSDFRNR

GMTALLKVSSCDKNTGDYYEDSYEDISAYLLSKNNAIEPRSFSQNSRHQE

PGGLVVPPTDAPVSPTTLYVEDISEPPLHQEPGGLVVPPTDAPVSPTTLY

VEDISEPPLHQEPGGLVVPPTDAPVSPTTLYVEDISEPPLHRYRRGEITR

TTLQSDQEEIDYDDTISVEMKKEDFDIYDEDENQSPRSFQKKTRHYFIAA

VERLWDYGMSSSPHVLRNRAQSGSVPQFKKVVFQEFTDGSFTQPLYRGEL

NEHLGLLGPYIRAEVEDNIMVTFRNQASRPYSFYSSLISYEEDQRQGAEP

RKNFVKPNETKTYFWKVQHHMAPTKDEFDCKAWAYFSDVDLEKDVHSGLI

GPLLVCHTNTLNPAHGRQVTVQEFALFFTIFDETKSWYFTENMERNCRAP

CNIQMEDPTFKENYRFHAINGYIMDTLPGLVMAQDQRIRWYLLSMGSNEN

IHSIHFSGHVFTVRKKEEYKMALYNLYPGVFETVEMLPSKAGIWRVECLI

GEHLHAGMSTLFLVYSNKCQTPLGMASGHIRDFQITASGQYGQWAPKLAR

LHYSGSINAWSTKEPFSWIKVDLLAPMIIHGIKTQGARQKFSSLYISQFI

IMYSLDGKKWQTYRGNSTGTLMVFFGNVDSSGIKHNIFNPPIIARYIRLH

PTHYSIRSTLRMELMGCDLNSCSMPLGMESKAISDAQITASSYFTNMFAT

WSPSKARLHLQGRSNAWRPQVNNPKEWLQVDFQKTMKVTGVTTQGVKSLL

TSMYVKEFLISSSQDGHQWTLFFQNGKVKVFQGNQDSFTPVVNSLDPPLL

TRYLRIHPQSWVHQIALRMEVLGCEAQDLY

According to one embodiment the amino acid sequence of the fusion protein has an identity of at least 90% to SEQ ID NO: 14. The amino acid sequence of the fusion protein may also have an identity of at least 95% to SEQ ID NO: 14. Furthermore, the identity to SEQ ID NO: 14 of the amino acid sequence of the fusion protein may be at least 98%. In particular, the amino acid sequence of the fusion protein may have an identity to SEQ ID NO: 14 of 100%.

Alternatively, the fusion protein based on Simoctocog alfa contains two or more, preferably three extension peptides (bold) connected to the C-terminus of Simoctocog alfa. An example of such a protein is the protein identified by SEQ ID NO: 21. According to one embodiment the amino acid sequence of the fusion protein has an identity of at least 90% to SEQ ID NO: 21. The amino acid sequence of the fusion protein may also have an identity of at least 95% to SEQ ID NO: 21. Furthermore, the identity to SEQ ID NO: 21 of the amino acid sequence of the fusion protein may be at least 98%. In particular, the amino acid sequence of the fusion protein may have an identity to SEQ ID NO: 21 of 100%.

Polynucleotide

According to a second aspect, the invention provides an isolated polynucleotide that comprises a nucleic acid sequence encoding a fusion protein according to the first aspect of the invention.

The isolated polynucleotide may be a DNA molecule or an RNA molecule. The isolated polynucleotide is preferably a DNA molecule, in particular a cDNA molecule. The techniques used to isolate or clone a polynucleotide encoding a peptide are known in the art and include isolation from genomic DNA, preparation from cDNA, or a combination thereof. The cloning of the polynucleotides from such genomic DNA can be effected, e.g., by using the well-known polymerase chain reaction (PCR) or antibody screening of expression libraries to detect cloned DNA fragments with shared structural features (see, e.g., Innis et al, 1990) PCR: A Guide to Methods and Application, Academic Press, New York. Other nucleic acid amplification procedures such as ligase chain reaction (LCR), ligation activated transcription (LAT) and polynucleotide-based amplification (NASBA) may be used.

In particular, the sequence of the isolated polynucleotide may comprise a first part encoding the main protein and at least one second part sequence. The first part is preferably similar or identical to the SEQ ID NO: 15. The first part preferably has a degree of sequence identity SEQ ID NO: 15 of at least 80%, at least 85%, at least 90%, at least 95%, at least 96%, at least 97%, at least 98%, at least 99%, or 100%.

The at least one second part is preferably similar or identical to SEQ ID NO: 16. The second part preferably has a degree of sequence identity SEQ ID NO: 16 of at least 80%, at least 85%, at least 90%, at least 95%, at least 96%, at least 97%, at least 98%, at least 99%, or 100%.

The isolated polynucleotide may be a DNA molecule encoding a fusion protein with an amino acid sequence similar or identical to a sequence selected from the group consisting of SEQ ID NO: 4, SEQ ID NO: 5, SEQ ID NO: 7, SEQ ID NO: 8, SEQ ID NO: 10, SEQ ID NO: 11, SEQ ID NO: 14 and SEQ ID NO: 21.

In particular, the isolated polynucleotide may be a DNA molecule encoding a fusion protein having an amino acid sequence with an identity of at least 90%, preferably at least 95%, more preferably at least 98%, most preferably 100% to SEQ ID NO: 4. Alternatively, the isolated polynucleotide may be a DNA molecule encoding a fusion protein having an amino acid sequence with an identity of at least 90%. Moreover, the isolated polynucleotide may be a DNA molecule encoding a fusion protein having an amino acid sequence with an identity of at least 90%. preferably at least 95%, more preferably at least 98%, most preferably 100% to SEQ ID NO: 5. According to one embodiment the isolated polynucleotide is a DNA molecule encoding a fusion protein having an amino acid sequence with an identity of at least 90%. preferably at least 95%, more preferably at least 98%, most preferably 100% to SEQ ID NO: 7. According to one embodiment, the isolated polynucleotide is a DNA molecule encoding a fusion protein having an amino acid sequence with an identity of at least 90%. preferably at least 95%, more preferably at least 98%, most preferably 100% to SEQ ID NO: 8. According to one embodiment the isolated polynucleotide is a DNA molecule encoding a fusion protein having an amino acid sequence with an identity of at least 90%. preferably at least 95%, more preferably at least 98%, most preferably 100% to SEQ ID NO: 10. According to one embodiment the isolated polynucleotide is a DNA molecule encoding a fusion protein having an amino acid sequence with an identity of at least 90%. preferably at least 95%, more preferably at least 98%, most preferably 100% to SEQ ID NO: 11. According to one embodiment the isolated polynucleotide is a DNA molecule encoding a fusion protein having an amino acid sequence with an identity of at least 90%. preferably at least 95%, more preferably at least 98%, most preferably 100% to and SEQ ID NO: 14. According to one embodiment the isolated polynucleotide is a DNA molecule encoding a fusion protein having an amino acid sequence with an identity of at least 90%. preferably at least 95%, more preferably at least 98%, most preferably 100% to and SEQ ID NO: 21.

The isolated polynucleotide may be a DNA molecule with a sequence similar or identical to a sequence selected from the group consisting of SEQ ID NO: 17, SEQ ID NO: 18, SEQ ID NO: 19, SEQ ID NO: 20 and SEQ ID NO: 22.

According to one embodiment, one strand of the isolated polynucleotide has a sequence identity to SEQ ID NO: 17 of at least 80%, at least 85%, at least 90%, at least 95%, at least 96%, at least 97%, at least 98%, at least 99%, or 100%. According to a further embodiment, the isolated polynucleotide has a sequence identity to SEQ ID NO: 18 of at least 80%, at least 85%, at least 90%, at least 95%, at least 96%, at least 97%, at least 98%, at least 99%, or 100%. According to still another embodiment, the isolated polynucleotide has a sequence identity to SEQ ID NO: 19 of at least 80%, at least 85%, at least 90%, at least 95%, at least 96%, at least 97%, at least 98%, at least 99%, or 100%. According to one embodiment, the isolated polynucleotide has a sequence identity to SEQ ID NO: 20 of at least 80%, at least 85%, at least 90%, at least 95%, at least 96%, at least 97%, at least 98%, at least 99%, or 100%. According to one embodiment, the isolated polynucleotide has a sequence identity to SEQ ID NO: 20 of at least 80%, at least 85%, at least 90%, at least 95%, at least 96%, at least 97%, at least 98%, at least 99%, or 100%.

List of the Polynucleotide Sequences:
- SEQ ID NO: 15 DNA encoding OCTA 11 (AA 1-1268 of SEQ ID NO: 2)
- SEQ ID NO: 16 DNA encoding the extension peptide (SEQ ID NO: 1)
- SEQ ID NO: 17 DNA encoding Pro-OCTA 12 (SEQ ID NO: 5)
- SEQ ID NO: 18 DNA encoding Pro-OCTA 14 (SEQ ID NO: 8)
- SEQ ID NO: 19 DNA encoding Pro-OCTA 15 (SEQ ID NO: 11)
- SEQ ID NO: 20 DNA encoding Simoctocog alfa with three extension peptide in the linker region (SEQ ID NO 14)
- SEQ ID NO: 22 DNA sequence encoding Simoctocog alfa with three C-terminal extension peptides (SEQ ID NO: 21)

Expression Vector

In a third aspect the invention also relates to expression vectors comprising a polynucleotide according to the second aspect of the invention.

The expression vector further preferably comprises control elements such as a promoter, and transcriptional and translational stop signals. The polynucleotide according to the second aspect and of the control elements may be joined together to produce a recombinant expression vector that may include one or more restriction sites to allow for insertion or substitution of the polynucleotide encoding the polypeptide at such sites. The polynucleotide may be inserted into an appropriate expression vector for expression. In creating the expression vector, the coding sequence is located in the expression vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide of the fourth aspect of the invention. The choice of the expression vector will typically depend on the compatibility of the expression vector with the host cell into which the expression vector is to be introduced. The expression vectors may be a linear or closed circular plasmid.

The expression vector is preferably adapted to expression in mammalian cells. The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

The vector is preferably one that, when introduced into the host cell, is integrated into the genome and replicated together with the chromosome(s) into which it has been integrated. For integration into the host cell genome, the expression vector may rely on any other element of the expression vector for integration into the genome by homologous or non-homologous recombination. Alternatively, the vector may contain additional polynucleotides for directing integration by homologous recombination into the genome of the host cell at a precise location in the chromosome.

The vectors of the present invention preferably contain one or more (e.g., several) selectable markers that permit easy selection of transformed, transfected, transduced, or the like cells. A selectable marker is a gene the product of which provides for biocide or viral resistance, resistance to heavy metals, prototrophy to auxotrophs, and the like.

The procedures used to ligate the elements described above to construct the recombinant expression vectors of the present invention are well known to one skilled in the art (see, e.g., Sambrook et al., 1989, supra).

According to one embodiment the vector backbone of the vector according to the third aspect is selected from pCDNA3, pCDNA3.1, pCDNA4, pCDNA5, pCDNA6, pCEP4, pCEP-puro, pCET1019, pCMV, pEF1, pEF4, pEF5, pEF6, pExchange, pEXPR, pIRES, and pSCAS.

Host Cell

According to a fourth aspect the invention provides a host cell, comprising the expression vector according the third aspect of the invention. The expression vector according to the third aspect is introduced into a host cell so that the expression vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

According to one embodiment the fusion protein is produced by expression in a mammalian host cell line. The fusion protein is preferably produced in a human host cell line. Generally any human host cell line is suitable for expression of the fusion protein. A favourable glycosylation of the fusion protein is particularly obtained with human kidney cell lines. Preferred human kidney cell lines are HEK cell-lines, in particular HEK 293 cell lines.

Examples of HEK cell-lines for production of the glycosylated polypeptide are HEK 293 F, FIp-In™-293 (Invitrogen, R75007), 293 (ATCC® CRL-1573), 293 EBNA, 293 H (ThermoScientific 11631017), 293S, 293T (ATCC® CRL-3216™), 293T/17 (ATCC® CRL11268™), 293T/17 SF (ATCC® ACS4500™), HEK 293 STF (ATCC® CRL 3249™), HEK-293.2sus (ATCC® CRL-1573™). A preferred cell line for production of the polypeptide is the HEK 293 F cell line.

Other cell lines suitable as host cells for expression include cell lines derived from human myeloid leukemia cells. Specific examples of host cells are K562, NM-F9, NM-D4, NM-H9D8, NM-H9D8-E6, NM H9D8-E6Q12, GT-2X, GT-5s and cells derived from anyone of said host cells. K562 is a human myeloid leukemia cell line present in the American Type Culture Collection (ATCC CCL-243). The remaining cell lines are derived from K562 cells and have been selected for specific glycosylation features.

Use of the Fusion Protein

As shown in the examples, the extension peptides of SEQ ID NO: 1 in the fusion proteins OCTA 12 and OCTA 14 do not only lead to an increase of half-life of the fusion protein, i.e. as compared to the main protein, i.e. the VWF fragment. The fusion proteins OCTA 12 and OCTA 14, when administered together with FVIII, the binding partner of VWF, to a patient also lead to an increase in half-life of FVIII.

Thus, according to a fifth aspect, the invention provides the use of a fusion protein according to the first aspect for increasing the half-life of a second protein, wherein the fusion protein is capable of binding to said second protein.

The use can also be described as a method of treating a patient with a therapeutic protein, wherein the method comprises administering the therapeutic protein, e.g. an FVIII protein together with the fusion protein according to the first aspect.

Composition and Protein Complex

Accordingly, the concept according to the invention, namely the half-life prolongation provided by the extension peptides is not limited to the fusion protein, but in addition the half-life of a second protein, which is bound by the fusion protein, can be extended.

Thus, according to a sixth aspect the invention provides a composition of a first protein and a second protein, wherein said first protein is a fusion protein according to the first aspect and is capable of binding said second protein, and said second protein is a therapeutic protein comprising an amino acid sequence which is identical or similar to the amino acid sequence of a second mammalian protein or fragment thereof.

The first protein may bind to the second protein covalently or non-covalently to form a complex. Accordingly, the present invention also relates to a complex of a first protein and a second protein, wherein said first protein is a fusion protein according to the first aspect, and said second protein has an amino acid sequence which is identical or similar to the amino acid sequence of a second mammalian protein or fragment thereof. Accordingly, the complexes are formed by non-covalent binding of the first protein to the second protein.

According to one embodiment the first protein binds to the second protein covalently. The linker facilitating the binding of the first and second protein may be selected from a disulfide bridge, peptide bond, a chemical linker, or a glycosidic bond.

Alternatively the first protein binds to the second protein non-covalently. For the non-covalent binding, the first protein may, in particular, comprise a binding domain specific that renders it capable of binding to said second protein, i.e. a second protein binding domain. Depending on the location of the one or more extension peptides in the sequence of the first protein is may be located in different positions of the first protein. Preferably, the one or more extension peptides are located in a position that is exposed to the surface in the folded stated of the protein. The one or more extension peptides may be located in any position relative to the second protein binding site, e.g. the binding domain.

According to one embodiment of the composition, the one or more extension peptides are located in a position in the folded state of the first protein that does not interfere with the binding of the first protein to the second protein.

According to one embodiment, the half-life of the second protein, e.g. FVIII, bound to the first protein, e.g. a VWF fragment, is increased as compared to the free form of said second protein, e.g. a FVIII protein.

Preferably, the half-life of the second protein, e.g. a FVIII protein, bound to the first protein, e.g. OCTA 12, is increased as compared to said second protein bound to the native mammalian protein, e.g. mature VWF.

More preferably, the second protein, e.g. a FVIII protein, bound to the first protein, e.g. OCTA 12, is increased as compared to said second protein bound to the main protein without fusion peptide, e.g. OCTA 11.

The second mammalian protein may be selected from the same list as identified for the mammalian protein above. However, in the composition or complex, the second mammalian protein is not the same as the first mammalian protein.

According to one embodiment the second mammalian protein is a blood protein, in particular a human blood protein. Preferably the second mammalian protein is a coagulation factor, in particular a human coagulation factor.

According to one embodiment the second mammalian protein, to which the main protein is similar or identical, is human full length FVIII identified by amino acids 20 to 2,351 of UniProtKB P00451.1). According to another embodiment, the main protein is FVIII, in which at least part of the B-domain is missing. In this regard the entire B-domain may be missing. The missing part of the B-domain is optionally replaced by a linker. The linker sequence has in particular the following amino acids sequence SFSQNSRHQAYRYRRG (SEQ ID NO: 12). An example of a FVIII in which the B-domain is replaced by a linker, is Simoctocog alfa (SEQ ID NO: 13), the active ingredient of NUWIQ® or VIHUMA®.

According to one embodiment, the FVIII protein is a human FVIII protein with a reduced immune response in patients.

The reduced immune response of the FVIII protein is preferably based on the binding to SIGLECs SIG-5, SIG-7, SIG-8 and SIG-9. Without wanting to be bound to theory, it is believed that the binding to SIGLECS on antigen presenting cells (like e.g. dendritic cells) lead to down-regulation of pro-inflammatory and upregulation of immunosuppressive receptor expression on the cell surface. Also, the binding leads to an enhanced production of anti-inflammatory cytokines, lowers the production of pro-inflammatory cytokines, and in consequence leads to the inhibition of T-cell proliferation and antibody production. Thus, binding of the SIGLECs SIG-5, SIG-7, SIG-8 and SIG-9 leads to a reduced immune response or increased immune tolerance when the glycosylated polypeptide is administered to a patient.

The SIGLEC binding, and consequently, the reduced immune response is based on an increased number or percentage of sialylated core 2 and/or extended core 1 O-glycans in the glycosylated protein as compared to the number of sialylated core 2 and/or extended core 1 O-glycans of the naturally occurring human FVIII.

Thus, according to one embodiment the FVIII protein exhibits an increased number or percentage of sialylated core 2 and/or extended core 1 O-glycans in the glycosylated protein as compared to the number of sialylated core 2 and/or extended core 1 O-glycans of the naturally occurring human FVIII.

For the case that the second protein is an FVIII protein, the main protein of the first protein is preferably a fragment of VWF comprising the FVIII binding domain to make it capable of binding to the FVIII protein.

According to one embodiment of the composition, the first protein has an amino acid sequence with an identity of at least 95%, preferably at least 98% more preferably 100% to SEQ ID NO: 3 and the second protein has an amino acid with an identity of at least 95%, preferably at least 98% more preferably 100% to SEQ ID NO: 13.

According to one embodiment of the composition, the first protein has an amino acid sequence with an identity of at least 95%, preferably at least 98% more preferably 100% to SEQ ID NO: 6 and the second protein has an amino acid with an identity of at least 95%, preferably at least 98% more preferably 100% to SEQ ID NO: 13.

According to one embodiment of the composition, the first protein has an amino acid sequence with an identity of at least 95%, preferably at least 98% more preferably 100% to SEQ ID NO: 9 and the second protein has an amino acid with an identity of at least 95%, preferably at least 98% more preferably 100% to SEQ ID NO: 13.

Because in the blood of the patient the fusion protein containing the fragment of VWF, in particular OCTA 12, competes with endogenous VWF for binding to the FVIII protein, it is preferred that the composition comprises the fusion protein containing the fragment of VWF, in particular OCTA 12, in molar excess as compared to the FVIII protein.

Preferably, the molar ratio of the first protein to the second protein is in the range from 0.1 to 250, preferably in the range from 0.5 to 50 more preferably in the range from 1 to 25, most preferably in the range from 2 to 10.

To form a stable non-covalently bound complex and, therefore, allow the half-life prolongation of the second protein, the binding affinity of the first protein to the second protein defined by the equilibrium dissociation constant ($K_D$) should be below 10 µM. Preferably, the equilibrium dissociation constant of the VWF fragment in the first protein to the FVIII protein is in the range from 0.05 to 3 nM.

The first and second protein can be produced by separate recombinant expression and joined afterwards. Alternatively, the first and second protein are recombinantly expressed in the same cell. For this, the first and second protein may be encoded by the same vector or on two different vectors.

The VWF constructs used in the examples, i.e. OCTA 12, OCTA 14 and OCTA 15 were expressed in the form of their pro-proteins, leading to dimer formation or in case of OCTA 15 leading to multimer formation. These dimers remain intact even after cleavage of the pro-peptide and consequently each of the copies of the VWF construct in the dimer can bind to a FVIII protein. Thus, according to one embodiment, the complex contains two copies of the first and the second protein, wherein the two copies of the first protein form a dimer. This dimer of the first protein is preferably a non-covalently bound dimer.

Pharmaceutical Composition and Medical Use

As described above, the fusion protein according to the first aspect, the composition according to the sixth aspect and the complex according to the seventh aspect of the invention have the advantage of an increased half-life in the blood of patients and therefore increased therapeutic effect in patients. Therefore, the fusion protein according to the first aspect, the composition according to the sixth aspect, and the complex according to the seventh aspect are in particular useful as active ingredients for medical treatment. Preferably, they are useful for treatment or prevention of a bleeding disorder. The fusion protein according to the first aspect, the composition according to the sixth aspect, in particular protein complex, described herein can be administered alone or in the form of pharmaceutical compositions.

Thus, according to an eighth aspect, the invention provides a pharmaceutical composition of the fusion protein according to the first aspect, the composition according to the sixth aspect and the complex according to the seventh aspect.

According to the invention, the pharmaceutical composition may comprise an effective amount of fusion protein according to the first aspect, the composition according to the sixth aspect and the complex according to the seventh aspect formulated with at least one pharmaceutically acceptable carrier. Pharmaceutical compositions of the embodiments can be prepared and administered to a subject by any methods well known in the art of pharmacy. See, e.g., Goodman & Gilman's The Pharmacological Basis of Therapeutics, Hardman et al., eds., McGraw-Hill Professional (10th ed., 2001); Remington: The Science and Practice of Pharmacy, Gennaro, ed., Lippincott Williams & Wilkins (20th ed., 2003); and Pharmaceutical Dosage Forms and Drug Delivery Systems, Ansel et al. (eds), Lippincott Williams & Wilkins (7th ed., 1999). In addition, the pharmaceutical compositions of the embodiments may also be formulated to include other medically useful drugs or biological agents. The pharmaceutical composition typically comprises a therapeutically effective amount of the fusion protein or protein complex combined with a pharmaceutically acceptable carrier. The pharmaceutically acceptable carrier is any carrier known or established in the art. Exemplary pharmaceutically acceptable carriers include sterile pyrogen-free water and sterile pyrogen-free saline solution. Other forms of pharmaceutically acceptable carriers that can be utilized for the present embodiments include binders, disintegrants, surfactants, absorption accelerators, moisture retention agents, absorbers, lubricants, fillers, extenders, moisture imparting agents, preservatives, stabilizers, emulsifiers, solubilising agents, salts which control osmotic pressure, diluting agents such as buffers and excipients usually used depending on the use form of the formulation. These are optionally selected and used depending on the unit dosage of the resulting formulation.

Thus, the ninth aspect of the invention also relates to a method of treatment or prevention of a bleeding disorder of a patient, said method comprising administering to said patient a pharmaceutical composition according to the eighth aspect.

As used herein "bleeding disorder" refers to a disease or condition that impairs normal hemostasis. The bleeding disorder can be, for example, Hemophilia A, Hemophilia B, Factor VIII deficiency, Factor XI deficiency, von Willebrand Disease, Glanzmann's Thrombasthenia, Bernard Soulier Syndrome, idiopathic thrombocytopenic purpura, intracerebral hemorrhage, trauma, traumatic brain injury, and the like.

As used herein, "hemophilia" refers to a group of bleeding disorders associated with increased blood clot formation time as compared to blood clot formation time in healthy individuals without hemophilia. Hemophilia includes Hemophilia A, which is a disorder that leads to the production of defective Factor VIII, Hemophilia B, which is a disorder that leads to the production of defective Factor IX and acquired Hemophilia A, a rare bleeding disorder caused by an autoantibody to coagulation factor (F) VIII.

The bleeding disorder is preferably Hemophilia A or B. The treatment may for example be the hemophilia treatment of PUPS (Previously untreated patients) or an immune tolerance induction (ITI) treatment and/or other related treatments of haemophilia disorders.

For in vivo applications, pharmaceutical compositions can be administered to the patient by any customary administration route, e.g., orally, parenterally or by inhalation. Parenteral administration includes intravenous injection, subcutaneous injection, intraperitoneal injection, intramuscular injection, liquid agents, suspensions, emulsions and dripping agents. For parenteral administration the pharmaceutical composition should be an injectable agent such as a liquid agent or a suspension.

In other embodiments, the pharmaceutical composition is administered orally to a patient. In these embodiments, a form of the drug includes solid formulations such as tablets, coated tablets, powdered agents, granules, capsules and pills, liquid formulations such as liquid agents (e.g., eye drops, nose drops), suspension, emulsion and syrup, inhales such as aerosol agents, atomizers and nebulizers, and liposome inclusion agents. In still some other embodiments, the glycosylated polypeptide, protein complex or pharmaceutical composition is administered by inhalation to the respiratory tract of a patient to target the trachea and/or the lung of a subject.

According to one embodiment of the eighth aspect, the use comprises an intravenous or non-intravenous injection. The non-intravenous injection preferably is a subcutaneous injection.

All publications and patents cited in this disclosure are incorporated by reference in their entirety. To the extent the material incorporated by reference contradicts or is inconsistent with this specification, the specification will supersede any such material.

EXAMPLES

Example 1—Recombinant Expression of VWF Proteins

The following recombinant VWF proteins were transiently expressed in HEK cell line 293 F with a C-terminal Strep-Tag and purified by StrepTactin affinity chromatography (IBA GmbH):
OCTA 11
OCTA12
OCTA 12 is a fusion protein according to the invention. OCTA 11 is a comparative VWF fragment. The VWF proteins are schematically depicted in FIG. 1. Expression of Pro-proteins results in the formation of dimers. The peptide dimers remain also after cleavage of the propeptide.
Gene Synthesis and Cloning As a first step, genes encoding the pro-proteins of the VWF proteins were synthesized by GeneArt (Thermo Fisher Scientific):
Pro-OCTA 11
Pro-OCTA 12
The genes encoding the pro-proteins were cloned into the pDSG expression vector (IBA GmbH), containing a Twin-Strep-tag. Individual cultures of TOP10 *E. coli* (IBA GmbH) were transformed with the vector constructs and single clones were selected following an overnight incubation at 37° C. on ampicillin-containing LB-agar plates.

Plasmid DNA preparations were performed using the QIAamp DNA Mini or Maxi kit (Qiagen) according to the manufacturer's recommendations. By sequencing, the integrity of the vectors was verified, in particular the correct orientation and integrity of the genes encoding Pro-OCTA 11, Pro-OCTA 12.

Protein Expression

For eukaryotic expression of the VWF proteins, MEXi-293 cells (IBA GmbH) grown in MEXi transfection-medium (IBA GmbH), were transfected with 1.5 mg/l of the constructs using 4.5 mg/ml 25 kDa linear polyethylenimine. After 2-4 hour incubation at 37° C., 5% C02 and 100-150 rpm, the culture was diluted 1:2 with MEXi transfection-medium and cultivation was continued until cell viability reached 75%.

Subsequently, the supernatant was separated from cells by centrifugation at 4° C. and 300×g. In order to minimize the inhibitory effect of biotin in the cell culture medium and to adjust the pH, 0.1 volumes of buffer (1 M Tris-HCl, 1.5 mM NaCl, 10 mM EDTA, pH 8.0) and 0.09% (v/v) BioLock solution (IBA GmbH) was added to the supernatant and incubated for 20 min at 4° C.
Protein Purification After centrifugation, the supernatant was applied on the Strep-Tactin XT column (IBA GmbH), washed five times with washing buffer (100 mM Tris-HCl, 150 mM NaCl, 1 mM EDTA, pH 8.0) and bound Strep-tag containing proteins were eluted with elution buffer (100 mM Tris-HCl, 150 mM NaCl, 1 mM EDTA, 10 mM desthiobiotin, pH 8.0).

Example 2—Influence of Full-Length VWF or VWF Proteins on FVIII Half-Life when Co-Administered with FVIII to FVIII/VWF Double Knock Out (DKO) Mice 2.1 Background In this experiment, the influence of the VWF proteins produced according to Example 1 and full-length plasma derived VWF (pdVWF) on the half-life of FVIII was tested.

It is known that full-length VWF and FVIII are binding partners forming a non-covalent complex. The half-life of FVIII in circulation is determined mainly by the circulatory half-life of VWF.

As in serum endogenous VWF competes with administered VWF proteins (fragments) for FVIII binding, this competition would influence any effect of the administered VWF proteins on the half-life of FVIII.

Therefore, in the present experiment C57Bl/6 mice that are double knockouts for FVIII and VWF (FVIII/VWF-DKO) were used as model organisms for assessing the influence of the VWF on FVIII half-life.
2.2 Experimental Procedure
2.2.1 FVIII-Containing Products The following FVIII-containing products were produced:
1) FVIII alone
2) FVIII and OCTA 11
3) FVIII and OCTA 12
4) FVIII and pdVWF The VWF proteins OCTA 11 and OCTA 12 were produced as described in Example 1. The pdVWF was VWF concentrate WILATE® (Octapharma). The FVIII was B-domain deleted human cell line FVIII (NUWIQ® Octapharma). The NUWIQ® product contains the following buffer composition:

| | |
|---|---|
| Arginine HCl | 25.6 mM |
| Sucrose | 15.8 mM |
| NaCl | 308 mM |

| | |
|---|---|
| Pluronic F68 | 0.14 mM |
| Sodium citrate | 3.6 mM |
| Calcium chloride | 2.0 mM |

The molar ratio of VWF protein to FVIII in the FVIII containing products 2)-4) was 5:1. The VWF proteins were added to the NUWIQ® product (FVIII).

2.2.2 FVIII/VWF-DKO Mouse Strain

C57Bl/6 mice that are double knockouts for FVIII and VWF (FVIII/VWF-DKO) were used.

2.2.3 Administration of the Products

The four FVIII containing products were administered to 20 FVIII/VWF-DKO mice by tail vein infusion with a dose of 240 IU FVIII/kg (~6 IU/mouse).

2.2.4 Sampling and Analysis

Blood samples of the mice were taken at 5 minutes and 1, 4, 8, 12, 24, 36 and 48 hours after treatment with the FVIII containing products. The blood samples were obtained from the retro-orbital plexus of the mice. For each time point, blood samples from 5 mice per FVIII containing product were obtained and analyzed individually. Each mouse was sampled at 5 min time point and maximally at two additional time points.

FVIII activity in each of the blood samples was analyzed using the chromogenic assay (CHROMOGENIX).

2.3 Results

Figure 2:
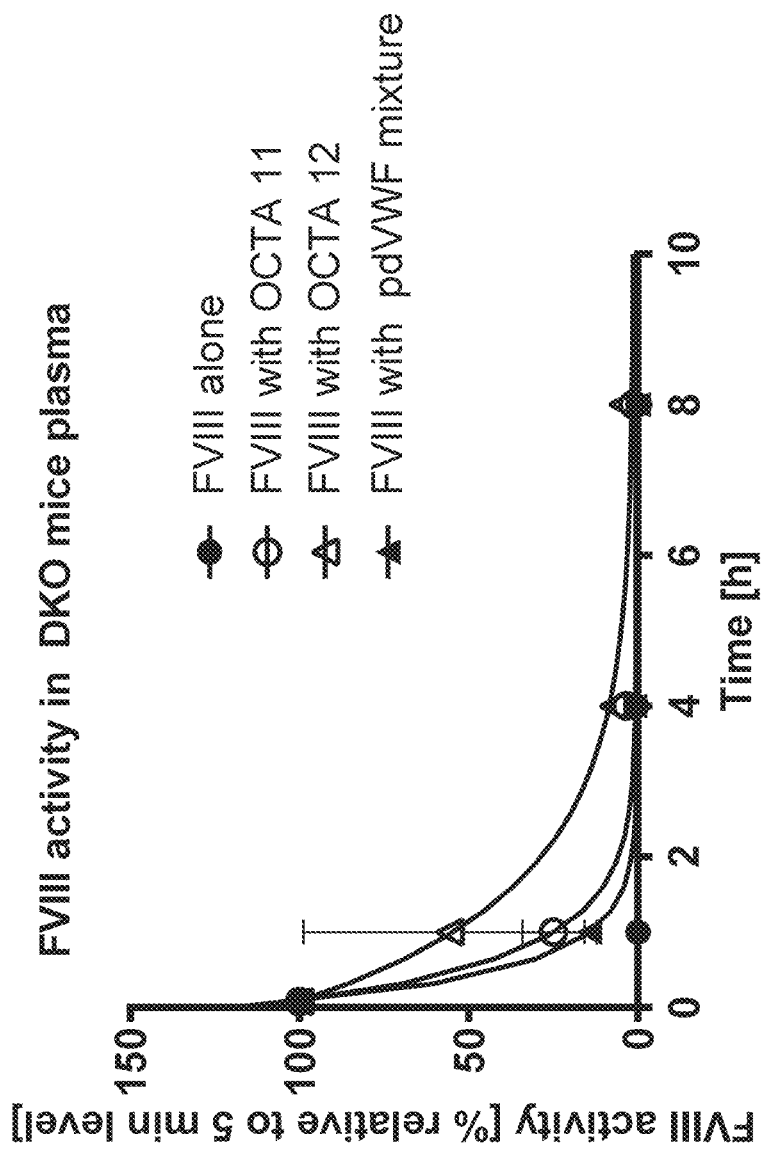

With the FVIII activity values in the blood samples a time course of the FVIII activity for each of the FVIII containing products was determined as a shown in FIG. 2.

As for each time point and FVIII containing product, blood samples of five animals were measured, each data point in the diagram of FIG. 2 represents the mean of 5 values.

Moreover, FVIII activity for the individual time points is given as a percentage FVIII activity 5 minutes after treatment, which was defined as 100% activity for each of the FVIII containing products.

The half-life of FVIII in five products was calculated after curve fitting using linear regression analysis of the log-linear portion of the individual plasma concentration-time curves or by non-linear regression using one-phase exponential decay model. Software programs used for calculation were GraphPad Prism version 6.07 (La Jolla, CA 92037 USA) and WinNonlin, version 6.4 (Pharsight Corporation, Mountain View, CA, USA).

The calculations were based on the following equations:

$$t_{\frac{1}{2}} = \frac{\ln 2}{K_{el}} \ [h]$$

$$\frac{dc}{dt} = K_{el} \cdot c \ [h]$$

$K_{el}$=elimination rate constant
$t_{1/2}$=elimination half-life
c=concentration
t=time The results are summarized in Table 1.

TABLE 1

Terminal half life of FVIII in the DKO mice

| FVIII containing product | $t_{1/2}$ [h] |
|---|---|
| 1)• FVIII alone | 0.07 |
| 2) FVIII and OCTA 11 | 0.45 |
| 3) FVIII and OCTA 12 | 1.03 |
| 4) FVIII and flVWF | 0.32 |

From these numbers it is apparent that co-administration of FVIII with any of the VWF proteins leads to an increase in half-life. Co-administration of FVIII with pdVWF leads to a ~4.6 fold increase of FVIII half-life (0.31).

The FVIII co-administered with the VWF protein OCTA 11 shows a comparable half-life of 0.45 h (about 1.4 fold increase).

Strikingly, co-administration with the VWF protein OCTA 12 gives a FVIII half-life of 1.03 h, which represents an increase of about 3.2 times in comparison to flVWF. The factor is 14.7-fold when compared to FVIII.

This result shows that the additional O-glycan repeats that are present in OCTA 12 lead to a significant half-life prolonging effect on the VWF-fragment and in turn on the VWF/FVIII complex. Moreover, this result shows that the addition of copies of an intrinsic O-glycan cluster may increase the half-life of a protein.

Example 3—Pharmacokinetic Profile of FVIII and VWF OCTA 12 Following IV and Subcutaneous (SQ) Administration in Minipigs 3.1 Background SQ delivery of drugs is becoming more and more interesting in the field of coagulation factors. However, due to very low recovery this route was not yet applicable for the administration of FVIII. Minipig is the best known animal model to test SQ administration of drugs due to close similarity to human structure of the epidermis. The aim of this experiment was the assessment of the half-life of VWF OCTA 12 and of FVIII when administered alone or with five-fold molar excess of OCTA 12 in minipig via the SQ route. Furthermore, the half-life of FVIII when administered alone via the conventional IV route was compared to FVIII administered SQ with or without VWF OCTA 12.

3.2 Experimental Procedure

Nine female Aachener minipigs with an age of 10 to 14 months were used for this study. The body weight was between 13.7 and 19.5 kg. IV injection was performed in the lateral ear vein, SQ injection under the skin in the inguinal region. The dose was 100 U FVIII/kg BW, 3 animals per group were treated with each product:

Group 1: FVIII alone SQ
Group 2: FVIII with OCTA 12 SQ
Group 3: FVIII alone IV

In order to obtain 2×200 μL Na-citrate plasma per animal and sampling time, sufficient blood was collected from the vena jugularis of all animals at the following time points: 0 (pre-dose), 0.5, 1, 2, 4, 8, 24, 32, 48, 72, 96 and 120 h after each administration.

The whole blood was sampled to tubes containing sodium citrate (0.15 M) as anticoagulant and cooled immediately using an IsoTherm-Rack system (Eppendorf). Plasma was separated by centrifugation within 30 minutes of blood withdrawal. Immediately after centrifugation, the plasma samples were frozen and stored at ≤−20° C. until shipment.

Each sample was tested for FVIII antigen using the Asserachrom assay kit (Diagnostica Stago). OCTA 12 was quantified using an ELISA assay as follows, Strep-Tactin® XT coated microplate (IBA GmbH) was blocked with blocking buffer (1% BSA in PBS) for 2 h at RT. Plasma samples were diluted in blocking buffer 1:15 and applied on the plate. After 2 h incubation at 37° C., the VWF fragment was detected with an anti VWF pAb (Dako P0226). After each incubation, the plate was washed 3 times with 0.1% Tween in PBS.

A pharmacokinetic evaluation of the analytical data was performed using WinNonlin, version 6.4 (Pharsight Corporation, Mountain View, CA, USA).

3.3 Results

Figure 3:
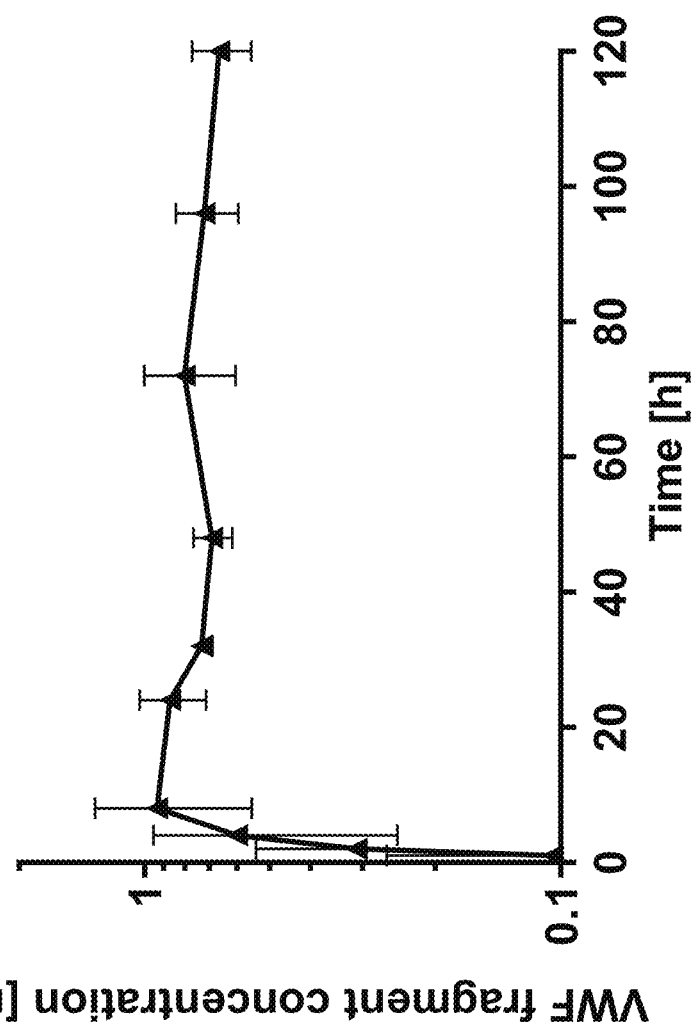
FIG. 3 shows a time-course of OCTA 12 antigen concentration following subcutaneous administration of 100 U/kg FVIII co-formulated with OCTA 12 in minipig plasma.

FIG. 3 shows the time course of VWF OCTA 12 concentration in minipig plasma after SQ administration of the FVIII/VWF OCTA 12 mixture. As summarized in Table 2, OCTA 12 circulates with a half life of 219.31 h. The half-life was determined as described in Example 2.

TABLE 2

Pharmacokinetic parameters of VWF OCTA 12 antigen in minipigs. The values represent mean +− SD of three animals.
Pharmacokinetic parameters of OCTA 12 antigen

| Group/Dosage/Route | $C_{max}$ [nM] | $t_{max}$ [h] | $t_{1/2}$ [h] |
|---|---|---|---|
| Group 2: 100 U/kg BW FVIII with OCTA 12 SQ. | 0.93 ± 0.38 | 8.00 | 219.31 |

$C_{max}$ highest measured plasma concentration
$t_{max}$ time of Cmax
$t_{1/2}$ terminal half-life In von Willebrand disease (VWD) pigs, the half-life of full length recombinant human (rhVWF) is ~10 to 16 hours, and the half life of plasma derived porcine VWF is between 10 and 18 hours (Nichols et al.). The half-life of a VWF fragment containing the FVIII binding domains only is shorter than the half-life of flVWF as shown by Yee et al. in VWF deficient mice. Therefore, OCTA 12 half-life is approximately 14-22 times longer than the half-life of rhVWF in pig.

Figure 4:
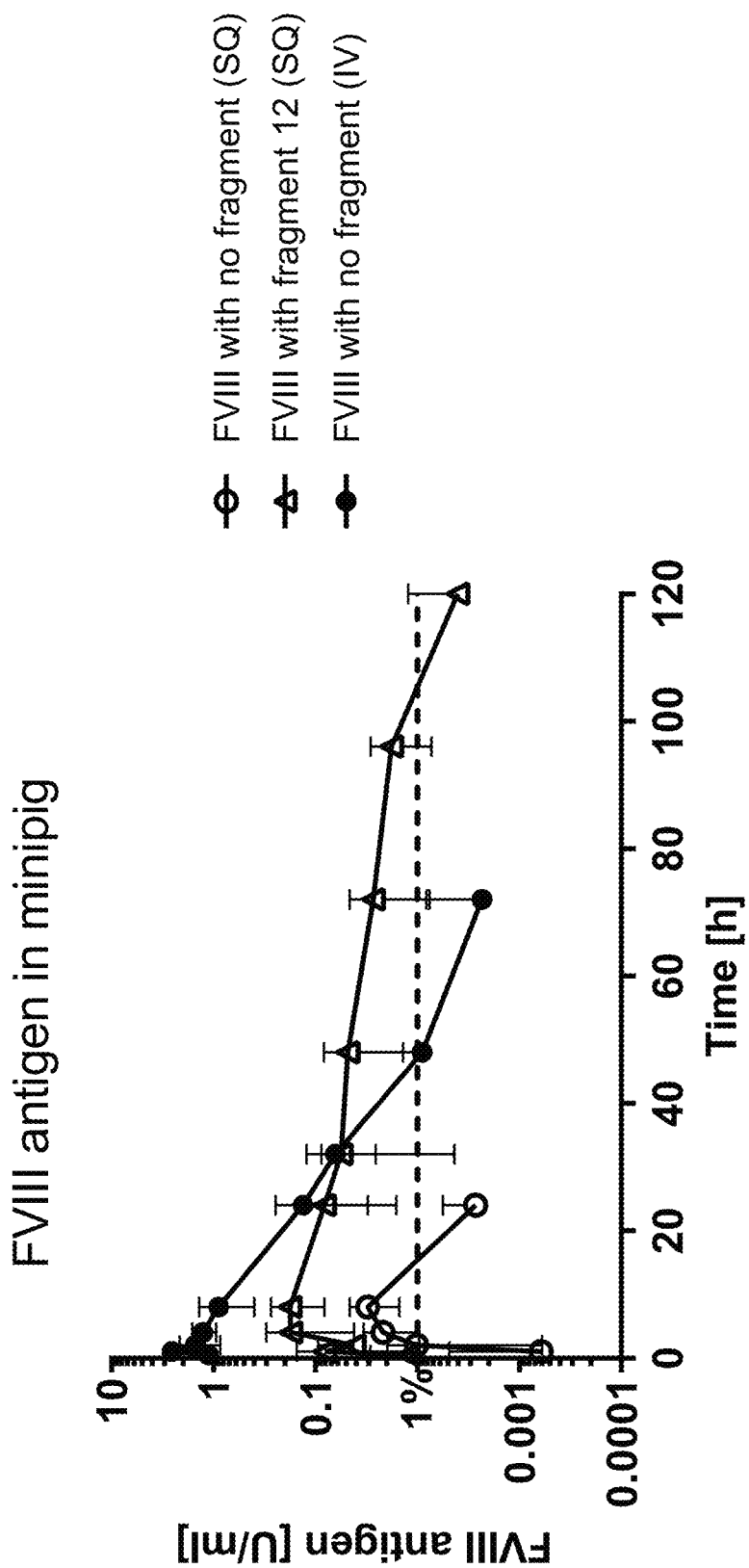
FIG. 4 shows the time-course of FVIII antigen concentration following subcutaneous and intravenous injection of 100 U/kg FVIII or subcutaneous 100 U/kg FVIII co-formulated with VWF-protein OCTA 12 in minipig plasma.

In addition, a significant prolonging effect on FVIII half-life was also observed. As shown in FIG. 4 and summarized in Table 3, FVIII when co-administered with OCTA 12 has a half life of 25.3 h, which represents 6.7-fold increase in half life when comparing with FVIII alone administered via the same route (SQ), and 3.9-fold improvement when comparing with FVIII administered alone via the conventional IV route.

TABLE 3

Pharmacokinetic parameters of FVIII antigen in minipigs. The values represent mean +− SD of three animals.
Pharmacokinetic parameters of FVIII Antigen

| Group/Dosage/Route | $C_{max}$ [U/mL] | $t_{max}$ [h] | $t_{1/2}$ [h] |
|---|---|---|---|
| Group 1: 100 U/kg BW FVIII alone SQ | 0.03 ± 0.015 | 8.00 | 3.78 ± 1.31 |
| Group 2: 100 U/kg BW FVIII with OCTA 12 SQ | 0.178 ± 0.09 | 8.00 | 25.30 ± 11.24 |
| Group 3: FVIII alone IV | 2.56 ± 0.26 | 1.00 | 6.45 ± 2.32 |

Many modifications and other embodiments of the invention set forth herein will come to the mind of the one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

REFERENCES

Birken S, Canfield R E. Isolation and amino acid sequence of COOH-terminal fragments from the beta subunit of human choriogonadotropin. J Biol Chem. 1977; vol. 252 pg. 5386-5392

Ewenstein B M, Collins P, Tarantino M D, Negrier C, Blanchette V, Shapiro A D, Baker D, Spotts G, Sensel M, Yi S E, Gomperts E D. Hemophilia therapy innovation development of an advanced category recombinant factor VIII by a plasma/albumin-free method Proceedings of a Special Symposium at the XIXth Congress of the International Society on Thrombosis and Haemostasis; 2004, vol. 41, pg. 1-16.

Fischer B, Mitterer A, Schlokat U, DenBouwmeester R, Dorner "Structural analysis of recombinant von Willebrand factor: identification of hetero- and homo-dimers" FFEBS Lett. 1994 Sep. 12; 351(3): 345-8. Erratum in: FEBS Lett 1994 Oct. 24; 353(3):337.

Furlan M. "Von Willebrand factor: molecular size and functional activity" Ann Hematol. 1996 June; 72(6):341-8.

Kannicht C, Ramstrom M, Kohla G, et al. Characterisation of the post-translational modifications of a novel, human cell line-derived recombinant human factor VIII. Thromb Res. 2013; 131(1):78-88.

Needleman S B, Wunsch C D. A general method applicable to the search for similarities in the amino acid sequence of two proteins. J Mol Biol. 1970; vol. 48(3); pg. 443-453.

Nichols T C, Bellinger D A, Merricks E P, et al. Porcine and Canine von Willebrand Factor and von Willebrand Disease: Hemostasis, Thrombosis, and Atherosclerosis Studies. Thrombosis. 2010; 2010:461238.

Strohl W R. Fusion Proteins for Half-Life Extension of Biologics as a Strategy to Make Biobetters. BioDrugs. 2015 August; vol. 29(4), pg. 215-239.

Tiede A. Half-life extended factor VIII for the treatment of hemophilia A. J Thromb Haemost. 2015 June; vol. 13 Suppl 1; pg. S176-179

Vlot A J, Koppelman S J, Meijers J C, Dama C, van den Berg H M, Bouma B N, Sixma J J, Willems G M. Kinetics of factor VII-von Willebrand factor association. Blood. 1996 1; vol. 87(5); pg. 1809-1816

Yee A, Gildersleeve R D, Gu S, Kretz C A, McGee B M, Carr K M, Pipe S W, Ginsburg D. A von Willebrand factor fragment containing the D'D3 domains is sufficient to stabilize coagulation factor VIII in mice. Blood. 2014 Jul. 17; vol. 124(3); pg. 445-452.

Innis et al, 1990 PCR: A Guide to Methods and Application, Academic Press, New York.

The invention claimed is:

1. A fusion protein comprising a main protein and two or more extension peptides, wherein the amino acid sequence of the main protein is at least 90% identical to the amino acid sequence of a mammalian protein or a fragment thereof; wherein the two or more extension peptides are consecutive, and each of the two or more extension peptides consists of the amino acid sequence that is at least 90% identical to the amino acid sequence of SEQ ID NO: 1 and comprises a cluster of O-glycosylated amino acids; and wherein the fusion protein has an increased half-life compared to the main protein without the two or more extension peptides.

2. The fusion protein according to claim 1, wherein the cluster of O-glycosylated amino acids in each of the two or more extension peptides contains at least three O-glycosylated amino acids.

3. The fusion protein according to claim 1, wherein the cluster of O-glycosylated amino acids in each of the two or more extension peptides contains at least one threonine as O-glycosylated amino acids.

4. The fusion protein according to claim 1, wherein each of the two or more extension peptides contains at least one O-glycosylated amino acid in eight consecutive amino acids.

5. The fusion protein according to claim 1, wherein each of the two or more extension peptides consists of the amino acid sequence that is at least 95% identical to the amino acid sequence of SEQ ID NO: 1.

6. The fusion protein according to claim 1, comprising at least four copies of the extension peptide.

7. The fusion protein according to claim 1, wherein one extension peptide is directly or indirectly fused to the C-terminus of the main protein.

8. The fusion protein according to claim 1, wherein one extension peptide forms the C-terminus of the fusion protein, and wherein the C-terminal amino acid of said extension peptide is optionally linked to an affinity tag peptide.

9. The fusion protein according to claim 1, wherein the main protein comprises at least one cluster of O-glycosylated amino acids.

10. The fusion protein according to claim 1, wherein the main protein comprises a dimerization domain.

11. The fusion protein according to claim 1, wherein the mammalian protein is a human blood protein selected from the group consisting of von Willebrand factor (VWF), prothrombin, fibrinogen, factor III (FIII), factor V (FV), factor VII (FVII), factor VIII (FVIII), factor IX (FIX), factor X (FX), factor XI (FXI), factor XII (FXII), factor XIII (FXIII), a disintegrin and metalloproteinase with a thrombospondin type 1 motif member 13 (ADAMTS13), antithrombin, alpha-1 antitrypsin, C1-inhibitor, antichymotrypsin, plasminogen activator inhibitor 1 (PAI-1), plasminogen activator inhibitor 3 (PAI-3), 2-macroglobulin, tissue factor pathway inhibitor (TFPI), heparin cofactor II, Protein Z, Protein C, and Protein S.

12. The fusion protein according to claim 1, wherein the main protein has a sequence identity of at least 90% to amino acids 764 to 1268 of SEQ ID NO: 2.

13. The fusion protein according to claim 1, wherein the fusion protein comprises at least 8 additional O-glycans compared to the main protein.

14. The fusion protein according to claim 1, wherein the amino acid sequence of the fusion protein has an identity of at least 95% to a sequence selected from SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11.

15. The fusion protein according to claim 1, wherein the fusion protein is produced by expression in a human kidney cell line.

16. A composition comprising a first protein and a second protein, wherein said first protein is a fusion protein according to claim 1 and is capable of binding to said second protein, and said second protein is a therapeutic protein comprising the amino acid sequence that is at least 90% identical to the amino acid sequence of a mammalian protein or fragment thereof.

17. The composition according to claim 16, wherein the half-life of the second protein bound to the first protein is increased as compared to the free form of said second protein.

18. The composition according to claim 16, wherein the molar ratio of the first protein to the second protein is in the range of 0.1 to 250.

19. The composition according to claim 16, wherein the binding affinity of the first protein to the second protein is in the range of 0.05 to 3 nM.

20. The composition according to claim 16, wherein the second protein is a blood protein.

21. The composition according to claim 20, wherein the mammalian protein is a human protein.

22. The composition according to claim 16, wherein the second protein is an FVIII protein selected from the group consisting of full length FVIII, an FVIII protein in which at least a part of the B-domain is missing, and an FVIII protein in which at least a part of the B-domain is replaced by an extension peptide, wherein the extension peptide consists of the amino acid sequence that is at least 90% identical to the amino acid sequence of SEQ ID NO: 1 and comprises a cluster of O-glycosylated amino acids.

23. A complex of a first protein and a second protein, wherein said first protein is a fusion protein according to claim 1, and said second protein comprises the amino acid sequence that is at least 90% identical to the amino acid sequence of a mammalian protein or fragment thereof.

24. The complex according to claim 23, wherein the first protein is non-covalently bound to the second protein.

25. The complex according to claim 23, containing two copies of each of the first protein and the second protein, wherein the two copies of the first protein form a dimer.

26. The complex according to claim 23, wherein the first protein is covalently bound to the second protein via a linker, and wherein the linker is selected from a peptide bond, a chemical linker, or a glycosidic bond.

27. A pharmaceutical composition comprising the fusion protein according to claim 1.

28. A fusion protein comprising a main protein and one or more extension peptides, wherein the amino acid sequence of the main protein is at least 90% identical to the amino acid sequence of a mammalian protein or a fragment thereof that is at least 50 amino acids in length; wherein the main protein is selected from the group consisting of prothrombin, fibrinogen, factor III (FIII), factor V (FV), factor VII (FVII), factor IX (FIX), factor X (FX), factor XI (FXI), factor XII (FXII), factor XIII (FXIII), a disintegrin and metalloproteinase with a thrombospondin type 1 motif, member 13 (ADAMTS13), antithrombin, alpha-1 antitrypsin, C1-inhibitor, antichymotrypsin, plasminogen activator inhibitor 1 (PAI-1), plasminogen activator inhibitor 3 (PAI-3), 2-macroglobulin, tissue factor pathway inhibitor (TFPI), heparin cofactor II, Protein Z, Protein C, and Protein S; wherein the one or more extension peptides consists of the amino acid sequence that is at least 90% identical to the amino acid sequence of SEQ ID NO: 1 and comprises a cluster of O-glycosylated amino acids; and wherein the fusion protein has an increased half-life compared to the main protein without the one or more extension peptides.

\* \* \* \* \*